(12) United States Patent
Peet et al.

(10) Patent No.: US 11,319,525 B2
(45) Date of Patent: May 3, 2022

(54) APPARATUS, METHODS AND COMPOSITION FOR SYNTHESIS OF CANNABINOID COMPOUNDS

(71) Applicant: TEEWINOT TECHNOLOGIES LIMITED, Dublin (IE)

(72) Inventors: Richard Peet, Washington, DC (US); Malcolm J. Kavarana, Fairfax, VA (US); Mingyang Sun, Dublin (IE); Peter C. Michels, Voorheesville, NY (US); John D. Rabenstein, Feura Bush, NY (US); C. Seth Pearson, Albany, NY (US); Geoffrey M. Fox, Voorheesville, NY (US)

(73) Assignee: TEEWINOT LIFE SCIENCES CORPORATION, New York, NY (US)

( * ) Notice: Subject to any disclaimer, the term of this patent is extended or adjusted under 35 U.S.C. 154(b) by 105 days.

(21) Appl. No.: 16/453,578

(22) Filed: Jun. 26, 2019

(65) Prior Publication Data
US 2019/0382708 A1    Dec. 19, 2019

Related U.S. Application Data

(63) Continuation of application No. 15/976,487, filed on May 10, 2018, now Pat. No. 10,336,978, which is a
(Continued)

(51) Int. Cl.
*C12M 1/34* (2006.01)
*C12M 1/36* (2006.01)
(Continued)

(52) U.S. Cl.
CPC .............. *C12M 41/30* (2013.01); *C12M 1/34* (2013.01); *C12M 1/36* (2013.01); *C12M 1/40* (2013.01);
(Continued)

(58) Field of Classification Search
CPC ...... C12M 41/30; C12M 41/26; C12M 41/40; C12M 41/12; C12P 17/06; C12P 7/42
See application file for complete search history.

(56) References Cited

U.S. PATENT DOCUMENTS 9,861,609 B2 * 1/2018 Winnicki ............. A61K 31/352
2015/0361469 A1 * 12/2015 Winnicki ............. C12N 9/1029
435/125
(Continued)

OTHER PUBLICATIONS

Karande et al., "Enzyme Catalysis in an Aqueous/Organic Segment Flow Microreactor: Ways to Stabilize Enzyme Activity," Langmuir, vol. 26, No. 11, 2010, pp. 9152-9159.
(Continued)

*Primary Examiner* — Michael L Hobbs
(74) *Attorney, Agent, or Firm* — Saul Ewing Arnstein & Lehr LLP; Alireza Behrooz

(57) ABSTRACT

The disclosure provides systems and methods for producing a cannabinoid product, which comprises contacting a cannabinoid precursor in a first phase with a cannabinoid synthase in a second phase, wherein the first phase and the second phase are substantially immiscible or immiscible. The disclosure also provides a composition comprising the cannabinoid precursor in a first phase and a cannabinoid synthase in a second phase, wherein the first phase and the second phase are substantially immiscible or immiscible.

19 Claims, 46 Drawing Sheets

Related U.S. Application Data continuation of application No. PCT/US2018/029638, filed on Apr. 26, 2018.

(60) Provisional application No. 62/514,626, filed on Jun. 2, 2017, provisional application No. 62/514,617, filed on Jun. 2, 2017, provisional application No. 62/490,577, filed on Apr. 26, 2017, provisional application No. 62/490,579, filed on Apr. 26, 2017.

(51) Int. Cl.
*C12M 1/40* (2006.01)
*C12M 1/00* (2006.01)
*C12P 7/42* (2006.01)
*C12P 17/06* (2006.01)

(52) U.S. Cl.
CPC ............ *C12M 21/18* (2013.01); *C12M 23/58* (2013.01); *C12M 41/12* (2013.01); *C12M 41/26* (2013.01); *C12M 41/40* (2013.01); *C12M 41/48* (2013.01); *C12M 47/10* (2013.01); *C12P 7/42* (2013.01); *C12P 17/06* (2013.01)

(56) References Cited

U.S. PATENT DOCUMENTS

| | | |
|---|---|---|
| 2016/0053220 A1 | 2/2016 | Peet et al. |
| 2016/0168595 A1 | 6/2016 | Janssen et al. |
| 2016/0355854 A1 | 12/2016 | Winnicki et al. |

OTHER PUBLICATIONS

Taura et al., "Cannabidiolic-acid synthase, the chemotype-determining enzyme in the fiber-type Cannabis sativa," FEBS Letters, vol. 581, 2007, pp. 2929-2934.

International Search Report and Written Opinion issued in corresponding application No. PCT/US2018/029638 dated Jul. 19, 2018.

Post-issuance third party submission filed on Dec. 28, 2020 in parent U.S. Pat. No. 10,336,978.

Lange, K. et al., "Δ9-Tetrahydrocannabinolic acid synthase production in Pichia pastoris enables chemical synthesis of cannabinoids", Journal of Biotechnology, Oct. 10, 2015, pp. 68-76, vol. 211.

Lange, K. et al., "Δ9-Tetrahydrocannabinolic acid synthase: The application of a plant secondary metabolite enzyme in biocatalytic chemical synthesis", Journal of Biotechnology, Sep. 10, 2016, pp. 42-48, vol. 233.

Roberts, J.D. et al., Organic Chemistry: methane to macromolecules, W.A. Benjamin, Inc., N.Y. (1971) pp. 47-55.

Taura, F. et al., "Biosynthetic Study on THCA, the Psychoactive Component of Marijuana," Seibutsu Butsuri [Biophysics], vol. 45, No. 4, 2005, pp. 178-184 (with English translation).

Extended European Search Report dated Jan. 21, 2021 in counterpart EP App. No. 18789802.8.

\* cited by examiner

FIG. 3A
FIG. 3B
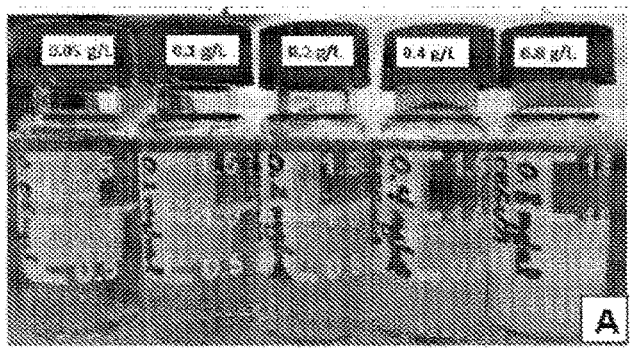
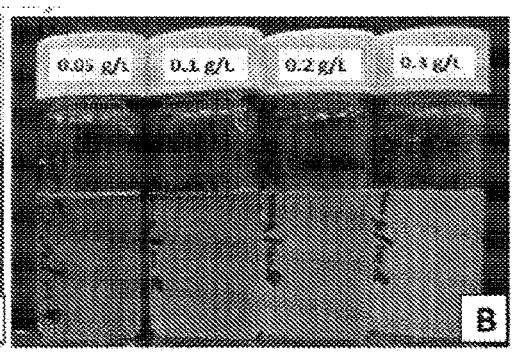
FIG. 4
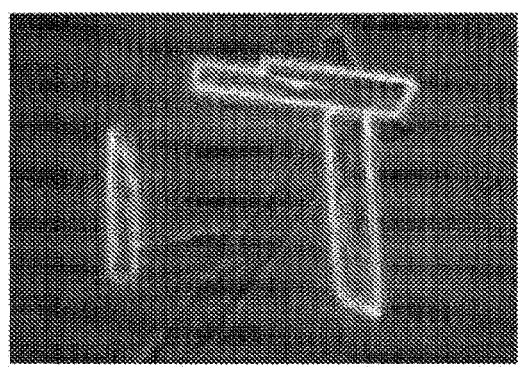

FIG. 15A
FIG. 15B
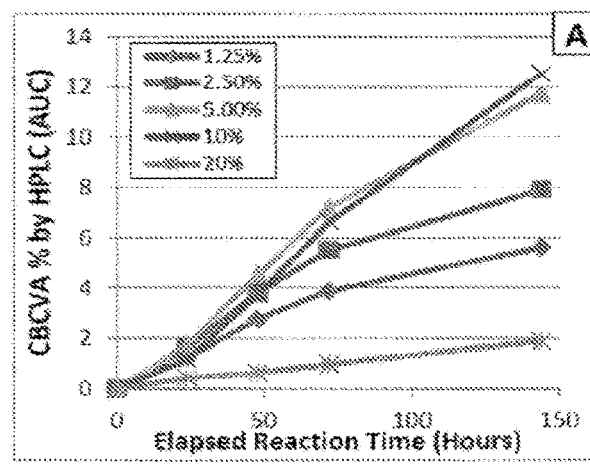
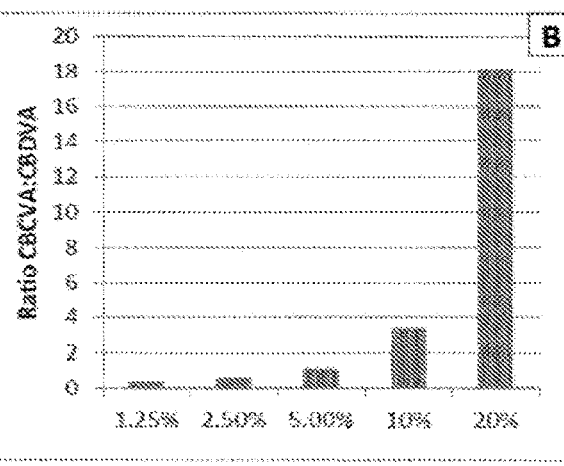
FIG. 16
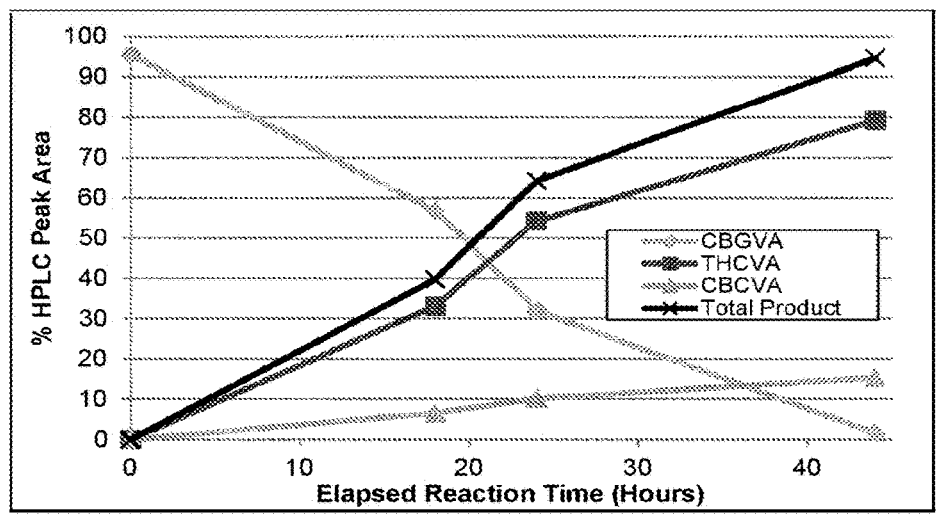

FIG. 34A
FIG. 34B
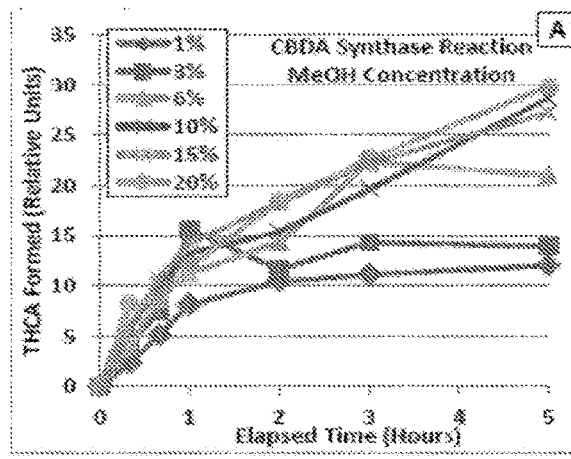
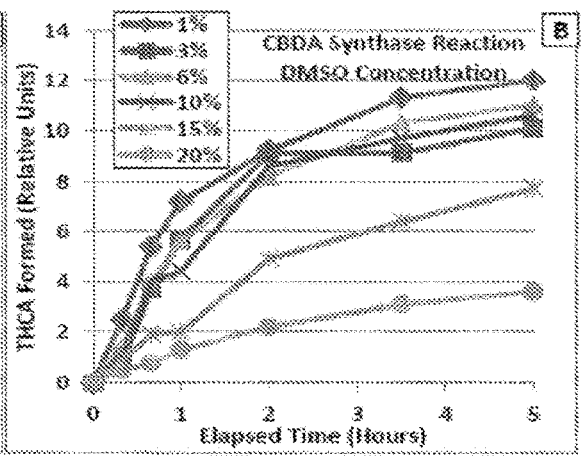
FIG. 35A
FIG. 35B
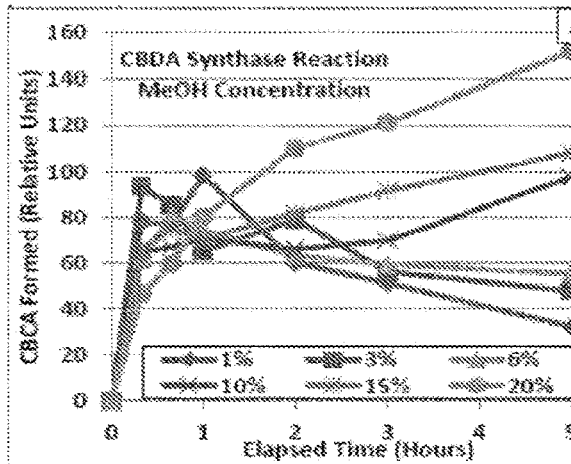
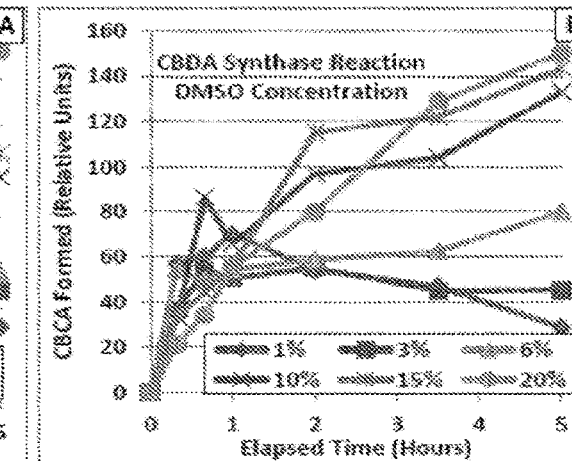

APPARATUS, METHODS AND COMPOSITION FOR SYNTHESIS OF CANNABINOID COMPOUNDS

CROSS-REFERENCE TO RELATED PATENT APPLICATIONS

This application is a Continuation of U.S. patent application Ser. No. 15/976,487, filed May 10, 2018, now U.S. Pat. No. 10,336,978, which is a Continuation of PCT application No: PCT/US2018/029638, filed Apr. 26, 2018, which claims priority under 35 U.S.C. § 119(e) to U.S. Provisional Application Nos. 62/490,577, filed Apr. 26, 2017, 62/490,579, filed on Apr. 26, 2017, 62/514,617, filed on Jun. 2, 2017, and 62/514,626, filed on Jun. 2, 2017. The content of each application is hereby incorporated by reference in its entirety.

BACKGROUND OF THE INVENTION

Cannabinoids are terpenophenolic compounds found in *Cannabis sativa*, an annual plant belonging to the Cannabaceae family. The plant produces more than 100 different cannabinoids. Cannabinoids accumulate mainly in the glandular trichomes. Classical cannabinoid compounds include tetrahydrocannabinol (THC), prescribed by physicians as dronabinol (Marinol®) or nabilone (Cesamet®), which is used for treating glaucoma, AIDS wasting, and chemotherapy-induced nausea. THC may also be effective in the treatment of allergies, inflammation, epilepsy, depression, migraine, bipolar disorders, anxiety disorder, drug dependency, neuropathic pain, treatment of spasticity associated with multiple sclerosis, fibromyalgia, and drug withdrawal syndromes.

Cannabinoids have therapeutic potential. For example, cannabidiol (CBD) is a potent antioxidant and anti-inflammatory compound and may provide protection against acute and chronic neuro-degeneration. It is found in high concentrations in hemp and acts as a high affinity α2-adrenergic receptor agonist, moderate affinity 5-HT1A receptor antagonist and low affinity CB1 receptor antagonist. CBD may also have anti-depressant activity. Cannabichromene (CBC) possesses anti-inflammatory, anti-fungal, and anti-viral properties. Thus, cannabinoids are considered to be promising agents for their beneficial effects in the treatment of various diseases.

The varins are a class of cannabinoids that are structurally different from the classical cannabinoids (e.g., THC, CBD, CBG, or CBC). Instead of having a pentyl (5-carbon) side chain attached to the aromatic ring as present in the classical cannabinoids, varins have a 3-carbon propyl side chain. Many of the varins are found in very low amounts in the *Cannabis* plant. Tetrahydrocannabivarin (THCV) is one of the most studied cannabinoid varin compounds. THCV can function as an antagonist of THC at CB1 receptors and thus attenuate the psychoactive effects of THC. THCV has also been shown as a potential treatment for type 2 diabetes by increasing insulin sensitivities and improving glucose tolerance. Wargent et al., *Nutr Diabetes.*, May; 3(5): e68 (2013). THCV has also shown promise for treatment of epilepsy and to reduce tremors associated with Parkinson's diseases.

Despite their known beneficial effects, therapeutic use of cannabinoid compounds, particularly varins, is hampered by the difficulty in obtaining high yields of cannabinoid compounds (both pentyl and propyl chain cannabinoids) from plants. Moreover, extraction, isolation, and purification of cannabinoid compounds from plant tissue are particularly challenging for a variety of reasons, including the difficulty of separating cannabinoids from terpenes, chlorophyll, and other plant components and the fact that the *Cannabis* plant only produces small quantities of many of these cannabinoids.

Therefore, the practical challenges in isolating the natural cannabinoid compounds from plants highlights a need for developing effective, safe systems or methods for large scale production of cannabinoid compounds for therapeutic use, especially, since chemical methods for synthesizing many of the cannabinoids and rarer varins are not yet available in the published literature.

SUMMARY OF INVENTION

It is therefore an object of the disclosure to provide solutions to the aforementioned deficiencies in the art. To this end, the present disclosure relates generally to systems and methods for producing a cannabinoid product. In one embodiment, the system for producing a cannabinoid or its analog, comprising: a) fermentor holding a medium and a plurality of cells, wherein the cells are configured to produce and secrete cannabinoid synthase; b) a bioreactor containing a cannabinoid precursor in a first phase with a cannabinoid synthase in a second phase, c) a control mechanism configured to control a condition of the bioreactor, wherein the condition of the bioreactor influences a quantity formed of the first cannabinoid relative to a quantity formed of a second cannabinoid or a cannabinoid analog. In another embodiment, the method comprises contacting a cannabinoid precursor in a first phase with a cannabinoid synthase in a second phase. The first phase and the second phase, in some embodiments, are substantially immiscible or immiscible. In one embodiment, the cannabinoid synthase used in this disclosure comprises cannabidiolic acid (CBDA) synthase, tetrahydrocannabinolic acid (THCA) synthase, cannabichromenic acid (CBCA) synthase, or a combination thereof. With regard to THCA synthase and CBDA synthase, the cannabinoid precursor is a compound according to Formula I:

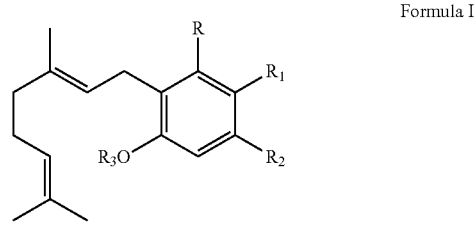

Formula I wherein R is selected from —OH, halogen, —SH, or a —NR$_a$R$_b$ group; R$_1$ is —H, —COOH, or —C(O)R$_a$, and R$_2$ is selected from the group consisting of —H, —C(O)R$_a$, —OR$_a$, an optionally substituted C$_1$-C$_{10}$ linear or branched alkylene, an optionally substituted C$_2$-C$_{10}$ linear or branched alkenylene, an optionally substituted C$_2$-C$_{10}$ linear or branched alkynylene, an optionally substituted C$_3$-C$_{10}$ aryl, an optionally substituted C$_3$-C$_{10}$ cycloalkyl, (C$_3$-C$_{10}$)aryl-(C$_1$-C$_{10}$)alkylene, (C$_3$-C$_{10}$)aryl-(C$_2$-C$_{10}$)alkenylene, and (C$_3$-C$_{10}$)aryl-(C$_1$-C$_{10}$)alkynylene. In one embodiment, R$_1$ and R$_2$ together with the carbon atoms to which they are bonded form a C$_5$-C$_{10}$ cyclic ring; R$_3$ is selected from the group consisting of H, —C(O)R$_a$, and C$_1$-C$_{10}$ linear or branched alkyl; and R$_a$ and R$_b$ are each independently —H, —OH, —SH, —NH$_2$, (C$_1$-C$_{10}$) linear or branched alkyl, or a $C_3$-$C_{10}$ cycloalkyl. In another embodiment, the cannabinoid precursor comprises cannabigerolic acid (CBGA), cannabigerovaniric acid (CBGVA), or the combination thereof.

The disclosure also relates to compositions, which can be used for, but are not limited to, synthesizing the cannabinoids. The compositions comprise (a) a cannabinoid precursor in a first phase; and (b) a cannabinoid synthase enzyme in a second phase, wherein the first phase and the second phase are substantially immiscible or immiscible. In some embodiments, the first phase comprises an organic solvent that is water-immiscible or substantially water-immiscible, and the second phase comprises an aqueous solvent or a mixture of an aqueous and a miscible organic solvent. In one embodiment, the cannabinoid synthase used in this disclosure comprises cannabidiolic acid (CBDA) synthase, tetrahydrocannabinolic acid (THCA) synthase, cannabichromenic acid (CBCA) synthase, or combination thereof. The cannabinoid precursor is a compound according to Formula I.

Also provided is an apparatus for the ex vivo manufacture of cannabinoids and analogs of cannabinoids.

BRIEF DESCRIPTION OF THE DRAWINGS

FIGS. 3A-3B shows the aqueous solutions with CBGVA (FIG. 3A) and CBGA (FIG. 3B) in aqueous buffer. At 0.05 g/L concentration, precipitation was observed in the CBGA solution (FIG. 3B), but not in the CBGVA solution.

FIG. 4 shows crystal formation after 24 hours in 0.1 g/L CBGVA solution in pH4.5 citrate buffer and 5% DMSO under phase contrast microscope with 400× magnification.

FIG. 7 shows the production of THCVA, while FIG. 8 shows the production of CBCVA. Ratios of THCVA:CBVCA at 168 hours are shown at FIG. 7B, and ratios of CBCVA:THCVA are shown in FIG. 8B.

FIGS. 10A-10B show the production of CBDVA, while FIGS. 11A-11B show the production of CBCVA. Ratios of CBDVA:CBCVA are shown in FIG. 10B, and ratios of CBCVA:CBDA are shown in FIG. 11B.

FIGS. 12A-12B, 13A-13B, 14A-14B, 15A-15B show effects of DMSO on CBGVA cyclization by THCA and CBDA synthases in a biphasic oil-aqueous system.

FIGS. 16 and 17 depict the activity of THCA synthase in biphasic oil-aqueous reactions with CBGVA as substrate. In those experiments, pH was optimized for formation of THCVA (FIG. 16) and CBCVA (FIG. 17), separately.

FIG. 22 shows the production of THCA, while FIG. 23 shows the production of CBCA. Ratios of THCA:CBCA at 168 hours are shown at FIG. 22B, and ratios of CBCA:THCA are shown in FIG. 23B.

FIG. 30 shows the total amount of cannabinoids produced.

FIGS. 32, 33A-33B, 34A-34B, 35A-35B show the kinetics of CBGA cyclization in the presence of different concentrations of methanol and DMSO in an aqueous reaction system. FIG. 32 shows the UV-HPLC trace (detection at 267 nm) of products in the reaction of CBGA cyclization catalyzed by CBDA synthase in the presence of 10% (v/v) MeOH after 2 hours (reaction products are marked by arrows). FIGS. 33A-33B show kinetics of CBGA conversion into CBDA (in relative units). FIGS. 34A-34B show kinetics of CBGA conversion into THCA (in relative units). FIG. 35A-35B show kinetics of CBGA conversion into CBCA (in relative units).

FIG. 50A shows the CBGVA concentration during the bioconversion reaction at various concentrations of THCA synthase in presence of dipentene and catalase. FIG. 50B shows the CBGVA concentration during the bioconversion reaction at various concentrations of DMSO in presence of catalase. FIG. 50C shows the concentrations of various cannabinoids after 48 hours of reaction at various concentrations of DMSO. FIG. 50D shows the scale-up bioconversion reaction (300 mL) with 3 g of CBGVA in the 100 mL dipentene organic phase (30 g/L). The aqueous phase contains 200 mL of pH 5.0 sodium citrate buffer, 10% DMSO with 5 g of THCA synthase (25 g/L), and 20 mg of catalase (0.1 g/L). FIG. 50E depicts CBCVA production in biphasic systems using different solvents and cosolvents. FIG. 50F shows the ratio of CBCVA:THCVA at 20 hours of reactions time in presence of dipentene along with DMSO and methanol.

FIG. 51A depicts the conversion to CBDVA in presence of dipentene and soybean oil. FIG. 51B shows the conversion to CBDVA in dipentene in presence of catalase or MeOH cosolvent. FIG. 51C shows the conversion to CBDVA in soybean oil in presence of catalase or MeOH cosolvent. FIG. 51D shows the conversion of CBGVA to the whole cannabinoid products (CBDVA, THCVA, and CBCVA) in dipentene with catalase or MeOH cosolvent. FIGS. 51E and 51F show the total cannabinoid production (CBDVA, THCVA, & CBCVA) in area percent over 144 hours in both biphasic soybean systems (FIG. 51E) and dipentene systems (FIG. 51F).

DETAILED DESCRIPTION

Figure 1A:
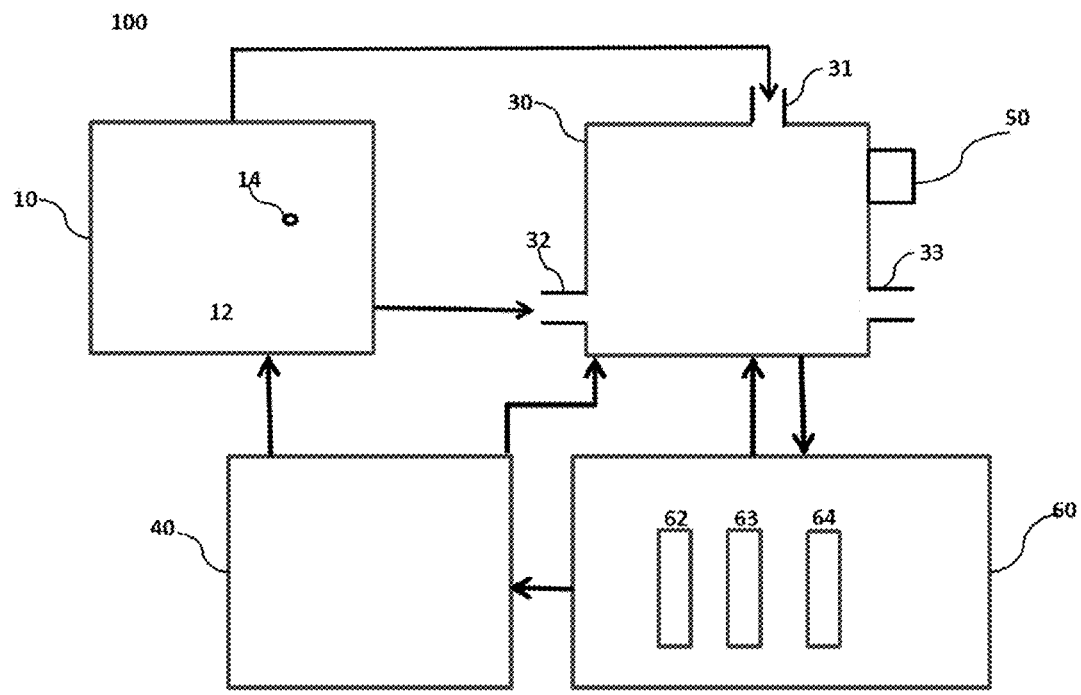
FIGS. 1A and 1B show an apparatus for synthesis of cannabinoids using biphasic production system and its communication mechanism.

It is to be understood that this invention is not limited to the particular methodology, protocols, cell lines, animal species or genera, compounds, polymers, and reagents described, as such may vary. It is also to be understood that the terminology used herein is for the purpose of describing particular embodiments only and is not intended to limit the scope of the present invention, which will be limited only by the appended claims.

As used herein, unless otherwise stated, the singular forms "a," "an," and "the" include plural reference. Thus, for example, a reference to "a compound" includes a plurality of compounds, and a reference to "a molecule" is a reference to one or more molecules.

All numerical designations, e.g., pH, temperature, time, concentration, amounts, and molecular weight, including ranges, are approximations which are varied (+) or (−) by 10%, 1%, or 0.1%, as appropriate. It is to be understood, although not always explicitly stated, that all numerical designations may be preceded by the term "about." It is also to be understood, although not always explicitly stated, that the reagents described herein are merely exemplary and that equivalents of such are known in the art.

The term "comprising" or "comprises" is intended to mean that the compositions and methods include the recited elements, but do not exclude others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than a trace amount of other ingredients and substantial method steps recited. Embodiments defined by each of these transition terms are within the scope of this invention.

The term "co-solvent" is used to mean a solvent that is added to the first phase or the second phase in an amount less than 50% of the total volume. In one embodiment, the co-solvent in the first phase is a water-immiscible solvent. In another embodiment, the co-solvent in the second phase is a water-miscible solvent.

The use of the term "or" in the claims is used to mean "and/or" unless explicitly indicated to refer to alternatives only, or the alternatives are mutually exclusive, although the disclosure supports a definition that refers to only alternatives and "and/or."

As used herein, the term "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, the term "precursor" refers to a compound that participates in a chemical reaction that produces another compound. In one embodiment, the cannabinoid precursor refers to a compound that participates in a reaction to produce another compound. For examples, CBGA is a precursor to THCA, CBDA, and CBCA. In another example, CBGVA is a precursor to THCVA, CBDVA, and CBCVA.

The term "cannabinoid product" or "cannabinoid compound" is intended to mean any simple or complex substance or compound of natural, semi-synthetic, or synthetic origin, which can act on the cannabinoid receptors of a subject. In some embodiments, the cannabinoid product is an agonist of the cannabinoid receptor. In some embodiments, the cannabinoid product is an antagonist of the cannabinoid receptor. In one embodiment, the cannabinoid product comprises phytocannabinoids, endogenous cannabinoids (endocannabinoids), bio-synthetic cannabinoids, or synthetic cannabinoids produced in laboratories. In one embodiment, the cannabinoid product comprises a pentyl side chain on the aromatic ring. Certain cannabinoids have a propyl side chain. In this application, this class of cannabinoids may be referred to as "varin."

Non-limiting cannabinoid products include tetrahydrocannabinol (THC), cannabidiol (CBD), olivetol, cannabinol (CBN), cannabigerol (CBG), cannabichromene (CBC), cannabicyclol (CBCL), nabilone, tetrahydrocannabinolic acid (THCA), cannabichromenic acid (CBCA), cannabicyclic acid (CBCLA), cannabigerolic acid (CBGA), cannabidiolic acid (CBDA), cannabinolic acid (CBNA), tetrahydrocannabivarin (THCV), cannabivarin (CBV), cannabidivarin (CBDV), cannabigerovarin (CBGV), cannabichromevarin (CBCV), cannabicyclovarin (CBCLV), cannabicyclovarinic acid (CBCLVA), cannabigerovarinic acid (CBGVA), tetrahydrocannabivarinic acid (THCVA), cannabichrome varinic acid (CBCVA), cannabidivarinic acid (CBDVA), as well as the prodrugs and pharmaceutically acceptable salts of these cannabinoids. Exemplary prodrugs include alkyl ethers, haloalkyl ethers, alkyl esters, haloalkyl esters, and aromatic esters, for example CBD difluoromethyl ether or CBD methyl ether.

Figure 2:
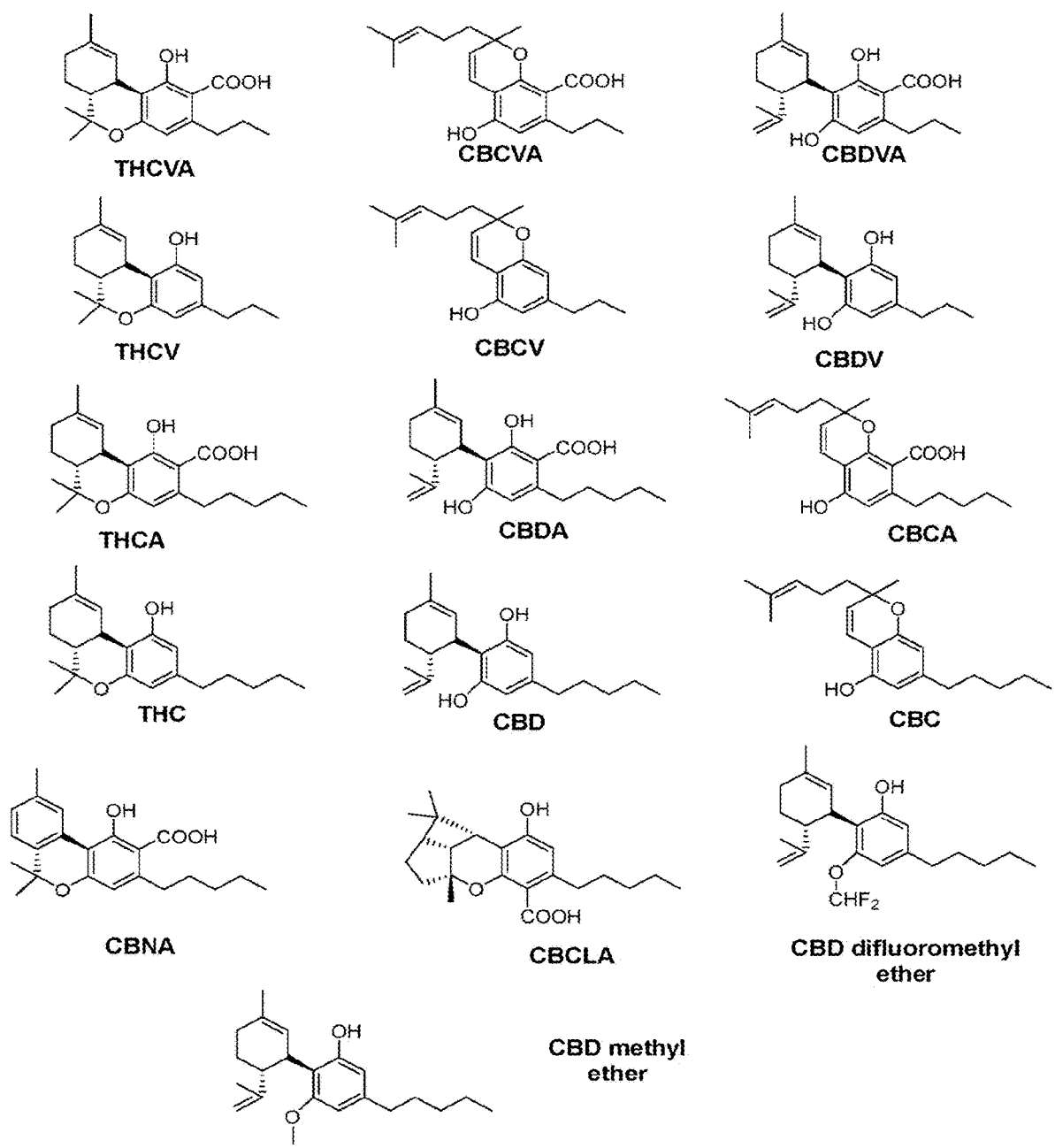
FIG. 2 shows chemical structures of cannabinoid compounds, including THCVA, CBDVA, CBCVA, THCV, CBCV, CBDV, THCA, CBDA, CBCA, THC, CBD, CBC, CBNA, CBCLA, CDB difluoromethyl ether, and CBD methyl ether.

As used herein, the term "cannabinoid varin compound" refers to cannabinoid compounds comprising a propyl side chain attached to an aromatic ring. In one embodiment, the cannabinoid varin compound is psychoactive. In another embodiment, the cannabinoid varin compound is non-psychoactive. Non-limiting examples of cannabinoid varin compounds include tetrahydrocannabivarin (THCV), cannabivarin (CBV), cannabidivarin (CBDV), cannabigerovarin (CBGV), cannabichromevarin (CBCV), cannabicyclovarin (CBCLV), cannabicyclovarinic acid (CBCLVA), cannabigerovarinic acid (CBGVA), tetrahydrocannabivarinic acid (THCVA), cannabichromevarinic acid (CBCVA), and cannabidivarinic acid (CBDVA), as well as natural or synthetic molecules that have a basic cannabinoid varin structure and are modified synthetically to provide a cannabinoid analog. The chemical structures of exemplary cannabinoids varin compounds are shown in FIG. 2.

As used herein, the term "biphasic" refers to a system for production of cannabinoids, which comprises two phases of solvents—a first phase and a second phase. A solvent is the substance in which a solid, liquid, or gas is dissolved. In one embodiment, the second phase comprises an aqueous solvent, while the first phase comprises a solvent that is water-immiscible with the aqueous solvent of the second phase. In some embodiments, the first phase forms the bottom or lower phase and the second phase forms the upper or top phase. In another embodiment, the second phase forms the bottom or lower phase and the first phase forms the upper or top phase.

In one embodiment, the first phase comprises one or more organic solvents that are water-immiscible or substantially water-immiscible. In one embodiment, when the composition is agitated prior to use, the mixture obtained has an opaque character. In one embodiment, the first and second phases may be layered with one phase on top of the other. In another embodiment, the phases may also be arranged in an alternative way, e.g., forming spherical or oval shapes droplets or microdroplets within the other phase.

Each of the first phase and the second phase comprise one or more solvents. In one embodiment, the one or more solvents comprise a co-solvent. In one embodiment, the co-solvent is an organic solvent that can contain one or more polar groups, such as —OH, —SH, —COOH, —C(O)R$_x$, or —C(O)OR$_x$, where R$_x$ is a (C$_1$-C$_5$) alkyl group. Exemplary co-solvents used in the bi-phasic system include without limitation, methanol, ethanol, iso-propanol, butanol, pentanol, pentane, hexane, heptane, pentene, 1,4-butane diol, dimethyl sulfoxide dimethyl acetamide, dimethyl formamide, small chain fatty acid, a medium chain fatty acid, myrcene, β-caryophyllene, limonene (dipentene), α-pinene, β-pinene, citral, carvone, myrcene, citronellol, eugenol, terpinene, menthol, terpineol, terpinolene, humulene, phytol, α-phellandrene, delta-3-carene, nerol, and linalool.

As used herein, the term "microdroplet" refers to a droplet having a volume in the range from about 1 picoliter to 1 microliter. In some embodiments, droplets with a volume of 1 nanoliter to 999 nanoliters may also be referred to as nanodroplets. In some embodiments, the microdroplet is formed within a biphasic system.

As used herein, the term "agitate" or "agitation" refers to mechanical movement, for example, rotating, vibrating, vortexing, swirling, shaking, ultrasonicating, stirring, or any movement that causes mixing. Mechanical movements include movements performed by hand or by a rotator.

As used herein, the term "water-immiscible solvent" refers to any non-aqueous or hydrophobic solvent which separates from solution into two distinct phases when mixed with water. The water-immiscible liquid is generally non-polar, with the non-limiting examples of the water-immiscible liquid including terpenes, sesquiterpenes, butanone, butyl acetate, heptane, hexane, toluene, cyclohexane, petroleum ether (60-80), petroleum ether (80-100), petroleum ether (100-120), dibutyl ether, dipentyl ether, hexadecane, tetrachloroethylene, 1,1,1 trichloroethane, mineral oil, vegetable oil, soybean oil, refined kerosene, diesel oil, paraffin oil, white spirit or aviation crude oil, oil of an oil-based paint, grease, solvent-born or solvent-free epoxy systems, thin film and powder coating, or other water-immiscible liquids well known in the art.

In some embodiments, the water-immiscible liquid comprises one or more of olive oil, sesame oil, castor oil, cotton-seed oil, soybean oil, linseed oil, hemp oil, butane, pentane, heptane, octane, isooctane, nonane, decane, terpenes, di-terpenes, tri-terpenes, myrcene, β-caryophyllene, limonene, terpeneol, and the combination thereof. In some embodiments, the water-immiscible solvent comprises acetaldehyde, acetic acid, acetone, acetonitrile, 1,2-butanediol, 1,3-butanediol, 1,4-butanediol, 2-butoxyethanol, butyric acid, diethanolamine, diethylenetriamine, dimethylformamide, dimethoxyethane, dimethyl sulfoxide, 1,4-dioxane, ethanol, ethylamine, ethylene glycol, formic acid, furfuryl alcohol, glycerol, methanol, methyl diethanolamine, methyl isocyanide, 1-propanol, 1,3-propanediol, 1,5-pentanediol, propanol, propanoic acid, propylene glycol, pyridine, tetrahydrofuran, and triethylene glycol.

As used herein, the term "immiscible" means a solvent or a substance (e.g., a compound, a molecule, a protein) is insoluble in a separate solvent. The term "substantially immiscible" means that only small amounts of the solvent or substance (e.g., a compound, a molecule, a protein) are soluble in a separate solvent. In one embodiment, the immiscible or substantial immiscible solvents, when mixed together, cause phase separation and form a liquid-liquid interface in between. The solubility between the two solvents can be measured by mass, weight, volume, or other unites. In one embodiment, the solubility between two substantially immiscible solvents at ambient temperatures (e.g., 15° C.~25° C.) is less than 10% by weight, less than 5% by weight, or less than 1% by weight. In one embodiment, the solubility between two substantially immiscible solvents at ambient temperatures (e.g., 15° C.~25° C.) is less than 10% by mass, less than 5% by mass, or less than 1% by mass.

For instance, the phrase "substantially immiscible" refers to a first solvent that is partially miscible or soluble in a second solvent in a range less than 10% by weight, mass, or volume.

For example, assuming there are two solvents (solvent 1 and solvent 2), the moe fraction of solvent 1 in solvent 2 is computed as follows:

$$\text{mole \%(solvent 1)} = \frac{\eta(\text{solvent 1})}{\eta(\text{solvent 1}) + \eta(\text{solvent 2})}$$

The mole fraction of solvent 2 in the solvent 1 is computed as follows:

$$\text{mole \%(solvent 2)} = \frac{\eta(\text{solvent 2})}{\eta(\text{solvent 1}) + \eta(\text{solvent 2})}$$

In one embodiment, an immiscible or substantially immiscible solvent refers to a solvent that is insoluble or substantially insoluble in water. In another embodiment, the immiscible solvent comprises a non-polar solvent.

The term "miscible" means a solvent or a substance that is soluble in a separate solvent. In one embodiment, the separate solvent is water. In one embodiment, the miscible solvent comprises a polar solvent.

As used herein, the term "organic solvent" refers to a hydrocarbon-based solvent. The organic solvent of this disclosure does not include hexane. In one embodiment, the organic solvent contains one or more polar groups. In some embodiments, the organic solvent is capable of dissolving a substance that has low solubility in water. In one embodiment, the organic solvents comprise one or more of olive oil, sesame oil, castor oil, cotton-seed oil, soybean oil, linseed oil, hemp oil, butane, pentane, heptane, octane, isooctane, nonane, decane, terpenes, di-terpenes, tri-terpenes, myrcene, β-caryophyllene, limonene, terpeneol, and the combination thereof. In another embodiment, the organic solvents comprises dimethyl sulfoxide (DMSO), dimethylacetamide (DMA), dimethylformamide (DMF), isopropyl alcohol, cyclodextrin, and methanol (MeOH), dimethyl isosorbide (DMI), glycerol, propylene glycol, hexylene glycol, diethylene glycol, propylene glycol n-alkanols, 1-menthol, dioxolane, ethylene glycol, other glycols, oleyl alcohol, alpha-hydroxy acids (e.g., lactic acid and glycolic acid), methyl dodecyl sulfoxide, dimethylacetamide, azone (1-dodecylazacycloheptan-2-one), 2-(n-nonyl)-1,3-dioxolane, alkanols, dialkylamino acetates, or the combination thereof. In one embodiment, the organic solvent comprises terpenes, di-terpenes, tri-terpenes, myrcene, β-caryophyllene, and combinations thereof. In one embodiment, the second phase of the biphasic system comprises the organic solvent.

As used herein, the term "terpene" refers to a class of organic compounds, derived biosynthetically from units of isoprene ($C_5H_8$) and to their variants, particularly oxygenated derivatives thereof (often called terpenoids). Non-limiting examples of terpenes include hemiterpenes (e.g., isoprene, prenol, and isovaleric acid), monoterpenes (e.g., myrcene, geraniol, limonene, terpineol, pinene (α- and β-pinene), menthol, thymol, carvacrol, camphor, borneol, and eucalyptol), sesquiterpenes (e.g., humulene, beta-caryophylene, neurolidol, farnesenes, and farnesol), diterpenes (e.g., cafestol, kahweol, cembrene, and taxadiene), sesterterpenes (e.g., geranylfarnesol), triterpenes, sesquarterpenes (e.g., ferrugicadiol and tetraprenylcurcumene), tetraterpenes (e.g., acyclic lycopene, the monocyclic gamma-carotene, and the bicyclic alpha- and beta-carotenes), polyterpenes, and norisoprenoids. Limonene is also called dipentene. In one embodiment, terpenes have 10 carbon atoms or 15 carbon atoms (monoterpenes and sesquiterpenes) and oxygenated derivatives thereof. In another embodiment, terpene mixtures of the invention can contain small amounts, i.e., less than 2% by weight or less than 1% by weight of terpenes other than monoterpenes and sesquiterpenes and oxygenated derivatives thereof. In one embodiment, the terpene is dipentene.

As used herein, the term "peroxide scavenger" refers to a component or a chemical that is capable of removing or reducing peroxide or decreasing the undesirable effects of peroxide. Non-limiting examples of peroxide scavengers include catalase, glutathione peroxidases (GPx), thioredoxin-assisted peroxidases (Prx), Sodium pyruvate, and N,N'-dimethylthiourea (DMTU). In one embodiment, the peroxide scavenger comprises catalase.

The terms "lyophilized" and "lyophilization" as used interchangeably herein, refer to a freeze-dried process known in the art. In some embodiments, during the process a material (e.g., an enzyme) is first frozen and then the ice or frozen solvent is removed by sublimation in a vacuum environment. An excipient may be included in pre-lyophilized formulations to enhance stability of the lyophilized product upon storage.

The terms "purification" or "purifying" as used interchangeably herein, refer to increasing the degree of purity of a substance of interest (e.g., an enzyme, a protein, or a compound), from a sample comprising the substance of interest. Methods for purification are well known in the art. Non-limiting examples of purification methods include silica gel column chromatography, size exclusion chromatography, hydrophobic interaction chromatography, ion exchange chromatography (e.g., cation and anion exchange chromatographies), free-flow-electrophoresis, HPLC (high performance liquid chromatography), and differential precipitation. In one embodiment, Sepharose SP Fast Flow resin (GE healthcare life science) is used to purify the substance of interest (e.g., an enzyme).

The terms "recover" or "recovery" refer to a process of isolating a product from a reaction or a synthesis process for the product. The product can be a compound, a protein, a nucleotide, or a lipid. In one embodiment, the product recovered from the synthesis process is a cannabinoid compound. The methods to recover the end products are well known in the art. Non-limiting examples of recovery methods include chromatography (e.g., silica gel chromatography or HPLC), activated charcoal treatment, filtration, distillation, precipitation, drying, chemical derivation, or combinations of these methods.

The term "analog" refers to a compound that is structurally related to naturally occurring cannabinoids, but its chemical and/or biological properties may differ from naturally occurring cannabinoids. In some embodiments, analog or analogs refer to compounds that may not exhibit one or more unwanted side effects of a naturally occurring cannabinoid. Analog also refers to a compound that is derived from a cannabinoid by chemical, biological, or a semi-synthetic transformation of the cannabinoid. The cannabinoid can be a naturally occurring, biosynthetic, or a chemically synthesized compound.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, pegylated derivatives of a parent compound, and N-oxides of a parent compound.

Unless otherwise indicated, "stereoisomer" means one stereoisomer of a compound that is substantially free of other stereoisomers of that compound. Thus, a single stereoisomer of a compound will be substantially free of the other stereoisomers. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example, greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

Enzymes are very specific with respect to the type of chemical reactions they catalyze and the nature and type of substrates that are involved in these reactions. Enzymes also exhibit a high level of stereospecificity, regiospecificity, and chemoselectivity. It was therefore unexpected, when the present inventors observed that the purity and efficiency of producing cannabinoid products with the methods of this disclosure can vary, depending on the conditions under which the cannabinoid synthase enzymes catalyze the conversion of a substrate (or precursor) to a cannabinoid product.

Accordingly, the effects of temperature, pH, different solvents, ionic strength, and/or incubation times on the distribution ratio of cannabinoid products (e.g., the ratio of THCVA to CBCVA, THCA to CBCA, or CBDVA to THCVA and CBCVA) are provided in this disclosure. For example, the effect of solvent on cannabinoid product distribution ratio is evaluated.

Cannabinoids are lipophilic in nature and are poorly solubilized in aqueous solvents. The poor solubility of cannabinoids in aqueous solvent has prevented the development of ex vivo enzyme catalyzed methodologies for the synthesis of cannabinoids and cannabinoid analogs. The present invention addresses these issues by using a biphasic solvent system. Accordingly, the enzyme substrates, namely CBGA or CBGVA are dissolved in a water-immiscible or substantially water-immiscible solvent while an appropriate cannabinoid synthase enzyme is dissolved in an aqueous buffer. In one embodiment, the water-immiscible or substantially water-immiscible solvent is an organic solvent.

In one embodiment, the cannabinoid precursor is a compound of Formula I:

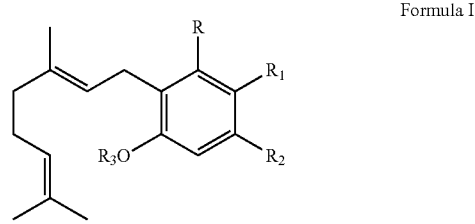

Formula I wherein R is selected from —OH, halogen, —SH, or a —NR$_a$R$_b$ group; R$_1$ and R$_2$ are each independently selected from the group consisting of —H, —C(O)R$_a$, —OR$_a$, an optionally substituted C$_1$-C$_{10}$ linear or branched alkylene, an optionally substituted C$_2$-C$_{10}$ linear or branched alkenylene, an optionally substituted C$_2$-C$_{10}$ linear or branched alkynylene, an optionally substituted C$_3$-C$_{10}$ aryl, an optionally substituted C$_3$-C$_{10}$ cycloalkyl, (C$_3$-C$_{10}$)aryl-(C$_1$-C$_{10}$)alkylene, (C$_3$-C$_{10}$)aryl-(C$_2$-C$_{10}$)alkenylene, and (C$_3$-C$_{10}$)aryl-(C$_1$-C$_{10}$)alkynylene, or R$_1$ and R$_2$ together with the carbon atoms to which they are bonded form a C$_5$-C$_{10}$ cyclic ring; R$_3$ is selected from the group consisting of H, —C(O)R$_a$, and C$_1$-C$_{10}$ linear or branched alkyl; and R$_a$ and R$_b$ are each independently —H, —OH, —SH, —NH$_2$, (C$_1$-C$_{10}$) linear or branched alkyl, or a C$_3$-C$_{10}$ cycloalkyl.

In one embodiment, the cannabinoid precursor is a compound of Formula II:

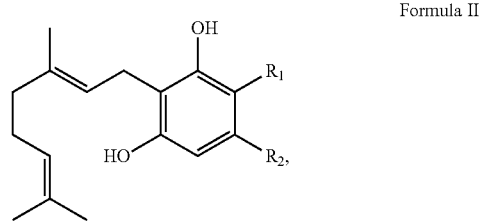

Formula II wherein R$_1$ is H or —COOH and R$_2$ is a linear or branched CH$_3$, C$_2$H$_5$, C$_3$H$_7$, C$_4$H$_9$, C$_5$H$_{10}$, C$_6$H$_{13}$, C$_7$H$_{15}$ or C$_8$H$_{17}$ group. In another embodiment, R$_2$ is a linear C$_3$H$_7$ or C$_5$H$_{10}$. In another embodiment, the cannabinoid precursor is CBGVA, CBGA, or their derivatives or analogs.

The present inventors surprisingly found that THCA synthase and CBDA synthase retained their catalytic activity in a biphasic system comprising a first phase and a second phase. The second phase is a distinct aqueous phase. The first phase is water-immiscible with the aqueous phase of the second phase. Each of the first phase and second phase can comprise one or more solvents. Illustrative examples of such solvents are dimethyl sulfoxide (DMSO), dimethyl formamide (DMF), dimethyl acetamide (DMA), isopropyl alcohol, (IPA), methanol and cyclodextrin.

Cannabinoid compounds encompassed by the invention comprise pentyl chain and propyl chain cannabinoids. In one embodiment, the cannabinoid compound is a pentyl chain cannabinoid. Non-limiting examples of the cannabinoid compounds include tetrahydrocannabinol (THC), cannabidiol (CBD), olivetol, cannabinol (CBN), cannabigerol (CBG), cannabichromene (CBC), cannabicyclol (CBCL), nabilone, tetrahydrocannabinolic acid (THCA), cannabichromenic acid (CBCA), cannabicyclol acid (CBCLA), cannabigerolic acid (CBGA), cannabidiolic acid (CBDA), cannabinolic acid (CBNA), as well as the prodrugs and pharmaceutically acceptable salts of these cannabinoids. The prodrugs include but are not limited to alkyl ethers, haloalkyl ethers, alkyl esters, haloalkyl esters, and polyethylene glycol ethers and esters of cannabinoids. In one embodiment, the prodrug of CBD is a CBD difluoromethyl ether or a CBD methyl ether compound. In certain embodiments, the cannabinoid compound is nabilone, dronabinol, anandamide as well as natural or synthetic molecules that have a basic cannabinoid structure and are modified synthetically to provide a cannabinoid analog.

In another embodiment, the cannabinoid compound is a cannabinoid having a propyl side chain attached to an aromatic ring, also known as a "varin". While varins are present in the cannabis plant, their natural abundance in plant tissue is low. For example, the natural abundance of several varin compounds in plant tissue is between 0.5%-1.5%. By using a biphasic solvent system, the present invention permits synthesis of several varin compounds in high volumetric yields. Non-limiting examples of varin compounds synthesized using the biphasic solvent system and methods of the invention include tetrahydrocannabivarin (THCV), cannabivarin (CBV), cannabidivarin (CBDV), cannabigerovarin (CBGV), cannabichrome varin (CBCV), cannabicyclovarin (CBCLV), cannabicyclovarinic acid (CBCLVA), cannabigerovarinic acid (CBGVA), tetrahydrocannabivarinic acid (THCVA), cannabichromevarinic acid (CBCVA), cannabidivarinic acid (CBDVA), as well as natural or synthetic molecules that have a basic cannabinoid varin structure and are modified synthetically to provide a cannabinoid analog. FIG. 2 shows the chemical structures of some cannabinoid compounds.

Methods of Producing Cannabinoid Products

One aspect of the invention provides a method of producing a cannabinoid product. In some embodiment, the cannabinoid product comprises pentyl chain or propyl chain cannabinoids. In one embodiment, the cannabinoid product comprises a cannabinoid varin.

In one embodiment, the method for producing a cannabinoid product comprises contacting a cannabinoid precursor in a first phase with a cannabinoid synthase in a second phase. The cannabinoid precursor is a substrate of a cannabinoid synthase.

In one embodiment, the cannabinoid precursor is a compound of Formula I:

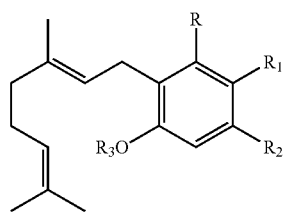

Formula I wherein R is selected from —OH, halogen, —SH, or a —NR$_a$R$_b$ group; R$_1$ and R$_2$ are each independently selected from the group consisting of —H, —C(O)R$_a$, —OR$_a$, an optionally substituted C$_1$-C$_{10}$ linear or branched alkylene, an optionally substituted C$_2$-C$_{10}$ linear or branched alkenylene, an optionally substituted C$_2$-C$_{10}$ linear or branched alkynylene, an optionally substituted C$_3$-C$_{10}$ aryl, an optionally substituted C$_3$-C$_{10}$ cycloalkyl, (C$_3$-C$_{10}$)aryl-(C$_1$-C$_{10}$)alkylene, (C$_3$-C$_{10}$)aryl-(C$_2$-C$_{10}$)alkenylene, and (C$_3$-C$_{10}$)aryl-(C$_1$-C$_{10}$)alkynylene, or R$_1$ and R$_2$ together with the carbon atoms to which they are bonded form a C$_5$-C$_{10}$ cyclic ring; R$_3$ is selected from the group consisting of H, —C(O)R$_a$, and C$_1$-C$_{10}$ linear or branched alkyl; and R$_a$ and R$_b$ are each independently —H, —OH, —SH, —NH$_2$, (C$_1$-C$_{10}$) linear or branched alkyl, or a C$_3$-C$_{10}$ cycloalkyl.

In one embodiment, the cannabinoid precursor is a compound of formula II:

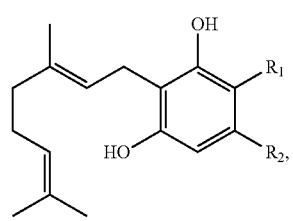

Formula II wherein R$_1$ is H or —COOH and R$_2$ is a linear or branched CH3, C$_2$H$_5$, C$_3$H$_7$, C$_4$H$_9$, C$_5$H$_{10}$, C$_6$H$_{13}$, C$_7$H$_{15}$, or C$_8$H$_{17}$ group. In another embodiment, R$_2$ is a linear C$_3$H$_7$ or C$_5$H$_{10}$. In another embodiment, the cannabinoid precursor is CBGVA, CBGA or derivatives or analogs of CBGA and CBGVA.

In one embodiment, the first phase comprise an organic solvent and the second phase comprises an aqueous solvent. In one embodiment, the first phase and the second phase are substantially immiscible or immiscible, and thus the method of this disclosure comprises a biphasic process.

In some embodiments, the methods further comprise agitating the organic solvent to form micro-droplets within the aqueous solution, wherein at least one micro-droplet comprises the cannabinoid precursor. In one embodiment, the cannabinoid precursor is CBGVA, CBGA, and their derivative or analog.

The size of the microdroplet can vary depending on the solvents, the method or orientation of agitation, or the composition within each solvent. In some embodiments, the microdroplet has a volume ranging less than 1 picoliter, between 1 picoliter to 1 microliter, or above 1 microliter. The duration of agitation can vary as well. In one embodiment, the duration of agitation is less than 5 seconds, 10 seconds, 1 minute, 10 minutes, 30 minutes, 1 hour, 2 hours, 10 hours, or 24 hours. In some embodiments, the duration of agitation is more than 24 hours.

In one embodiment, the first phase comprises an organic solvent, which can be polar or non-polar. In another embodiment, the organic solvent is substantially water-immiscible. In some embodiments, the first phase is capable of dissolving a substance that has low solubility in water. In one embodiment, the first phase comprises one or more of olive oil, sesame oil, castor oil, cotton-seed oil, soybean oil, linseed oil, hemp oil, butane, pentane, heptane, octane, isooctane, nonane, decane, terpenes, di-terpenes, tri-terpenes, myrcene, β-caryophyllene, limonene, and terpeneol. In another embodiment, the terpene comprises one of more of hemiterpene, monoterpene, sesquiterpene, diterpene, sesterterpene, triterpene, sesquarterpene, tetraterpene, polyterpene, and norisoprenoid. In another embodiment, the terpene comprises one or more of di-terpenes, tri-terpenes, myrcene, β-caryophyllene, limonene, pinene, and linalool. In one embodiment, the first phase may comprise fatty acids or fatty acid esters.

In another embodiment, the first phase comprises one or more of mineral oil, vegetable oil, refined kerosene, diesel oil, paraffin oil, or other water-immiscible liquids well known in the art. In one embodiment, the first phase further comprises, acetic acid, acetone, acetonitrile, 1,2-butanediol, 1,3-butanediol, 1,4-butanediol, 2-butoxyethanol, butyric acid, diethanolamine, diethylenetriamine, dimethylformamide, dimethoxyethane, dimethyl sulfoxide, 1,4-dioxane, ethanol, ethylamine, ethylene glycol, formic acid, furfuryl alcohol, glycerol, methanol, methyl diethanolamine, methyl isocyanide, 1-propanol, 1,3-propanediol, 1,5-pentanediol, propanol, propanoic acid, propylene glycol, pyridine, tetrahydrofuran, and triethylene glycol. In another embodiment, the first phase comprises terpene. In another embodiment, terpene comprises one of more of hemiterpene, monoterpene, sesquiterpene, diterpene, sesterterpene, triterpene, sesquarterpene, tetraterpene, polyterpene, and norisoprenoid. In another embodiment, the terpene comprises one or more of di-terpenes, tri-terpenes, myrcene, β-caryophyllene, limonene (dipentene), α-pinene, β-pinene, citral, carvone, myrcene, citronellol, eugenol, terpinene, menthol, terpineol, terpinolene, humulene, phytol, α-phellandrene, delta-3-carene, nerol, and linalool. In one embodiment, terpenes have 10 carbon atoms or 15 carbon atoms (monoterpenes and sesquiterpenes) and oxygenated derivatives thereof. In another embodiment, terpene mixtures of the invention can contain small amounts, i.e., less than 2% by weight or less than 1% by weight of terpenes other than monoterpenes and sesquiterpenes and oxygenated derivatives thereof. In another embodiment, the first phase comprises fatty acids, fatty acid esters, or the combination thereof.

The first phase may contain a co-solvent. The amount of co-solvent in the first phase depends on the composition, the concentration, pH, temperature, or other conditions. In one embodiment, the amount of co-solvent within the first phase is less than 50%, in the range between about 5% and about 49%, between about 10% and about 49%, between about 20% and about 49%, between about 30% and about 49%, between about 40% and about 49%, or between about 45% and about 49%. In one embodiment, the amount of co-solvent is between about 30% and about 49%. In another embodiment, the amount of co-solvent is between about 10% and about 25%, or 2% to 15%.

In another embodiment, the solvent of the first phase comprises soybean oil. In some embodiments, the amount of soybean oil is greater than 50%, in the range between about 51% and about 90%, between about 60% and about 80%, between about 70% and about 79%, between about 80% and about 90%, between about 90% and about 100%, or between about 50% and about 99% of the organic solvent. In another embodiment, the amount of soybean oil is between about 50% and about 60%. In some embodiments, the amount of soybean oil is about 90%.

In another embodiment, the organic solvent of the first phase comprises terpene. In some embodiments, the amount of terpene is greater than 50%, in the range between about 50% and about 90%, between about 60% and about 80%, between about 70% and about 79%, between about 80% and about 90%, between about 90% and about 100%, or between about 50 and about 55% of the organic solvent.

In another embodiment, the organic solvent of the first phase comprises limonene (or dipentene). In some embodiments, the amount of limonene is greater than 50%, in the range between about 50% and about 90%, between about 60% and about 80%, between about 70% and about 79%, between about 80% and about 90%, between about 50% and about 60%, or between about 55% and 65% of the organic solvent.

The enzymatic efficiency of cannabinoid synthase (e.g., THCA synthase or CBDA synthase) can be affected by the types and concentrations of co-solvent in the second phase that comprises an aqueous solvent. Thus, in one embodiment, the second phase comprises an aqueous miscible co-solvent. The aqueous miscible co-solvent, in some embodiments, comprises one or more of dimethyl sulfoxide (DMSO), dimethylacetamide (DMA), dimethylformamide (DMF), ethanol, isopropyl alcohol, cyclodextrin, peroxide scavenger, and methanol (MeOH), and the combination thereof. In some embodiments, the amount of the aqueous miscible co-solvent in the second phase is less than 0.1%, between about 0.1% and about 49% (w/v), about 1% and about 49%, about 5% and about 49%, or about 10% and about 49%, or about 20% and about 49%, about 30% and about 49% of the aqueous solution. In some embodiments, the amount of the aqueous miscilble co-solvent in the second phase is above 0.1%, 1%, 10%, 20%, 30%, 40%, or 49%

In some embodiments, the second phase comprises dimethyl sulfoxide (DMSO) as a water miscible co-solvent in an amount less than 0.1%, between about 0.1% and about 49% (w/v), about 1% and about 49%, about 5% and about 49%, or about 10% and about 49%, or about 20% and about 49%, or about 30% and about 49% of the aqueous solution. In one embodiment, the amount of DMSO in the second phase is above 0.1%, 1%, 10%, 20%, 30%, 40%, or 49%. In another embodiment, the second phase comprises DMSO in an amount between about 1% and about 20% of the aqueous solution. In one embodiment, the amount of DMSO is between about 10% and about 20%. In another embodiment, the amount of DMSO is about 20%.

In one embodiment, the second phase comprises water miscible co-solvent methanol (MeOH) in an amount less than 0.1%, between about 0.1% and about 49% (w/v), about 1% and about 49%, about 5% and about 49%, or about 10% and about 49%, or about 20% and about 49%, or about 30% and about 49% of the aqueous solution. In one embodiment, the amount of MeOH in the second phase is above 0.1%, 1%, 10%, 20%, 30%, 40%, or 49%. In another embodiment, the second phase comprises MeOH in an amount between about 1% and about 20% of the aqueous solution. In a different embodiment, the amount of MeOH is between about 10% and about 20%. In a different embodiment, the amount of MeOH is between about 1% and about 6%.

In one embodiment, the second phase comprises water miscible co-solvent dimethylacetamide (DMA) in an amount less than 0.1%, between about 0.1% and about 49% (w/v), about 1% and about 49%, about 5% and about 49%, or about 10% and about 49%, or about 20% and about 49%, or about 30% and about 49% of the aqueous solvent. In one embodiment, the amount of DMA is above 0.1%, 1%, 10%, 20%, 30%, 40%, or 49%. In another embodiment, the second phase comprises DMA in an amount between about 1% and about 20% of the aqueous solvent. In a different embodiment, the amount of DMA is between about 10% and about 20%. In a different embodiment, the amount of DMA is between about 1% and about 6%.

Surprisingly, Applicant discovered that inclusion of a peroxide scavenger increased the enzymatic activity of cannabinoid synthase. In one embodiment, the peroxide scavenger comprises one or more of catalase, glutathione peroxidases (GPx), thioredoxin-assisted peroxidases (Prx), Sodium pyruvate, and N,N'-dimethylthiourea (DMTU). In another embodiment, the peroxide scavenger is catalase. In one embodiment, the amount of the peroxide scavenger in the aqueous solution is between about 0.001% and about 0.1%, about 0.005% and about 0.05%, or about 0.01% and about 0.03% (w/v). In one embodiment, the amount of peroxide scavenger is about 0.01%. In another embodiment, the amount of catalase in the aqueous solvent is between about 0.001% and about 0.1%, about 0.005% and about 0.05%, or about 0.01% and about 0.03% (w/v). In another embodiment, the amount of catalase is about 0.01% of the aqueous solution.

The inventors were surprised to observe that the ratio of cannabinoid and the low abundance of varin compounds is altered by the pH of the aqueous phase that contains the cannabinoid synthase. In one embodiment, the pH of the aqueous solution ranges from about 3.5 to about 10.0, from about 3.5 to about 9, from about 4 to about 8, or from about 5.5 to about 7.5. In one embodiment, the pH value ranges from about 3.5 to about 9.0. In one embodiment, the pH value ranges from about 4.5 to about 7.5. Alternatively, the pH value ranges from about 5.5 to about 7.5. In some embodiments, the pH value ranges from about 5.0 to about 6.5. In one embodiment, the pH value is about 7.5. In another embodiment, the pH value is about 5.5. In yet another embodiment, the pH value is about 4.5.

The amount of a water miscible organic co-solvent can affect the production of cannabinoid compounds. In some embodiments, the aqueous solution comprises DMSO in a range between about 1% and about 30%, about 2% and about 20%, or about 5% and about 10% of the aqueous solution, wherein the pH value of the aqueous solution is between about 3 and about 9, about 4 and about 8, or about 5.5 and about 7.5. In some embodiments, the aqueous solution comprises DMSO in a range between about 5% and about 10% of the aqueous solution, wherein the pH value of the aqueous solution is between about 5.5 and about 7.5. In one embodiment, the aqueous solution comprises DMSO in an amount of about 5%, wherein the pH value of the aqueous solution is about 5.5. In another embodiment, the aqueous solvent comprises DMSO in an amount of about 10%, wherein the pH value of the aqueous solution is about 7.5.

In one embodiment, the volume ratio of the first phase to the second phase is from about 1:9 to about 9:1; from about 1:8 to about 8:1; from about 1:7 to about 7:1; from about 1:6 to about 6:1; from about 1:5 to about 5:1; from about 1:4 to about 4:1; from about 1:3 to about 3:1; or from about 1:2 to about 2:1. In one embodiment, the volume ratio is from about 1:9 to about 9:1. In another embodiment, the volume ratio is from about 1:2 to about 2:1.

The methods of this disclosure use a cannabinoid synthase as catalyst for synthesizing the cannabinoid compound. In one embodiment, the cannabinoid synthase comprises cannabidiolic acid synthase (CBDA synthase), a tetrahydrocannabinolic acid synthase (THCA synthase), or a cannabichromene acid synthase (CBCA synthase). In one embodiment, the cannabinoid synthase comprises CBDA synthase or THCA synthase. In one aspect of the invention, the cannabinoid synthase is dissolved in an aqueous phase. The cannabinoid synthase can be purified from plant (e.g., *C. sativa*). The synthase can also be produced in either eukaryotic or prokaryotic cells, e.g., *E. coli*, yeast, baculovirus hosts, mammalian cells, algae, tobacco plant cells in culture, or insect cells. The methods for expressing recombinant cannabinoid synthases are disclosed in WO2014134281, which is incorporated by reference in its entirety. In one embodiment, the cannabinoid synthase used for the method can be in its crude form or its purified form before dissolving in a solvent.

In another embodiment, the cannabinoid synthase (e.g., CBDA synthase or THCA synthase) is secreted into the culture medium in which the eukaryotic or prokaryotic cells are grown. For example, the coding sequence of the gene coding for the cannabinoid biosynthetic enzyme is operably linked to a secretion signal. For a yeast (e.g., *Pichia*), the signal sequence could be an alpha factor secretion signal. After the cannabinoid biosynthetic enzyme is secreted into the yeast growth medium, the yeast cells are removed and the growth medium is lyophilized (freeze dried) following filtration of the growth medium containing the cannabinoid synthase enzyme using a 10K molecular weight filter. The methods for expressing recombinant THCA synthase and CBDA synthase are described in WO2014134281, which is incorporated by reference in its entirety. Recovering enzyme in the lyophilized medium resulted in about 4% of the lyophilized medium comprising THCA synthase or CBDA synthase. Accordingly, in the working examples contained herein, if 100 grams of lyophilized medium was used as the technical grade enzyme, the medium contained about 4 grams of either THCA synthase or CBDA synthase.

The concentration of the synthases can vary based on the concentrations of substrates, the reaction conditions, or the target products. In one embodiment, the cannabinoid synthase used is a purified synthase. Without being bound by a theory, the requisite concentrations of purified synthase are normally less than those of crude synthase. In one embodiment, the concentration of the synthase in the aqueous solution is at least 0.1 mg/mL, 0.5 mg/mL, 1 mg/mL, 2 mg/mL, 5 mg/mL, 10 mg/mL, 32 mg/mL, 50 mg/mL, or 100 mg/mL. In another embodiment, the concentration of the synthase in the aqueous solution is at least 5 mg/mL. In another embodiment, the concentration of the synthase in the aqueous solution is at least 32 mg/mL. In one embodiment, the concentration of the purified synthase in the aqueous solution is at least 50 µg/mL. In some embodiments, the concentration of the purified synthase in the aqueous solution is at least 200 µg/mL.

In some embodiments, the concentration of cannabinoid precursor in the organic solvent is at least about 0.1 mg/mL, 1 mg/mL, 10 mg/mL, about 50 mg/mL, about 100 mg/mL, about 150 mg/mL, about 200 mg/mL, about 250 mg/mL, or about 300 mg/mL. In one aspect of this invention, the concentration of cannabinoid precursor in the organic solvent is between about 0.1 mg/mL and about 250 mg/mL, about 1 mg/mL and 200 mg/mL, about 20 mg/mL and about 150 mg/mL, or about 50 mg/mL and about 100 mg/mL. In some embodiment, the cannabinoid precursor is CBGA, CBGVA, or their derivatives or analogs.

The progress of the reaction can be monitored periodically or continuously. For example, the decrease in the concentration of cannabinoid precursor (e.g., CBGVA and CBGA) can be monitored to signal termination of synthesis. Alternatively, reaction progress is monitored by monitoring the formation of a cannabinoid, for example spectrophotometrically. Once the synthesis is terminated, the cannabinoid product thus produced can be readily recovered from the medium using standard solvent extraction or chromatographic purification methods. Thus, the methods of this disclosure further comprise recovering the cannabinoid composition or product.

In one embodiment, the recovered cannabinoid product comprises a cannabinoid varin compound (propyl side chain cannabinoid), which include one or more of tetrahydrocannabivarin (THCV), cannabivarin (CBV), cannabidivarin (CBDV), cannabigerovarin (CBGV), cannabichrome varin (CBCV), cannabicyclovarin (CBCLV), cannabicyclovarinic acid (CBCLVA), cannabigerovarinic acid (CBGVA), tetrahydrocannabivarinic acid (THCVA), cannabichromevarinic acid (CBCVA), cannabidivarinic acid (CBDVA), cannabichrome varinic acid (CBCVA), cannabidivarinic acid (CBDVA), or its analogs or derivatives. In one embodiment, the recovered cannabinoid product comprises THCVA, CBCVA, or both. In another embodiment, the recovered cannabinoid product comprises CBDVA, CBCVA, and optionally THCVA.

In one embodiment, the recovered cannabinoid product is a pentyl chain cannabinoid, which includes one or more of THC, CBD, CBN, CBG, CBC, CBCL, nabilone, THCA, CBCA, CBCLA, CBGA, CBDA, CBNA, and their derivatives, analogs, prodrugs, or any natural or synthetic molecules that have a basic cannabinoid structure and are modified synthetically. In one embodiment, the recovered cannabinoid product comprises THCA, CBCA, or both. In another embodiment, the recovered cannabinoid product comprises CBDA, CBCA, or optionally THCA. Neutral forms of the cannabinoids (e.g., THC, CBD, CBC, THCV, CBDV, CBG, and CBGV) are the result of non-enzymatic decarboxylation by exposure to, for example: heat, light, and pH.

The methods of recovering the cannabinoid products from the disclosed reaction are disclosed in WO2014134281, which is incorporated by reference in its entirety. Non-limiting examples of recovery methods include chromatography (e.g., HPLC or silica gel), activated charcoal treatment, filtration, distillation, precipitation, drying, chemical derivation, or combinations of these methods.

Composition

Another aspect of the disclosure relates to a composition that can be used for synthesizing the cannabinoid compounds, their analogs or derivatives. In one aspect of the invention, the composition comprises (a) a cannabinoid precursor in a first phase; and (b) a cannabinoid synthase in a second phase.

In one embodiment, the cannabinoid precursor is a compound of Formula I:

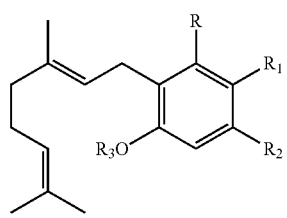

Formula I wherein R is selected from —OH, halogen, —SH, or a —NR$_a$R$_b$ group; R$_1$ and R$_2$ are each independently selected from the group consisting of —H, —C(O)R$_a$, —OR$_a$, an optionally substituted C$_1$-C$_{10}$ linear or branched alkylene, an optionally substituted C$_2$-C$_{10}$ linear or branched alkenylene, an optionally substituted C$_2$-C$_{10}$ linear or branched alkynylene, an optionally substituted C$_3$-C$_{10}$ aryl, an optionally substituted C$_3$-C$_{10}$ cycloalkyl, (C$_3$-C$_{10}$)aryl-(C$_1$-C$_{10}$)alkylene, (C$_3$-C$_{10}$)aryl-(C$_2$-C$_{10}$)alkenylene, and (C$_3$-C$_{10}$)aryl-(C$_1$-C$_{10}$)alkynylene, or R$_1$ and R$_2$ together with the carbon atoms to which they are bonded form a C$_5$-C$_{10}$ cyclic ring; R$_3$ is selected from the group consisting of H, —C(O)R$_a$ and C$_1$-C$_{10}$ linear or branched alkyl; and R$_a$ and R$_b$ are each independently —H, —OH, —SH, —NH$_2$, (C$_1$-C$_{10}$) linear or branched alkyl, or a C$_3$-C$_{10}$ cycloalkyl.

In one embodiment, the cannabinoid precursor is a compound of Formula II:

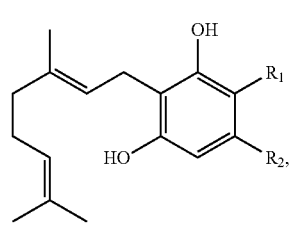

Formula II wherein R$_1$ is H or —COOH and R$_2$ is a linear or branched CH$_3$, C$_2$H$_5$, C$_3$H$_7$, C$_4$H$_9$, C$_5$H$_{10}$, C$_6$H$_{13}$, C$_7$H$_{15}$ or C$_8$H$_{17}$ group. In another embodiment, R$_2$ is a linear C$_3$H$_7$ or C$_5$H$_{10}$. In another embodiment, the cannabinoid precursor is CBGA, CBGVA, or their derivatives or analogs. In some embodiment, the cannabinoid precursor is CBGA. In another embodiment, the cannabinoid precursor is CBGVA.

In one embodiment, the first phase comprises an organic solvent and the second phase comprises an aqueous solvent. In one embodiment, the organic solvent is water-immiscible or substantially water-immiscible.

In some embodiments, the organic solvent is capable of dissolving a substance that has low solubility in water. The organic solvent may be polar or non-polar. In one embodiment, the first phase comprises one or more of olive oil, sesame oil, castor oil, cotton-seed oil, soybean oil, linseed oil, hemp oil, butane, pentane, heptane, octane, isooctane, nonane, decane, terpenes, di-terpenes, tri-terpenes, myrcene, β-caryophyllene, limonene, and terpeneol. In another embodiment, terpene comprises one of more of hemiterpene, monoterpene, sesquiterpene, diterpene, sesterterpene, triterpene, sesquarterpene, tetraterpene, polyterpene, and norisoprenoid. In another embodiment, the terpene comprises one or more of di-terpenes, tri-terpenes, myrcene, β-caryophyllene, limonene, pinene, and linalool. The first phase comprises fatty acids or fatty acid esters.

In another embodiment, the first phase comprises one or more of mineral oil, vegetable oil, refined kerosene, diesel oil, paraffin oil, or other water-immiscible liquids well known in the art. In one embodiment, the first phase comprises an organic solvent selected from the group consisting of acetic acid, acetone, acetonitrile, 1,2-butanediol, 1,3-butanediol, 1,4-butanediol, 2-butoxyethanol, butyric acid, diethanolamine, diethylenetriamine, dimethylformamide, dimethoxyethane, dimethyl sulfoxide, 1,4-dioxane, ethanol, ethylamine, ethylene glycol, formic acid, furfuryl alcohol, glycerol, methanol, methyl diethanolamine, methyl isocyanide, 1-propanol, 1,3-propanediol, 1,5-pentanediol, propanol, propanoic acid, propylene glycol, pyridine, tetrahydrofuran, and triethylene glycol.

A co-solvent may be present in the first phase that comprises an organic solvent. The amount of co-solvent in the first phase depends on the composition, the concentrations, pH, temperature, or other conditions. In one embodiment, the amount of organic co-solvent within the first phase is less than 5%, in the range between about 5% and about 49%, between about 10% and about 49%, between about 20% and about 49%, between about 30% and about 49%, between about 40% and about 49%, or between about 45% and about 49%. In one embodiment, the amount of organic co-solvent is between about 30% and about 49%. In another embodiment, the amount of organic co-solvent is between about 45% and about 49%. In another embodiment, the amount of organic co-solvent is at least about 50%. In some embodiments, the amount of organic co-solvent is at least about 25%.

In a preferred embodiment, the organic solvent comprising the first phase is soybean oil. In some embodiments, the amount of soybean oil is greater than 50%, in the range between about 50% and about 90%, between about 50% and about 80%, between about 50% and about 79%, between about 50% and about 70%, between about 50% and about 60%, or between about 50% and about 55% of the organic solvent. In another embodiment, the amount of soybean oil is between about 50% and about 60%. In some embodiments, the amount of soybean oil is about 53%.

In another embodiment, the organic solvent comprising the first phase is terpene. In some embodiments, the amount of terpene is greater than 50%, in the range between about 50% and about 90%, between about 50% and about 80%, between about 50% and about 79%, between about 50% and about 70%, between about 50% and about 60%, or between about 51% and about 55% of the organic solvent.

In one embodiment, the second phase comprises one or more polar co-solvents that are miscible in water. In one embodiment, the water miscible co-solvent comprises one or more of dimethyl sulfoxide (DMSO), dimethylacetamide (DMA), dimethylformamide (DMF), isopropyl alcohol, cyclodextrin, peroxide scavenger, and methanol (MeOH), and the combination thereof. In some embodiments, the amount of the water miscible co-solvent in the second phase is less than 0.1%, between about 0.1% and less than 50% (w/v), about 1% and about 50%, about 5% and about 40%, or about 5% and about 30%, or about 5% and about 20%, about 10% and about 15% of the aqueous solution.

In some embodiments, the second phase comprises DMSO in an amount less than 0.1%, between about 0.1% and about 50% (w/v), about 1% and about 50%, about 5% and about 40%, or about 5% and about 30%, or about 5% and about 20%, or about 10% and about 15% of the aqueous solution. In one embodiment, the amount of DMSO in the second phase is above 0.1%, 1%, 10%, 20%, 30%, 40%, or less than 50%. In another embodiment, the second phase comprises DMSO in an amount between 1% and 20% of the aqueous solution. In one embodiment, the amount of DMSO is between about 10% and about 20%. In another embodiment, the amount of DMSO is about 20%.

In one embodiment, the second phase comprises MeOH in an amount less than 0.1%, between about 0.1% and about 50% (w/v), about 1% and about 50%, about 5% and about 40%, or about 5% and about 30%, or about 5% and about 20%, or about 10% and about 15% of the aqueous solution. In one embodiment, the amount of MeOH in the second phase is above 0.1%, 1%, 10%, 20%, 30%, 40%, or 49%. In another embodiment, the second phase comprises MeOH in an amount between about 1% and about 20% of the aqueous solution. In a different embodiment, the amount of MeOH is between about 10% and about 20%. In a different embodiment, the amount of MeOH is between about 1% and about 6%.

In one embodiment, the second phase comprises dimethylacetamide (DMA) in an amount less than 0.1%, between about 0.1% and about 50% (w/v), about 1% and about 50%, about 5% and about 40%, or about 5% and about 30%, or about 5% and about 20%, or about 10% and about 15% of the aqueous solvent. In one embodiment, the amount of DMA is about 0.1%, 1%, 10%, 20%, 30%, 40%, 49%. In another embodiment, the second phase comprises DMA in an amount between about 1% and about 20% of the aqueous solvent. In a different embodiment, the amount of DMA is between about 10% and about 20%. In a different embodiment, the amount of DMA is between about 1% and about 6%.

In one embodiment, the biphasic system of this invention comprises a peroxide scavenger that comprises one or more of catalase, glutathione peroxidases (GPx), thioredoxin-assisted peroxidases (Prx), sodium pyruvate, and N',N'-dimethylthiourea (DMTU). In one embodiment, the peroxide scavenger is catalase. In one embodiment, the amount of the peroxide scavenger in the aqueous solution is between about 0.001% and about 0.1%, about 0.005% and about 0.05%, or about 0.01% and about 0.03% (w/v). In one embodiment, the amount of peroxide scavenger is about 0.01%. In another embodiment, the amount of catalase in the aqueous solvent is between about 0.001% and about 0.1%, about 0.005% and about 0.05%, or about 0.01% and about 0.03% (w/v). In another embodiment, the amount of catalase is about 0.01% of the aqueous solution.

As noted above, the disclosure provides that the pH value and the ratio of organic solvent to the aqueous solution in the composition can unexpectedly affect the cannabinoid synthesis and the ratio of cannabinoid products produced. In one embodiment, the pH value of the aqueous solution in the composition ranges from about 3.5 to about 10.0, from about 3.5 to about 9, from about 4 to about 8, or from about 5.5 to about 7.5. In one embodiment, the pH value ranges from about 4.5 to about 7.5. Alternatively, the pH value ranges from about 5.5 to about 7.5. In some embodiments, the pH value ranges from about 5.0 to about 6.5. In one embodiment, the pH value is about 7.5. In another embodiment, the pH value is about 5.5. In yet another embodiment, the pH value is about 4.5.

In some embodiments, the second phase comprises DMSO in a range between about 1% and 30%, about 2% and about 20%, or 5% and about 10% of the aqueous solution, wherein the pH value of the aqueous solution is between about 3 and about 9, about 4 and about 8, or about 5.5 and about 7.5. In some embodiments, phase 2 comprises DMSO in a range between about 5% and about 10% of the aqueous solution, wherein the pH value of the aqueous solution is between about 5.5 and about 7.5. In one embodiment, the second phase comprises DMSO in an amount of about 5%, wherein the pH value of the aqueous solution is about 5.5. In another embodiment, the second phase comprises DMSO in an amount of about 10%, wherein the pH value of the aqueous solution is about 7.5.

In one embodiment, the volumetric ratio of the organic solvent to the aqueous solution is from about 1:9 to about 9:1; from about 1:8 to about 8:1; from about 1:7 to about 7:1; from about 1:6 to about 6:1; from about 1:5 to about 5:1; from about 1:4 to about 4:1; from about 1:3 to about 3:1; or from about 1:2 to about 2:1. In another embodiment, the volume ratio is from about 1:2 to about 2:1.

In some embodiments, the composition further comprises a cannabinoid synthase which comprises one or more of CBDA synthase, THCA synthase, or/and CBCA synthase. In one embodiment, the composition comprises CBDA synthase or THCA synthase. The cannabinoid synthase can be in its crude form or its purified form. In one embodiment, the cannabinoid synthase is lyophilized to a powder which is directly added to the second phase or alternatively, the lyophilized powder is dissolved in a specific volume of a buffer and this solution is added to the second phase of the bi-phasic system.

In one embodiment, the concentration of the synthase in the aqueous solution is at least 0.1 mg/mL, 0.5 mg/mL, 1 mg/mL, 2 mg/mL, 5 mg/mL, 10 mg/mL, 32 mg/mL, 50 mg/mL, or 100 mg/mL. In another embodiment, the concentration of the synthase in the aqueous solution is at least 5 mg/mL. In another embodiment, the concentration of the synthase in the aqueous solution is at least 32 mg/mL. For some embodiments, the cannabinoid synthase is purified and the concentration of the purified synthase in the aqueous solution is at least 50 µg/mL. In some embodiments, the concentration of the purified synthase in the aqueous solution is at least 200 µg/mL.

In some embodiments, the concentration of cannabinoid precursor in the organic solvent is at least about 0.1 mg/mL, 1 mg/mL, 10 mg/mL, 20 mg/ml, 25 mg/ml, 30 mg/ml, 35 mg/ml, about 50 mg/mL, about 100 mg/mL, about 150 mg/mL, about 200 mg/mL, about 250 mg/mL, or about 300 mg/mL. In one aspect of this invention, the concentration of cannabinoid precursor in the organic solvent is between about 0.1 mg/mL and about 250 mg/mL, about 1 mg/mL and 200 mg/mL, about 20 mg/mL and about 150 mg/mL, or about 50 mg/mL and about 100 mg/mL. In one embodiment, the cannabinoid precursor is one or more of CBGA, CBGVA, or their derivative or analog.

Apparatus and System

This disclosure also provides an apparatus or a system for producing one or more cannabinoids, cannabinoid prodrugs, or cannabinoid analogs. The apparatus may comprise a fermentor 10, a bioreactor 30, and a control mechanism 40. FIG. 1A depicts an apparatus 100 configured to produce at least one cannabinoid, cannabinoid prodrug and/or at least one cannabinoid analog according to an embodiment. As shown in FIG. 1A, the apparatus 100 includes a fermentor 10, a bioreactor 30, and a control mechanism (controller) 40. The fermentor 10 holds cell culture medium 12 and a plurality of cells 14. The cells 14 are configured to produce one or more cannabinoid acid synthases. The cells may be genetically engineered according to the invention to secrete the cannabinoid acid synthase into the medium. Optionally, the majority of the cannabinoid acid synthase remains intracellular, is secreted into the medium, or is found both inside and outside the cells. The cells 14 grown in the fermentor 10 for the manufacture of a cannabinoid acid synthase can be prokaryotes such as *Escherichia coli, Bacillus, Pseudomonas* or any number of gram positive or gram negative bacteria. Alternatively, the cells 14 grown in the fermentor 10 can be eukaryotic cells such as yeast (e.g., *Pichia, Saccharomyces, Yarrowia*), algae, insect, or plant cells. In one embodiment, the prokaryotic or eukaryotic cells are genetically modified to include a nucleic acid construct comprising one or more genes that encode a cannabinoid acid synthase protein. In one embodiment, the cannabinoid synthase comprises CBDA synthase or THCA synthase.

In certain embodiments, the nucleic acid sequence that encodes a cannabinoid acid synthase protein is modified to include a secretion signal operably linked to the 5' region of the cannabinoid synthase gene. In another embodiment, cannabinoid acid synthase proteins include a 6-residue histidine tag at their 3' end to facilitate enzyme purification. The addition of a secretion sequence permits secretion of the cannabinoid acid synthase protein into the medium 12 used for prokaryotic or eukaryotic cell growth. Following production of one or more cannabinoid acid synthases in the fermentor 10, the supernatant is collected and dried to produce a technical grade enzyme. Drying can be done by any method known in the art such as lyophilization, freeze drying, or the like. Alternatively, the enzyme is purified using a method well known in the art, such as nickel column chromatography, and then introduced into the aqueous second phase.

The bioreactor 30 is designed to permit mixing of the first phase and second phase after introduction of substrate into the first phase and cannabinoid synthase enzyme into the second phase. The first phase comprises a cannabinoid precursor. In some embodiments, the cannabinoid precursor is the compound of Formula II:

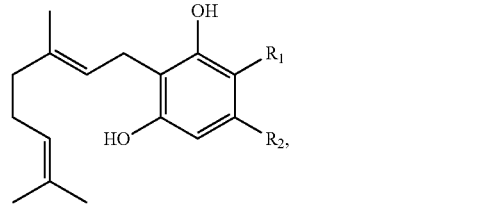

Formula II wherein $R_1$ is H or —COOH and $R_2$ is a linear or branched $CH_3$, $C_2H_5$, $C_3H_7$, $C_4H_9$, $C_5H_{10}$, $C_6H_{13}$, $C_7H_{15}$ or $C_8H_{17}$ group, wherein the cannabinoid precursor is configured to interact with the cannabinoid synthase to form the cannabinoids or its analog. In one embodiment, the cannabinoid precursor is cannabigerolic acid (CBGA), cannabigerovarinic acid (CBGVA), or their derivative or analog. In another embodiment, the first phase of the bioreactor is agitated to form micro-droplets within the second phase, wherein at least one micro-droplet comprises the cannabinoid precursor.

Mixing of the first and second phases is accomplished in any way known in the art such as shaking, spinning, sparging with a gas such as oxygen, or stirring with an impeller. In one embodiment, the first phase comprises an organic solvent and the second phase comprises an aqueous solvent. In another embodiment, the first phase is substantially water-immiscible or water-immiscible. In one embodiment, the substantially water immiscible or water immiscible solvent comprises one or more of olive oil, sesame oil, castor oil, cotton-seed oil, soybean oil, butane, pentane, heptane, octane, isooctane, nonane, decane, and terpene. In another embodiment, the terpene comprises one or more of hemiterpene, monoterpene, sesquiterpene, diterpene, sesterterpene, triterpene, sesquarterpene, tetraterpene, polyterpene, and norisoprenoid. In another embodiment, the terpene comprises one or more of diterpene, tri-terpene, myrcene, β-caryophyllene, limonene (or dipentene), pinene, and linalool. In one embodiment, the organic solvent comprises soybean oil. In another embodiment, the aqueous solvent further comprises one or more of dimethyl sulfoxide (DMSO), dimethylformamide (DMF), dimethylacetamide (DMA), isopropyl alcohol, cyclodextrin, peroxide scavenger, and methanol (MeOH), wherein the amount of the aqueous solvent is between about 0.001% and about 50% (w/v), about 1% and about 40%, about 1% and about 30%, or about 1% and about 20% of the second phase. In another embodiment, the aqueous solvent comprises DMSO in an amount between about 0.1% and about 50% of the aqueous solution. In another embodiment, the aqueous solvent comprises MeOH in an amount between about 1% and about 20% of the aqueous solution. In another embodiment, the peroxide scavenger is one or more of catalase, glutathione peroxidases (GPx), thioredoxin-assisted peroxidases (Prx), Sodium pyruvate, and N,N'-dimethylthiourea (DMTU). In another embodiment, the aqueous solvent comprises the peroxide scavenger in an amount between about 0.001% and about 0.1%, about 0.005% and about 0.05%, or about 0.01% and about 0.03% of the aqueous solution. In another embodiment, the aqueous solvent comprises catalase in an amount between about 0.001% and about 0.1%, about 0.005% and about 0.05%, or about 0.01% and about 0.03% of the aqueous solution. In one embodiment, the pH value of the aqueous solvent ranges from about 3.5 to about 9.0.

In another embodiment, the aqueous co-solvent comprises DMSO in a range between about 5% and about 10% of the aqueous solution, wherein the pH value of the aqueous solution is between about 5.5 and about 7.5. In one embodiment, the volume ratio of the first phase to the second phase is from about 1:9 to about 9:1.

The bioreactor 30 can be a column bioreactor having a solid support that is impregnated with divalent metal ions or a support whose surface is functionalized with divalent metal ions. Typically, sepharose, agarose, or other biopolymers are used as supports for binding divalent metal ions such as nickel, cobalt, magnesium, and manganese. Such supports have a strong affinity for the histidine tag that is present on the expressed cannabinoid synthase and can be used to sequester the synthase and separate it from other non-essential proteins and debris that may interfere or impede cannabinoid synthesis.

The bioreactor 30 used for synthesizing cannabinoids is configured for batch and continuous synthetic processes to permit commercial production of pharmaceutically useful cannabinoids. In one embodiment, the bioreactor 30 is configured for batch synthesis in which the composition of the medium, concentration of the enzyme and substrate are fixed at the beginning of the process and not allowed to change during catalysis. Synthesis is terminated when the concentration of the desired product in the medium of the bioreactor 30 reaches a predetermined value or the concentration of substrate falls below a predetermined level, such as to a level where there is no detectable catalytic conversion of substrate to product. In one embodiment, therefore, the His-tagged cannabinoid synthase is sequestered onto a nickel containing resin support within the bioreactor column prior to the introduction of a known amount of substrate or cannabinoid precursor, for example, CBGA, CBGVA, or a Formulae II compound into the bioreactor (30). In an alternate embodiment, the cannabinoid precursor is present within the bioreactor having a nickel resin support prior to the introduction of the medium containing a cannabinoid synthase into the bioreactor (30). In either case, a known amount of the enzyme is contacted with a known amount of a cannabinoid precursor to synthesize a cannabinoid or a cannabinoid analog as product.

In one embodiment, the cannabinoid acid synthase is introduced into the second phase within the bioreactor 30 prior to the introduction of a known amount of substrate of Formula I. The first phase containing the substrate of Formula I is then introduced into the bioreactor.

The system, in some embodiments, further includes a filter situated between the fermentor 10 and the bioreactor 30. The filter may filter the supernatant to at least partially separate the cells from the medium containing the expressed enzyme. Typically, the filter separates at least 80% of the total cells from the medium. For certain embodiments, the filter separates at least 85%, at least 90%, at least 91%, at least 92%, at least 93%, at least 94%, at least 95%, at least 96%, at least 97%, at least 98%, at least 99%, or 100% of the total cells from the medium (4) prior to the introduction of this medium containing the synthase into the bioreactor. Following filtration, the cells are transported back to the fermentor, collected for lysate outside the fermentor, or added to the bioreactor. In some embodiments, the filter is a filtration and purification system that includes multiple filters and reservoirs to purify the cannabinoid synthase.

The progress of the reaction within the bioreactor 30 can be monitored periodically or continuously. For instance, an optical monitoring system 50 may be utilized to detect the concentration of product in the medium within the bioreactor as a function of time. Alternatively, the decrease in the concentration of substrate can be monitored to signal termination of synthesis. The cannabinoid product thus produced can be readily recovered from the first phase in which the product accumulates. The cannabinoid or cannabinoids in the first phase are readily purified by solvent extraction or chromatographic purification methods. The monitoring system 50 may be part of or may interact with a control mechanism 40 (a controller) described herein.

An alternative to the batch process mode is the continuous process mode in which a defined amount of substrate and medium are continuously added to the bioreactor (30) while an equal amount of medium containing the cannabinoid product is simultaneously removed from the bioreactor 30 to maintain a constant rate for formation of product. Medium can enter the bioreactor through an inlet and exit the bioreactor through outlet. Methods of modulating the concentration of substrate, enzyme and other factors implicated to maximize the rate of product formation are known in the art.

An alternative to the batch process mode is another mode in which the first phase containing one or more cannabinoid products is removed though 34 or 35 and the cannabinoid products purified. The first phase containing an amount of the substrate (or cannabinoid precursor) of Formula I is then introduced into the bioreactor through 34 or 35. The progress of the reaction is monitored to determine when a sufficient amount of substrate has been converted to product. The removal and replenishment of the first phase with a predetermined amount of substrate of Formula I can be repeated so long as the cannabinoid synthase in the second phase remains active.

The conditions of the bioreactor can be controlled using a control mechanism 40. The control mechanism 40 may be coupled to the bioreactor 30 or, alternatively, may interact with the bioreactor 30 wirelessly or remotely. The control mechanism 40 may also be used to control the conditions of the fermentor 10, such as the oxygen level, agitation, pH, pressure, solvent, flow rate, and feed rate. The control mechanism 40 may also control the flow of materials (e.g., by controlling at least one pump) into and out of the fermentor 10 and bioreactor 30. In some embodiments, the control mechanism 40 is configured to control the conditions of at least one of the fermentor 10 and the bioreactor 30 based on information obtained from the optical monitoring system 50.

Figure 1B:
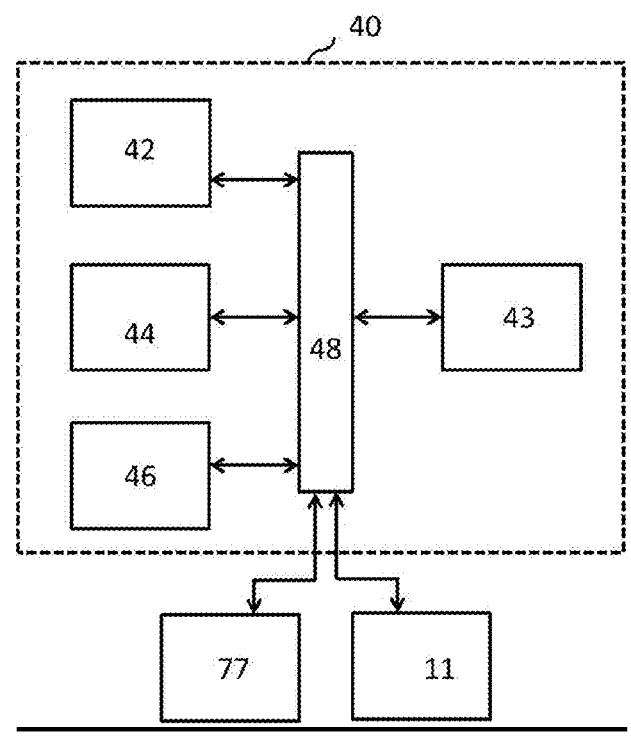

The control mechanism 40 of FIG. 1B may include a processing circuit having a processor and memory device. The processor can be implemented as a general purpose processor, an application specific integrated circuit (ASIC), one or more field programmable gate arrays (FPGAs), a group of processing components, or other suitable electronic processing components. The memory device (e.g., memory, memory unit, storage device, etc.) is one or more devices (e.g., RAM, ROM, Flash memory, hard disk storage, etc.) for storing data and/or computer code for completing or facilitating the various processes and functions described in the present disclosure, such as controlling the pH, temperature, and pressure of the bioreactor 30, or altering the flow rate of medium into or out of the bioreactor (30). The processor and memory are configured to complete or facilitate the various processes and functions described in the present application, such as controlling the pH, temperature, and pressure of the bioreactor 30, or altering the flow rate of solvents, cells and the like into or out of the bioreactor 30. In some embodiments, for facilitating the control of pH, temperature, pressure and flow rate, the control mechanism 40 may be configured to communicate with at least one sensor in a sensor suite 60. The sensor suite 60 may include a pH sensor 62, a temperature sensor 63, and a pressure sensor 64. The control mechanism 40 may include a proportional-integral-derivative (PID) controller for feedback-based control. The control mechanism 40 may be further configured to regulate the flow rate of materials into and out of the fermentor 10 and the bioreactor 30 via pulse width modulation (PWM) techniques. The bioreactor is able to produce one or more cannabinoids (e.g., a first cannabinoid and a second cannabinoid) or their analogs. Thus, the condition of the bioreactor is configured to cause a shift from: 1) formation of the first cannabinoid in greater quantities relative to the second cannabinoid to 2) formation of the second cannabinoid in greater quantities relative to the first cannabinoid. In one embodiment, the cannabinoid so produced from the system comprises (a) tetrahydrocannabivarinic acid (THCVA) and cannabichrome varinic acid (CBCVA), (b) cannabidivarinic acid (CBDVA) and CBCVA, (c) tetrahydrocannabinolic acid (THCA) and cannabichromenic acid (CBCA), and/or (d) cannabidiolic acid (CBDA) and CBCA.

The control mechanism 40 includes a processor 43 coupled to a communication mechanism 48. The control mechanism 40 further includes a main memory 42, such as a random access memory (RAM) or other dynamic storage device, coupled to the bus 48 for storing information, and configured to store instructions to be executed by the processor 43. The main memory 42 is further configured to store temporary variables and intermediate information during execution of instructions by the processor 43. The control mechanism 40 may additionally include a read only memory (ROM) 44 or other static storage device connected to the bus 48 for storing information and instructions. Additionally, a storage device 46, such as a solid state device, magnetic disk or optical disk, may be coupled to the bus 48 for persistently storing information and instructions.

The present disclosure contemplates methods, systems and program products on any machine-readable media for accomplishing various operations, such as controlling the conditions of the bioreactor. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM, or other optical disk storage, magnetic disk storage, other magnetic storage devices, solid state storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Furthermore, the control mechanism 40 may be coupled (via the mechanism 48) to a display 77, such as a liquid crystal display, or active matrix display, for displaying information to a user. In some embodiments, an input device 11, such as a keyboard, may also be coupled to the bus 48 for communicating information, and to convey commands to the processor 43. In some embodiments, the input device 11 has a touch screen display.

The construction and arrangement of the system for producing cannabinoids or cannabinoid analogs as shown in the various exemplary embodiments are illustrative only. Although only a few embodiments have been described in detail in this disclosure, many modifications are possible (e.g., variations in sizes, dimensions, structures, shapes and proportions of the various elements, values of parameters, use of materials, colors, orientations, etc.) For example, the position of elements may be reversed or otherwise varied and the nature or number of discrete elements or positions may be altered or varied. Accordingly, all such modifications are intended to be included within the scope of the present disclosure. Furthermore, the order or sequence of any process or method steps may be varied or re-sequenced according to alternative embodiments. Other substitutions, modifications, changes, and omissions may be made in the design, operating conditions, and arrangement of the exemplary embodiments without departing from the scope of the present disclosure.

WORKING EXAMPLES

Example 1 CBGVA Crystallization in Aqueous Buffer

CBGVA was dissolved at 16 g/L in DMSO and added to 20 mM citrate buffer, pH 4.5 to achieve final CBGVA concentrations in buffer of 0.05, 0.1, 0.2, 0.4, and 0.8 g/L and a DMSO concentration of 5% vol/vol. There was no visible precipitation/crystallization in the 0.05 g/L CBGVA vial, but all of the other vials showed progressively more cloudiness (FIG. 3A). In contrast, vials with CBGA in 20 mM citrate buffer (pH 4.5) and 10% DMSO exhibited precipitation/crystallization, even at 0.05 g/L concentration of (FIG. 3B).

These results show that CBGVA is more soluble in aqueous solution than CBGA. Initially, microscopic examination of the solutions showing cloudiness and/or precipitation revealed small spherical structures. However, after 24 hours large crystals had formed in most of the solutions (FIG. 4). Both CBGA and CBGVA are more soluble in polar organic solvents compared to water (data not shown).

Example 2 Biphasic Oil-Aqueous Systems (1:1) Using CBGVA as Substrate and Lyophilized Cannabinoid Synthases (THCA and CBDA Synthases)

Bio-catalysis was performed using a 1:1 biphasic oil:aqueous solvent system. The oil phase comprising soy-bean oil contained 5 g/L CBGVA. The aqueous phase comprising citrate buffer, pH 5.5, and 10% DMSO contained 32 mg/mL THCA synthase or CBDA synthase. The synthase was previously lyophilized for storage. A 1:1 ratio (1.5 mL of each) of the aqueous and oil phases were used for bio-catalysis.

The bi-phasic reaction mixture (3 mL total volume) was placed on a tube rotator and agitated at 40 rpm at room temperature. The conversion of substrate to cannabinoid products was monitored by removing sample aliquots of oil at each time point shown in FIGS. 5A-5B. Prior to sample collection, the vial containing the reaction mixture was removed from the tube rotator and the two phases allowed to separate by placing the vial of the reaction mixture on the bench top for about 30 mins. Once a clear separation was visible, 10 μL of oil was diluted in 190 μL of isopropanol ("IPA"), vortexed, and analyzed by HPLC.

Figure 5A:
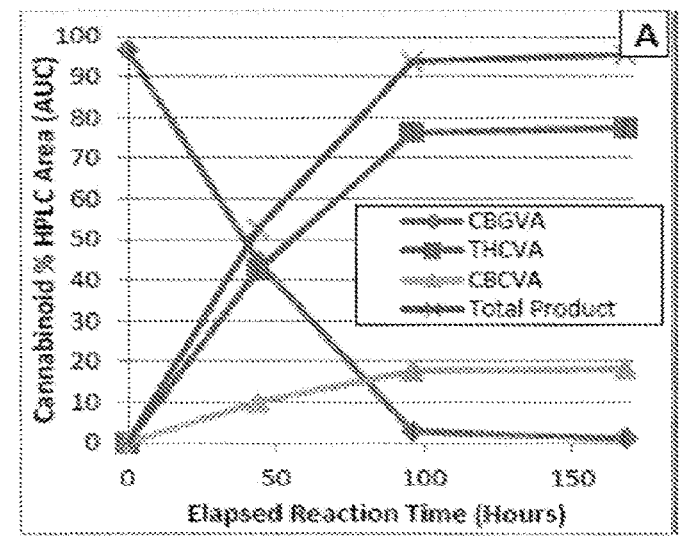
FIGS. 5A-5B shows the results of cannabinoid synthesis in a 1:1 biphasic oil-aqueous reaction with 32 mg/mL lyophilized cannabinoid synthases (THCA synthase for FIG. 5A and CBDA synthase for FIG. 5B). In the biphasic system, the pH of the aqueous phase is 5.5 with 10% DMSO, and the oil phase solution contains 5 g/L CBGVA.
Figure 5B:
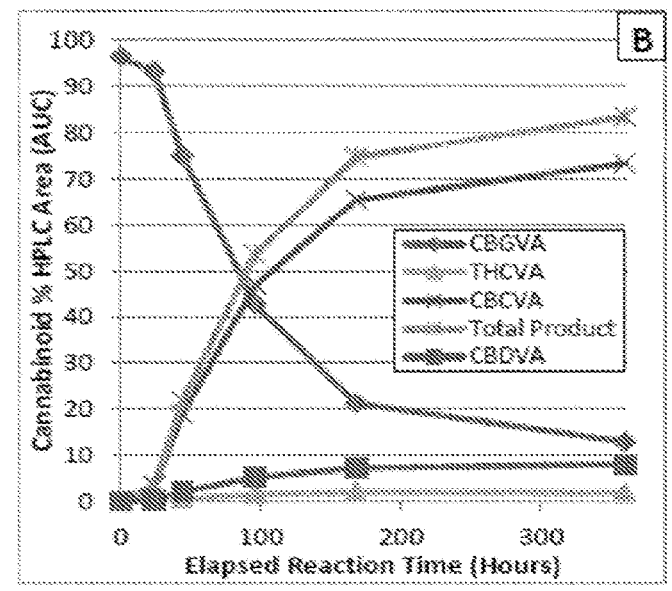

HPLC analysis of the reaction showed that over 90% of the CBGVA substrate had been converted by THCA synthase to THCVA and CBCVA after 96 hours (FIG. 5A). The ratio of THCVA to CBCVA produced using the oil-water (buffer) solvent system was 4.3:1. After 2 weeks, about 83% of the CBGVA had been converted by CBDA synthase to CBDVA and CBCVA, with a CBCVA to CBDVA ratio of 9:1 (minimum amount of THCVA, FIG. 5B). Both enzymes retained catalytic activity and converted substrate to product over an extended period of 300 hours. Cannabinoid synthesis by the CBDA synthase also produced THCVA, which was about 2% of total cannabinoid products (FIG. 5B).

Example 3 Biphasic Oil-Aqueous Systems (1:1) Using CBGVA as Substrate and Purified CBDA Synthase This experiment applied the same reaction conditions as Example 2 except that a purified CBDA synthase was used here (instead of a lyophilized CBDA synthase). Methods to purify CBDA synthase are known in the art. In this experiment, the CBDA synthase was purified using an ion exchange chromatography (Sepharose SP Fast Flow resin (GE healthcare life science)). In this instance, the experiments were intended to test whether the activity of the cannabinoid synthase enzyme and/or cannabinoid product profiles differ significantly when a pure enzyme is used for bio-catalysis.

Figure 6A:
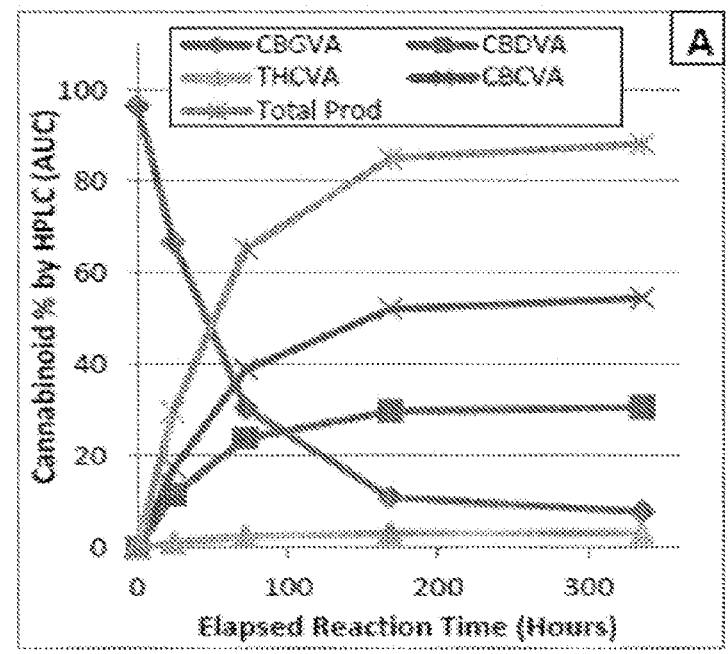
FIGS. 6A-6B depicts the activity of purified CBDA synthase in a 1:1 biphasic oil-aqueous reaction with CBGA as substrate.
Figure 6B:
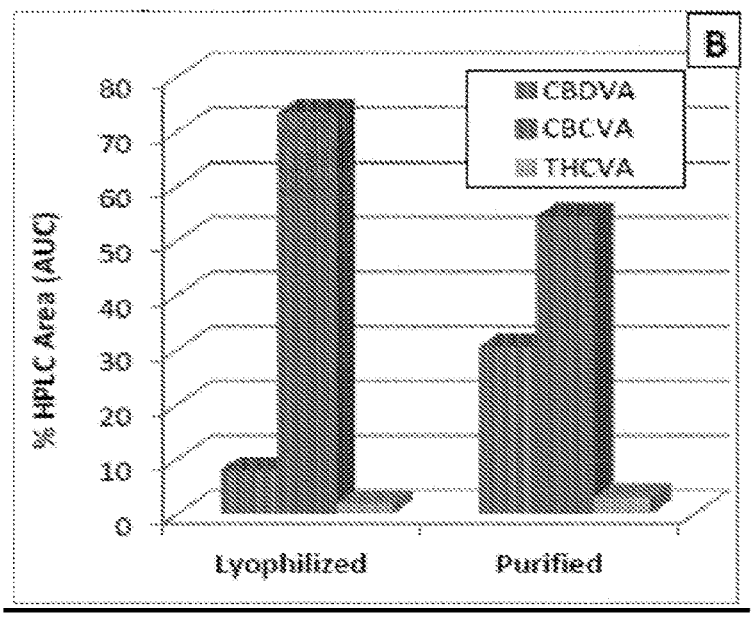

As demonstrated in FIG. 6A, the amount of CBGVA conversion to the cyclized products reached about 88% in a time less than 200 hours. The ratio of CBCVA to CBDVA in this reaction was lower than in the lyophilized enzyme reaction (FIG. 6B). Both lyophilized and purified CBDA synthases favored the production of CBCVA.

Example 4 Effects of pH Values on the Production of Cannabinoids from Biphasic Systems This purpose of this experiment was to evaluate the effect of pH on the ratio of cannabinoid products produced using a biphasic oil-aqueous solvent system. To observe the effect of pH on reaction kinetics, the amount of enzyme used for bio-catalysis was decreased.

Briefly, 10× stock solutions of THCA synthase and CBDA synthase were prepared in a solvent comprising 5% DMSO, 95% deionized water. Enzyme stocks were diluted 1:10 in five separate tubes containing 100 mM sodium citrate buffer at pH values of 4.0, 4.5, 5.0, 5.5, and 6.0 and 5% DMSO. The final enzyme concentration in the aqueous layer comprising 5% DMSO and 95% sodium citrate buffer was about 8.0 mg/mL. 600 μL of soybean oil containing 5 mg/mL CBGVA was overlaid onto 600 μL of aqueous phase containing crude lyophilized THCA synthase at each of the five pH values. Assays were conducted in 2 mL glass HPLC vials and placed on a vertical tube rotator at ambient temperature.

Progress of bio-catalysis at each time point was carried using HPLC, by measuring the amount of each cannabinoid product synthesized as a function of time. Briefly, aliquots of oil from each independent reaction vial were collected after removing the vials from the tube rotator and placing them on a bench top for about 30 minutes so as to allow the two solvents of the bi-phasic system to separate. Once clear separation was visible, 10 μL of oil was pipetted and diluted in 190 μL of IPA, vortexed, and analyzed by HPLC.

Figure 7A:
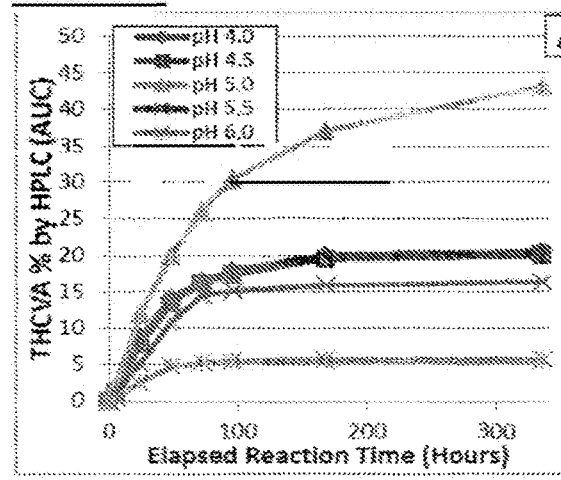
FIGS. 7A-7B and 8A-8B show effects of pH values on production of cannabinoids in 1:1 biphasic soybean oil-aqueous reactions with lyophilized THCA synthase. The aqueous phase contains 32 mg/mL lyophilized THCA synthase.
Figure 7B:
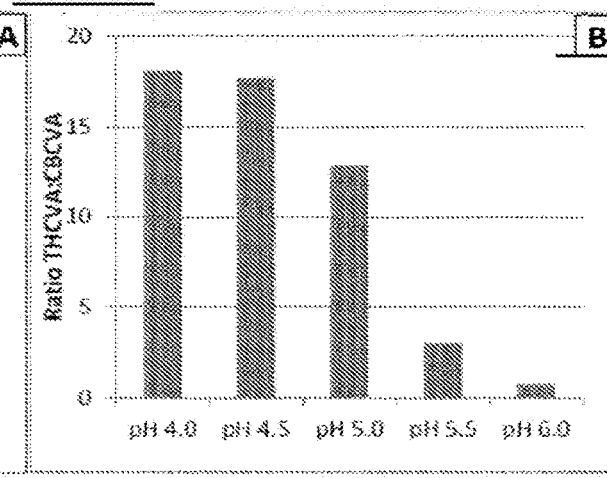
Figure 8A:
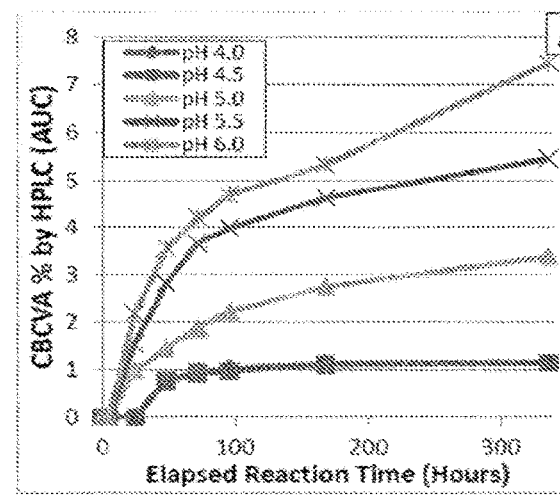
Figure 8B:
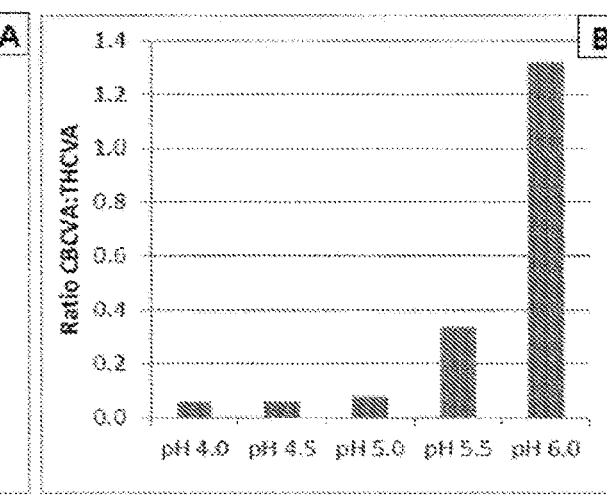
Figure 10A:
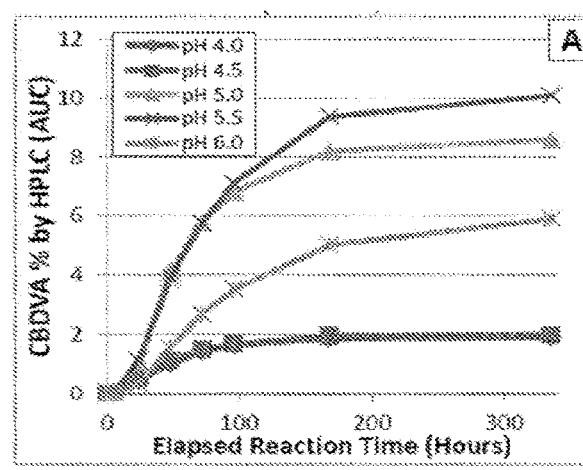
FIGS. 10A-10B and 11A-11B show effects of pH values on production of cannabinoids in 1:1 biphasic soybean oil-aqueous reactions with lyophilized CBDA synthase. The aqueous phase contains 32 mg/mL lyophilized CBDA synthase.
Figure 10B:
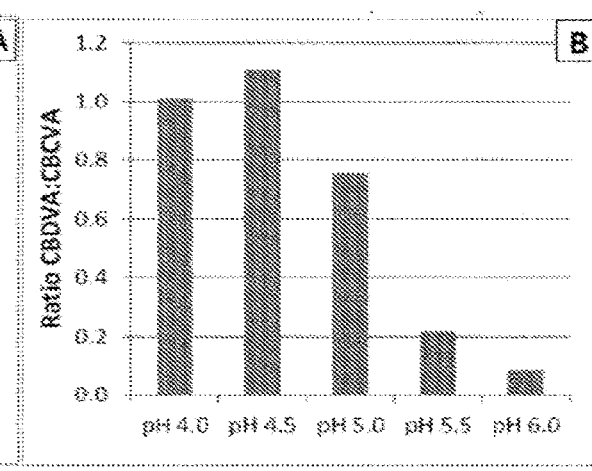
Figure 11A:
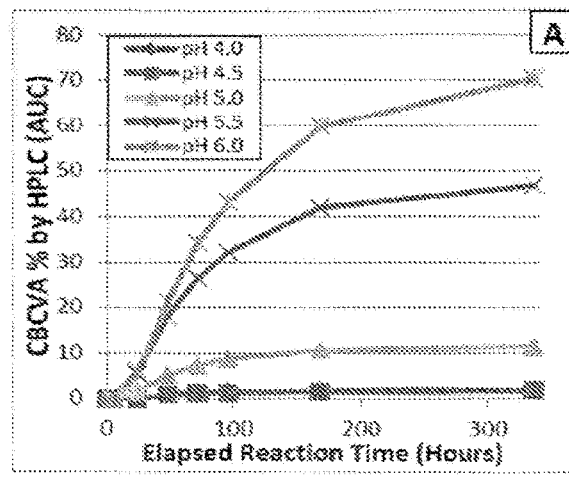
Figure 11B:
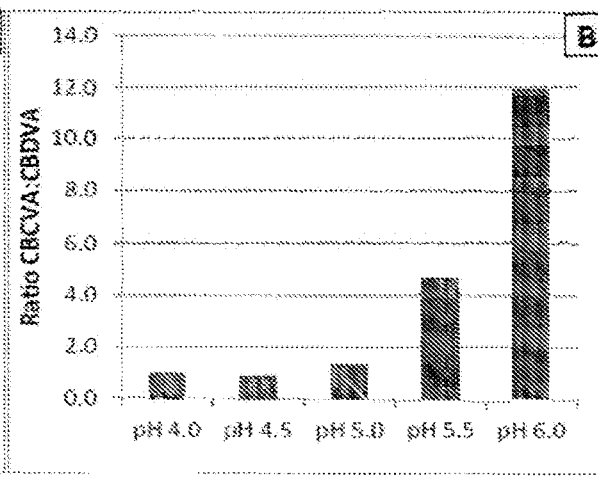

The results show that pH does influence cannabinoid product ratios. Based on the pH values examined, the production of THCVA is highest at pH 5.0 (FIGS. 7A-7B). Increasing the pH shifted the product ratio in favor of CBCVA, with the production of CBCVA being substantially greater at a pH of 6.0 (FIGS. 8A-8B).

pH also influenced cannabinoid product ratios when bio-catalysis is carried out using the enzyme CBDA synthase. The optimal pH for producing CBDVA using bio-catalysis is pH 5.5 (FIGS. 10A-10B). The amount of CBCVA produced fell at pH values below the optimal pH of 6.0 (FIGS. 11A-11B). It was interesting to note that while the largest amount of CBDVA was produced at pH 5.5, the ratio of CBDVA:CBCVA was at its highest at pH 4.5. For CBCVA, the production and the ratio of CBCVA:CBCDA are at their highest at pH 6.0. While greater amounts of CBDVA were synthesized at pH 5.5 (FIGS. 10A-10B), the synthesis of CBCVA was also greater at pH 5.5 than at pH 4.5 (FIGS. 11A-11B). Consequently, in one embodiment, performing bio-catalysis at pH 4.5 using the inventive bi-phasic system may be more suitable, as the purification of CBDVA from CBCVA also produced during bio-catalysis would be less time and cost intensive from a mixture that has a larger amount of CBDVA compared to CBCVA, particularly if the desired cannabinoid product is CBDVA.

The CBGVA substrate used for bio-catalysis can be quantified using a standard curve. To generate a standard curve, 10 mg of CBGVA was dissolved in 10 mL of HPLC grade methanol to a final concentration of 1.0 mg/mL. The stock solution was serially diluted 1:1 using the same lot of HPLC grade methanol, resulting in six vials with CBGVA amounts ranging from 15.625-500 μg/mL.

The CBGVA substrate can be quantified using a standard curve. To generate a standard curve, 10 mg of CBGVA was dissolved in 10 mL of HPLC grade methanol to a final concentration of 1.0 mg/mL. The stock solution was serially diluted 1:1 using the same lot of HPLC grade methanol, resulting in six vials with CBGVA amounts ranging from 15.625-500 μg/mL.

Figure 9:
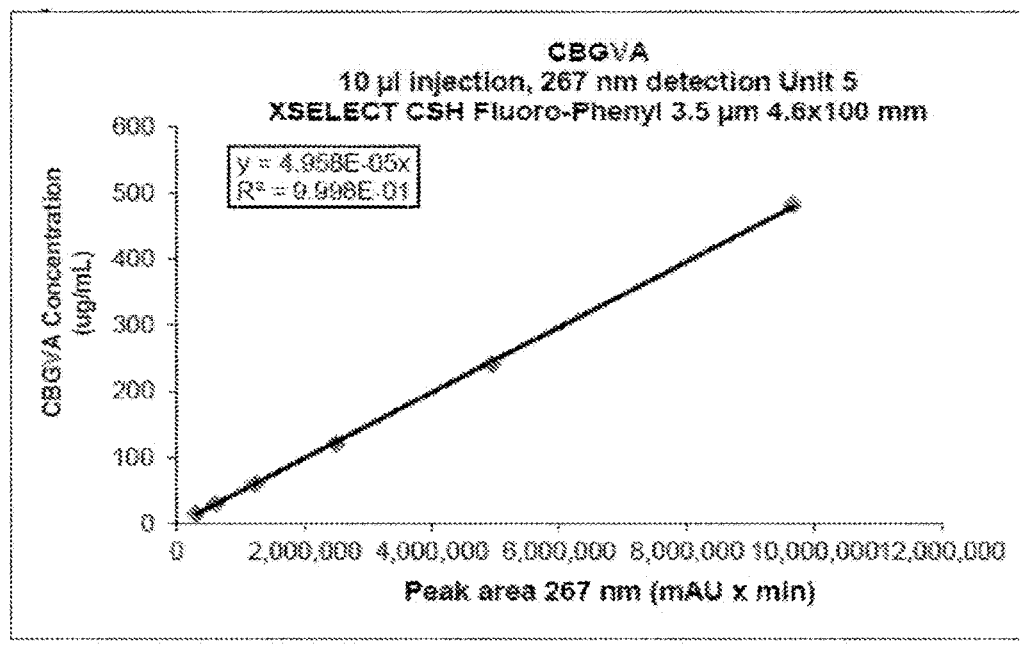
FIG. 9 shows the standard curve for quantifying CBGVA in solution.

After running a methanol blank, all six samples were analyzed by HPLC at 267 nm using an XSELECT CSH Fluoro-Phenyl 3.5 μm 4.6×100 mm column and a 57% acetonitrile+0.1% formic acid isocratic method. Purity of CBGVA lot was determined to be 96.473%. Vial concentrations were adjusted to correct for purity and graphed against the absorbance of the CBGVA peak (FIG. 9). The resulting trendline has the formula y=4.958E-05x with an $R^2$ value of 0.9998 (FIG. 9).

Example 5 Effects of DMSO on CBGVA Cyclization by THCA and CBDA Synthase in a Biphasic Oil-Aqueous System The effect of varying concentrations of DMSO as co-solvent was studied on the product ratio of cannabinoids produced by bio-catalysis using a 1:1 oil-aqueous reaction system. Lyophilized tech-grade THCA synthase or CBDA synthase was dissolved in 100 mM citrate buffer (pH 5.0) containing various concentrations of DMSO (1.25%, 2.5%, 5%, 10%, and 20%). The final enzyme concentration in the aqueous buffer was 8.0 mg/mL. 600 µL of soybean oil containing 5 mg/mL CBGVA was overlaid onto 600 µL of aqueous phase containing either THCA or CBDA synthase at each of the co-solvent concentrations. Assays were conducted in 2 mL glass HPLC vials and placed on a vertical tube rotator at ambient temperature. Reaction progress was monitored by aliquoting a sample of the oil phase from each vial at select time points, after allowing the oil phase to separate from the aqueous phase in each vial. Phase separation is achieved by removing the vials from the tube rotator and allowing each vial to stand on a bench top for ~30 minutes. Once clear separation is visible, 10 µL of oil is diluted in 190 µL of IPA, vortexed, and analyzed by HPLC.

Figure 12A:
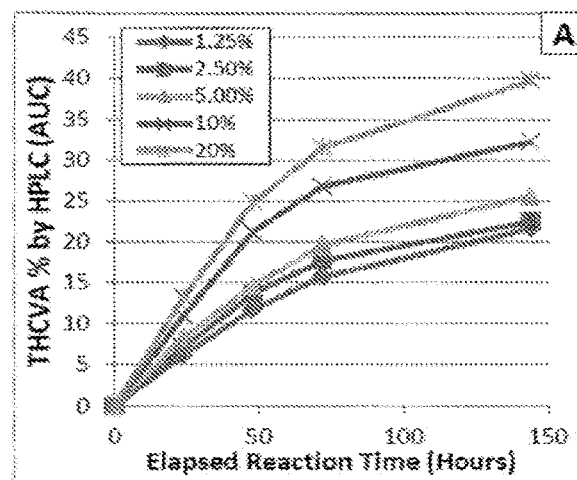
Figure 12B:
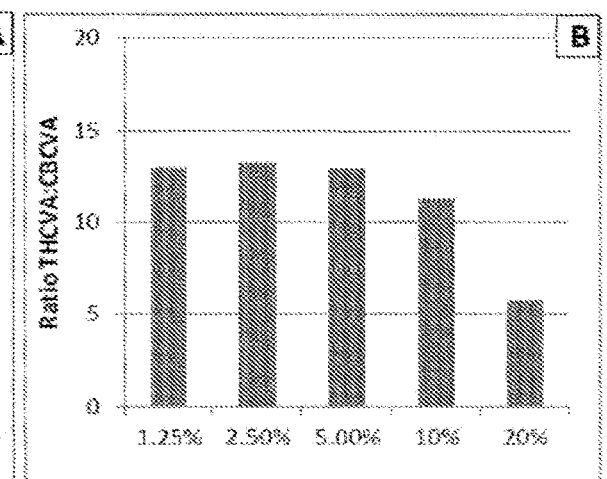

After 144 hours of reaction, the following trends are visible. THCVA production increased as the DMSO concentration increased to 20%, with the 20% DMSO reactions exhibiting 39.7% conversion after 144 hours (FIG. 12A). Also, the ratio of THCVA and CBCVA was its lowest when the DMSO concentration increased to 20% (FIG. 12B).

Figure 13A:
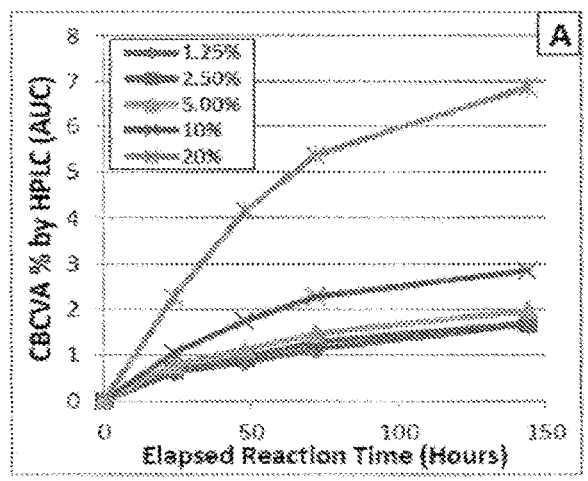
Figure 14A:
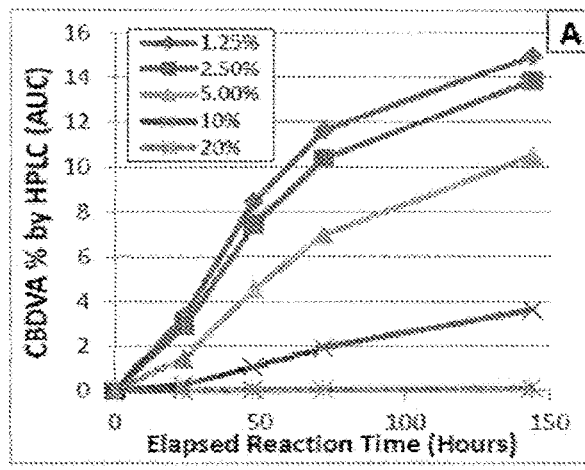
Figure 14B:
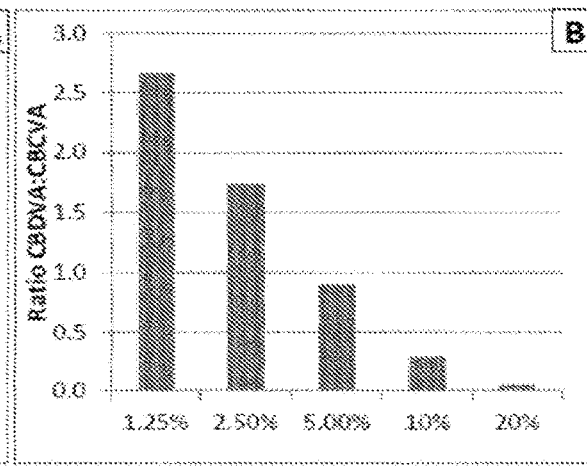

CBCVA production was low (less than 3%) for 1.25%-10% DMSO reactions, with the 20% DMSO reaction showing 6.9% CBCVA (FIG. 13A). The ratio of THCVA and CBCVA was its highest at 20% DMSO. CBDVA production and the ratio of CBDVA to CBCVA were both highest at 1.25% DMSO (FIGS. 14A and 14B).

CBDA synthase is more sensitive to DMSO as a co-solvent than THCA synthase. At 144 hours, CBCVA production was at its highest in 5% and 10% DMSO reactions (FIG. 15A) with total CBCVA production at about 12%, although the ratio of CBCVA to CBDVA was better at 10% DMSO (3.42:1) than at 5% DMSO (1.11:1) (FIG. 15B).

Example 6 Biphasic Oil-Aqueous Systems Using CBGVA as Substrate and THCA Synthase In a biphasic oil-aqueous reaction, the oil phase contained 30 g/L CBGVA. The aqueous phase contained 100 g/L technical grade THCA synthase. The total volume of reaction (including both oil and aqueous phases) was incubated on the tube rotator. At each time point indicated in FIG. 16, the samples of the oil phase were collected by removing the vials from the tube rotator and allowing the oil and aqueous phases to separate. Once a clear separation was visible, the oil aliquot was diluted in IPA, vortexed, and analyzed by HPLC.

The reaction resulted in a rapid and high conversion (above 95%) of CBGVA to the varin series of cannabinoid products (THCVA and CBCVA) within about 45 hours since the reaction started. With its high volumetric efficiency, the biphasic system produced about 24 g/L THCVA and about 5 g/L CBCVA, with a good ratio of THCVA to CBCVA (FIG. 16).

Figure 17:
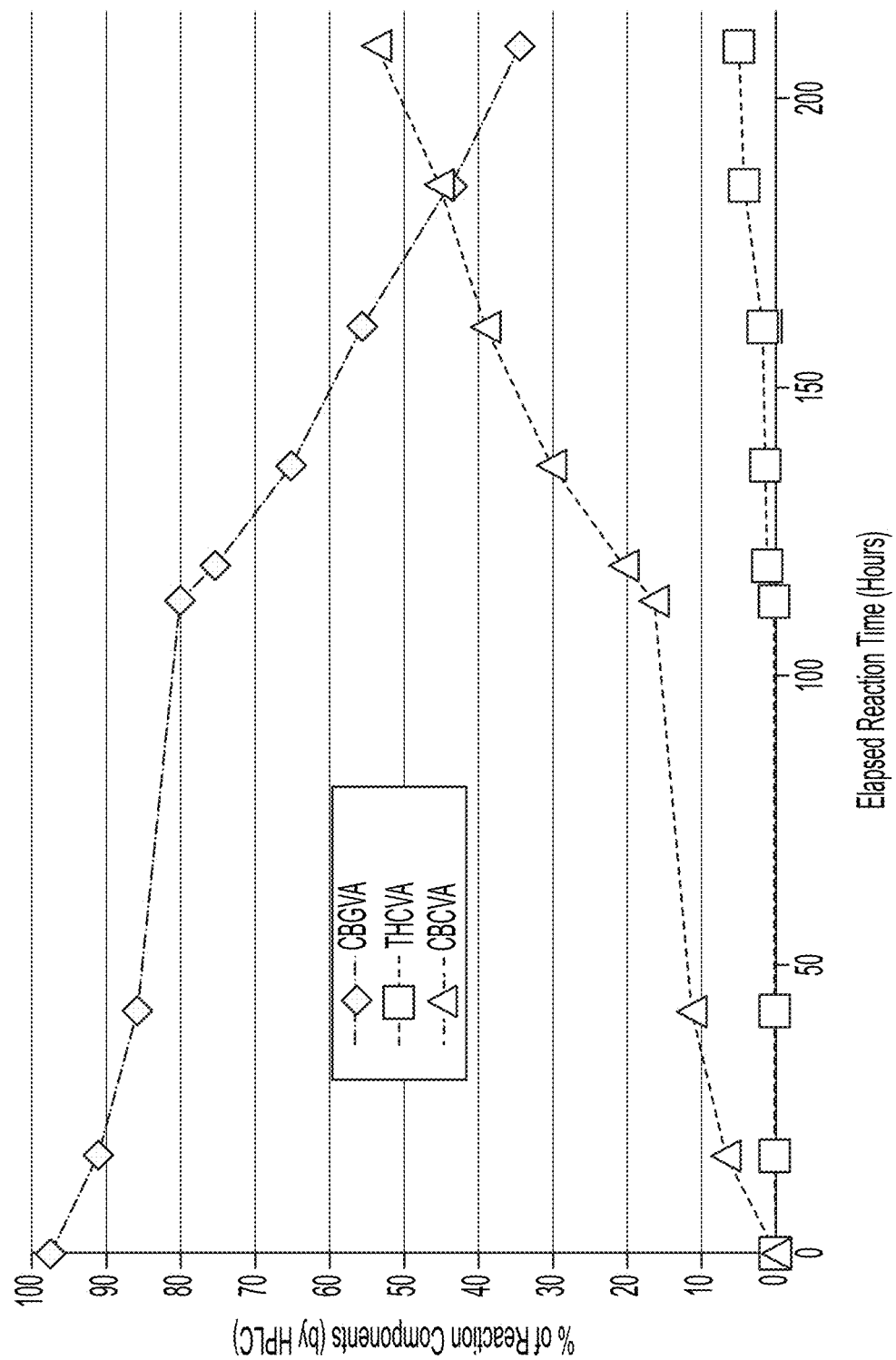

In a separate biphasic oil-aqueous reaction, the oil phase contained about 14.6 g/L CBGVA as substrate and the aqueous phase contained THCA synthase. The pH in the aqueous phase was optimized for CBCVA production. The total reaction mixture (including both oil and aqueous phases) was incubated on the tube rotator. At each time point indicated in FIG. 17, the samples of the oil phase were collected by removing the vials from the tube rotator and allowing them to separate. Once a clear separation was visible, the oil aliquot was diluted in IPA, vortexed, and analyzed by HPLC.

In the reaction, about 70% CBGVA was converted to varin cannabinoid products within about 200 hours. (FIG. 17) The reaction produced 11 g/L CBCVA and 2 g/L THCVA with a good ratio of CBCVA to THCVA (around 10:1).

In a similar and separate reaction, more than 99% of the CBGVA was converted to varin cannabinoids within 22 hours, and the reaction produced more than 14 g/L of THCVA and <0.1 g/L THCVA, with a CBCVA to THCVA ratio of 154:1 (data not shown).

Figure 18:
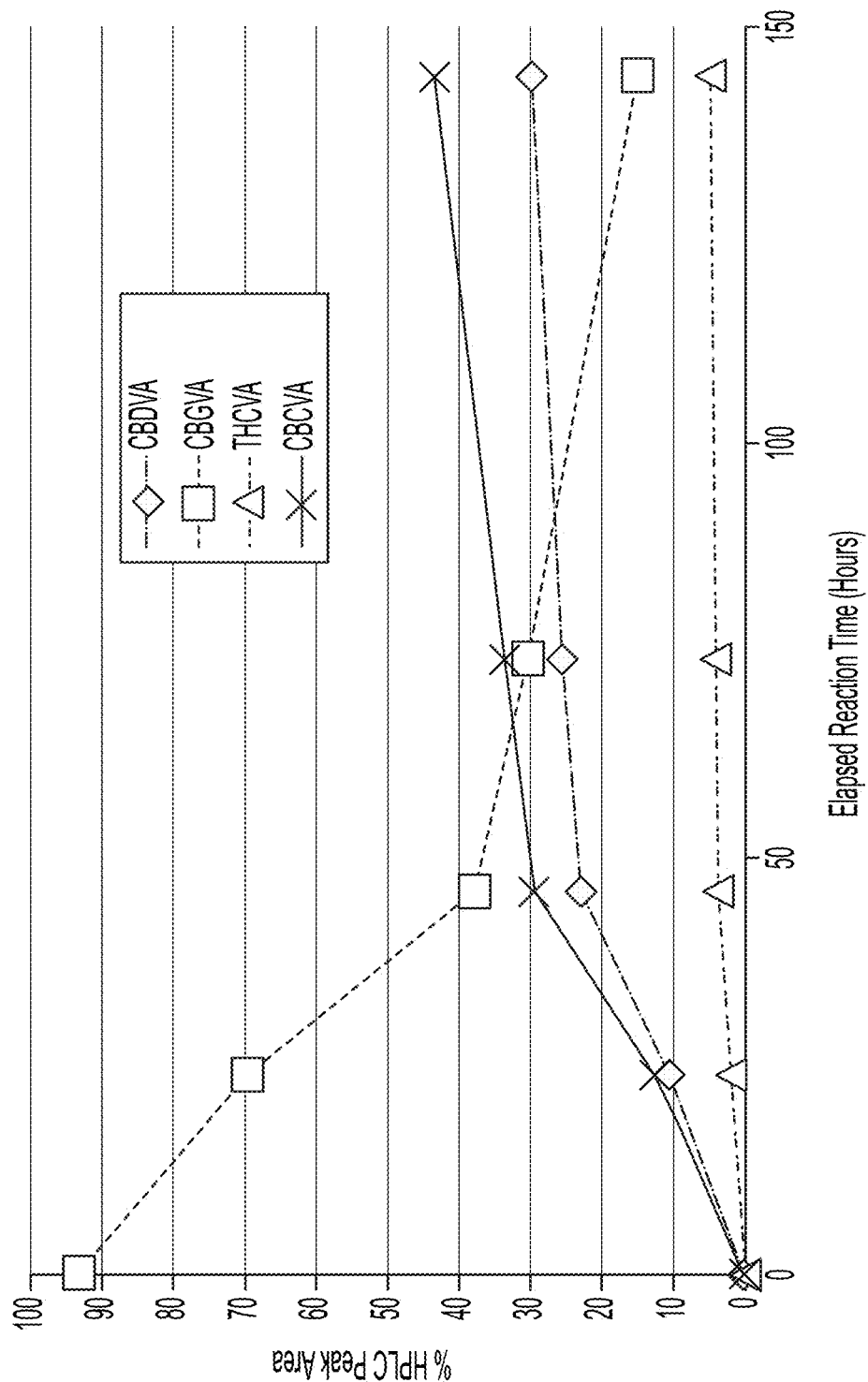
FIG. 18 depicts the activity of CBDA synthase in a biphasic oil-aqueous reaction with CBGVA as substrate.

Example 7 Biphasic Oil-Aqueous Systems Using CBGVA as Substrate and CBDA Synthase In a biphasic oil-aqueous reaction, the oil phase contained about 21 g/L CBGVA and the aqueous phase contained CBDA synthase. The total volume reaction (including both oil and aqueous phases) was incubated on the tube rotator. At each time point indicated in FIG. 18, the samples of the oil phase were collected by removing the vials from the tube rotator and allowing them to separate. Once a clear separation was visible, the oil aliquot was diluted in IPA, vortexed, and analyzed by HPLC.

Figure 19:
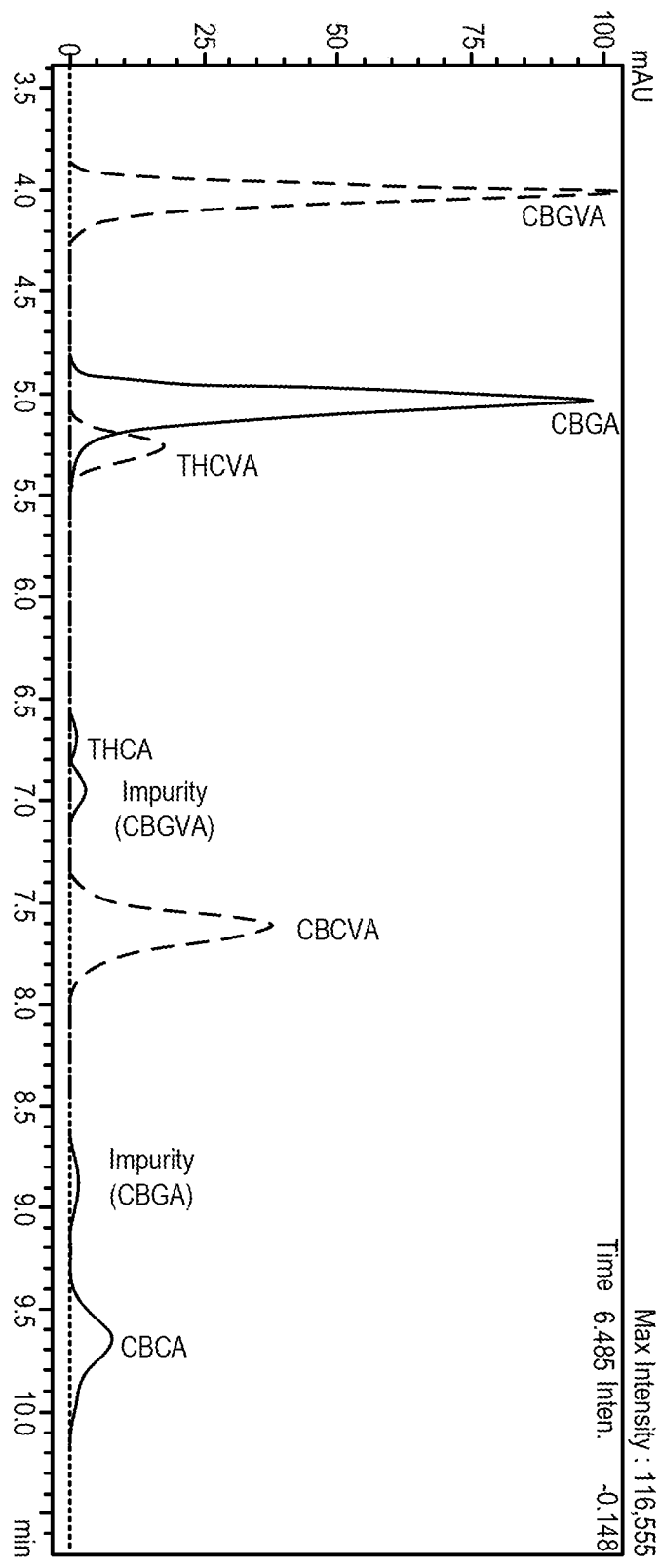
FIG. 19 shows the chromatographic identifications of varin series of compounds by RP-HPLC.

The reaction produced about 10 g/L CBCVA, 7 g/L CBDVA, and about 1 g/L THCVA with a product ratio favoring CBCVA over CBDVA and THCVA. This reaction (FIG. 18) was slightly slower or less efficient than the bio-catalytic reaction optimized for THCVA production (FIG. 16). The varin cannabinoid compounds are well resolved by RP-HPLC as shown in FIG. 19.

Example 8 Biphasic Oil-Aqueous Systems (1:1) Using CBGA as Substrate and Lyophilized Cannabinoid Synthases (THCA and CBDA Synthases)

In a 1:1 biphasic oil-aqueous reaction, the oil phase contains 5 g/L CBGA dissolved in soybean oil. The aqueous phase contains 32 mg/mL THCA synthase or CBDA synthase. Both enzymes were reconstituted using lyophilized enzyme powder and an aqueous buffer. The aqueous phase includes citrate buffer and 10% DMSO at pH value at of 5.5. The aqueous phases were combined with oil phases at 1:1 ratio (1.5 mL of each).

The total reaction mixture (3 L) was placed incubated on the tube rotator and spun at 40 rpm at room temperature. At each time point indicated in FIGS. 20A-20B, the samples of the oil phase were collected by removing the vials from the tube rotator and allowing them to separate for about 30 mins. Once a clear separation was visible, 10 µL of oil was diluted in 190 µL of IPA, vortexed, and analyzed by HPLC.

Figure 20A:
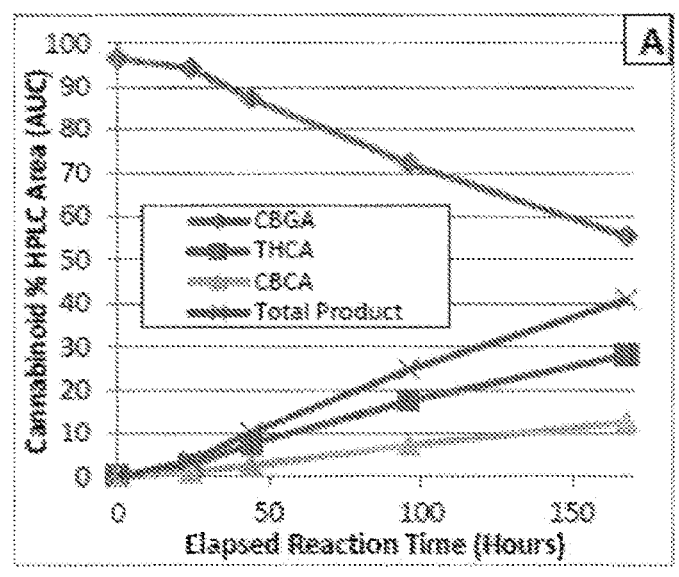
FIGS. 20A-20B show the results of cannabinoid synthesis in a 1:1 biphasic oil-aqueous reaction with 32 mg/mL lyophilized cannabinoid synthases (THCA synthase for FIG. 20A and CBDA synthase for FIG. 20B). In the biphasic system, the aqueous phase solution was at pH 5.5 with 10% DMSO, and the oil phase solution contains 5 g/L CBGA in oil phase.
Figure 20B:
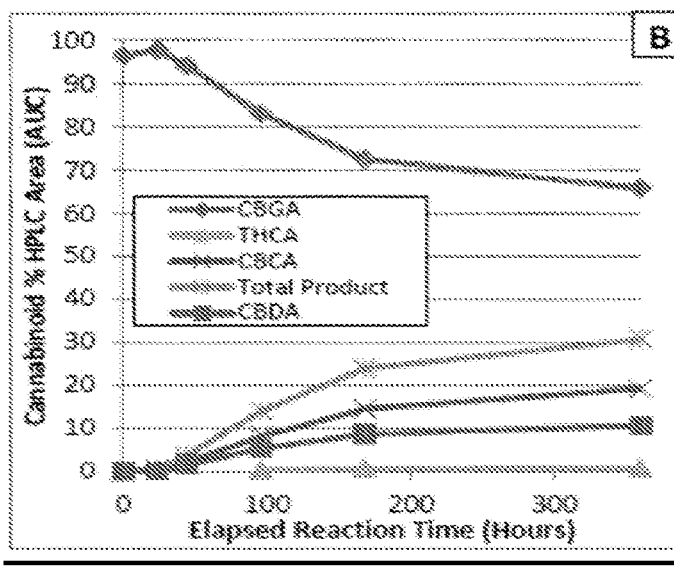

After the same 96 hour period, about 25% of the CBGA was converted by THCA synthase to THCA and CBCA (FIG. 20A), and about 19% of the CBGA had been converted by CBDA synthase to CBDA and CBCA products (minimum amount of THCA, FIG. 20B). Both reactions were permitted to progress and after 168 hours, the conversion of CBGA to cannabinoid product reached 40% for the THCA synthase reaction with a product ratio of THCA: CBCA of 2.2:1 (FIG. 20A). For the CBDA synthase reaction, 30.7% of CBGA was converted to cannabinoid products after 2 weeks with a CBCA:CBDA product ratio of 1.8:1 (FIG. 20B). As illustrated in FIG. 20B, THCA was produced as a minor product when CBDA synthase is used for bio-catalysis. The amount of THCA produced is about 0.8% of total cannabinoid products (FIG. 20B).

Example 9 Biphasic Oil-Aqueous Systems (1:1) Using CBGA as Substrate and Purified CBDA Synthase This experiment applied the same reaction conditions as Example 2 except that a purified CBDA synthase was used (instead of a lyophilized technical grade CBDA synthase). Methods to purify CBDA synthase are known in the art. In this experiment, the CBDA synthase was purified using ion exchange chromatography and Sepharose SP Fast Flow resin (GE healthcare life science).

Figure 21A:
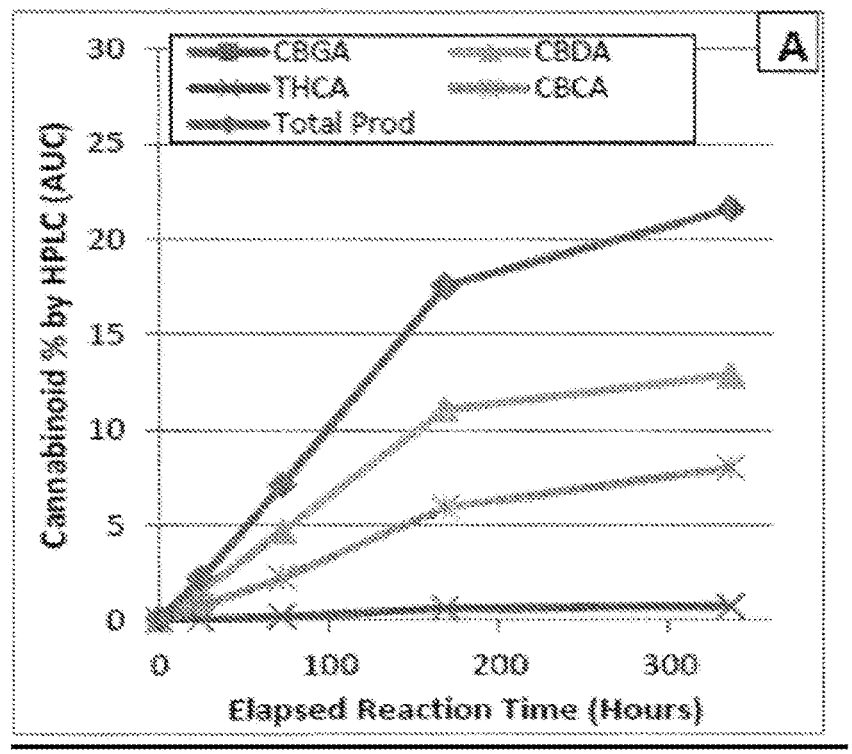
FIGS. 21A-21B depict the activity of purified CBDA synthase in a 1:1 biphasic oil-aqueous reaction with CBGA as substrate.
Figure 21B:
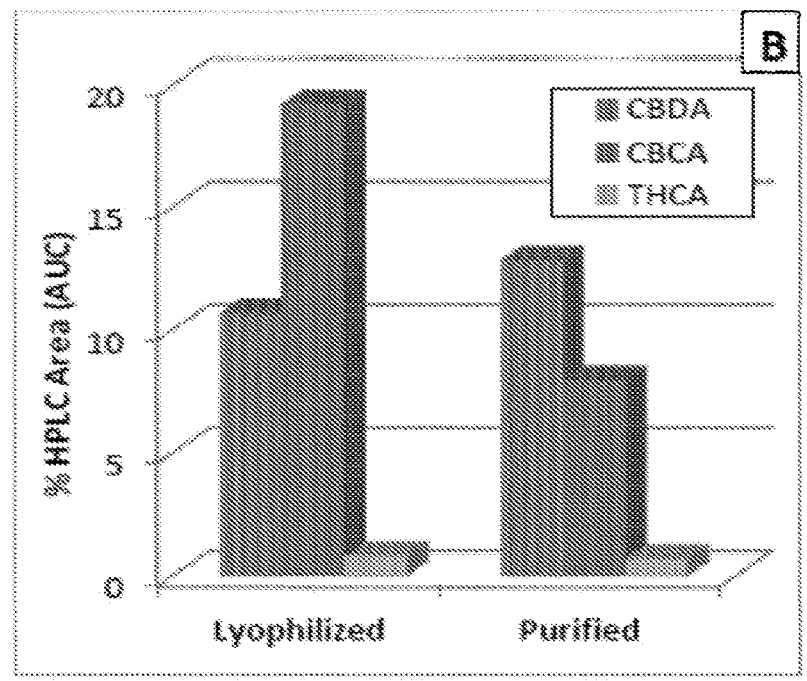

As illustrated by the graph in FIG. 21A, about 20% of the CBGA substrate is converted to cannabinoid products after 300 hours. Compared to crude lyophilized CBDA synthase, the purified CBDA synthase produced higher amounts of CBDA product with a CBDA:CBCA ratio of 2.1:1 after 2 weeks of reaction (FIG. 21B). The amount of CBDA produced after 2 weeks was 509.8 mg/L (data not shown). Purified enzyme may affect the cannabinoid product ratios.

Example 10 Effects of pH Values on the Production of Cannabinoids from Biphasic Systems This experiment evaluated the effect of pH (e.g., pH above 6.0) on the cannabinoid production in a biphasic oil-aqueous system. In order to more accurately observe the effect of pH on reaction kinetics, the amounts of loaded enzymes were lowered.

10× stock solutions were prepared for THCA synthase and CBDA Synthase in 5% DMSO, 95% deionized water. Enzyme stocks were diluted 1:10 using five buffers containing 100 mM sodium citrate and 5% DMSO at pH values of 4.0, 4.5, 5.0, 5.5, and 6.0. The final enzyme concentration in the aqueous layer was about 8.0 mg/mL in 5% DMSO and 95% sodium citrate buffer at variable pHs. 600 μL of soybean oil containing 5 mg/mL CBGA was overlaid onto 300 μL of aqueous phase containing crude lyophilized THCA synthase at each of the five pH values. Assays were conducted in 2 mL glass HPLC vials and placed on a vertical tube rotator at ambient temperature.

For each time point, samples of the oil phase were collected by removing the vials from the tube rotator and allowing them to separate for ~30 mins. Once clear separation was visible, 10 μL of oil was diluted in 190 μL of IPA, vortexed, and analyzed by HPLC.

Figure 22A:
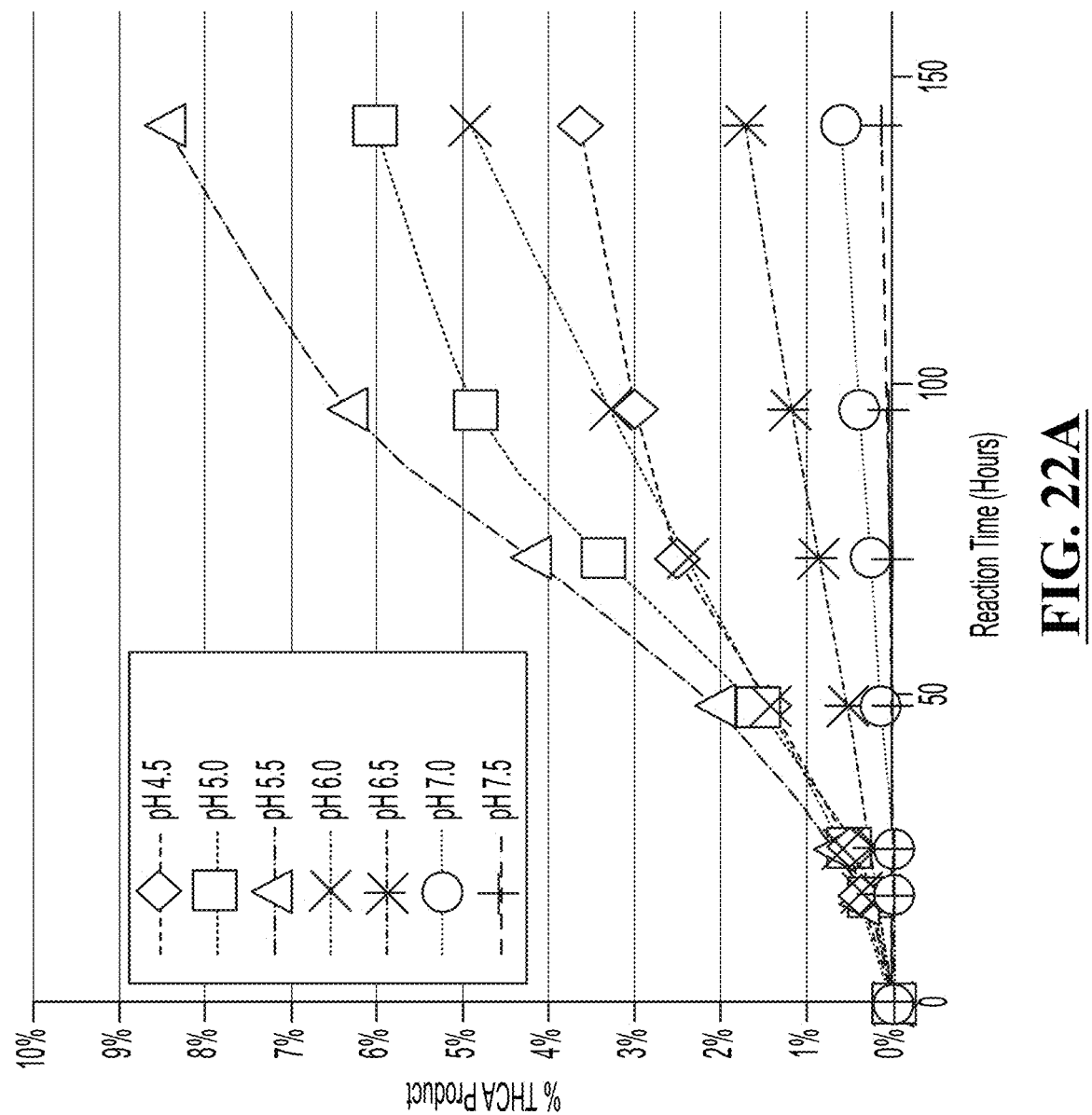
FIGS. 22A-22B and 23A-23B show effects of pH values on production of cannabinoids in 2:1 biphasic soybean oil-aqueous reactions with lyophilized THCA synthase. The aqueous phase contains 32 mg/mL lyophilized THCA synthase.
Figure 22B:
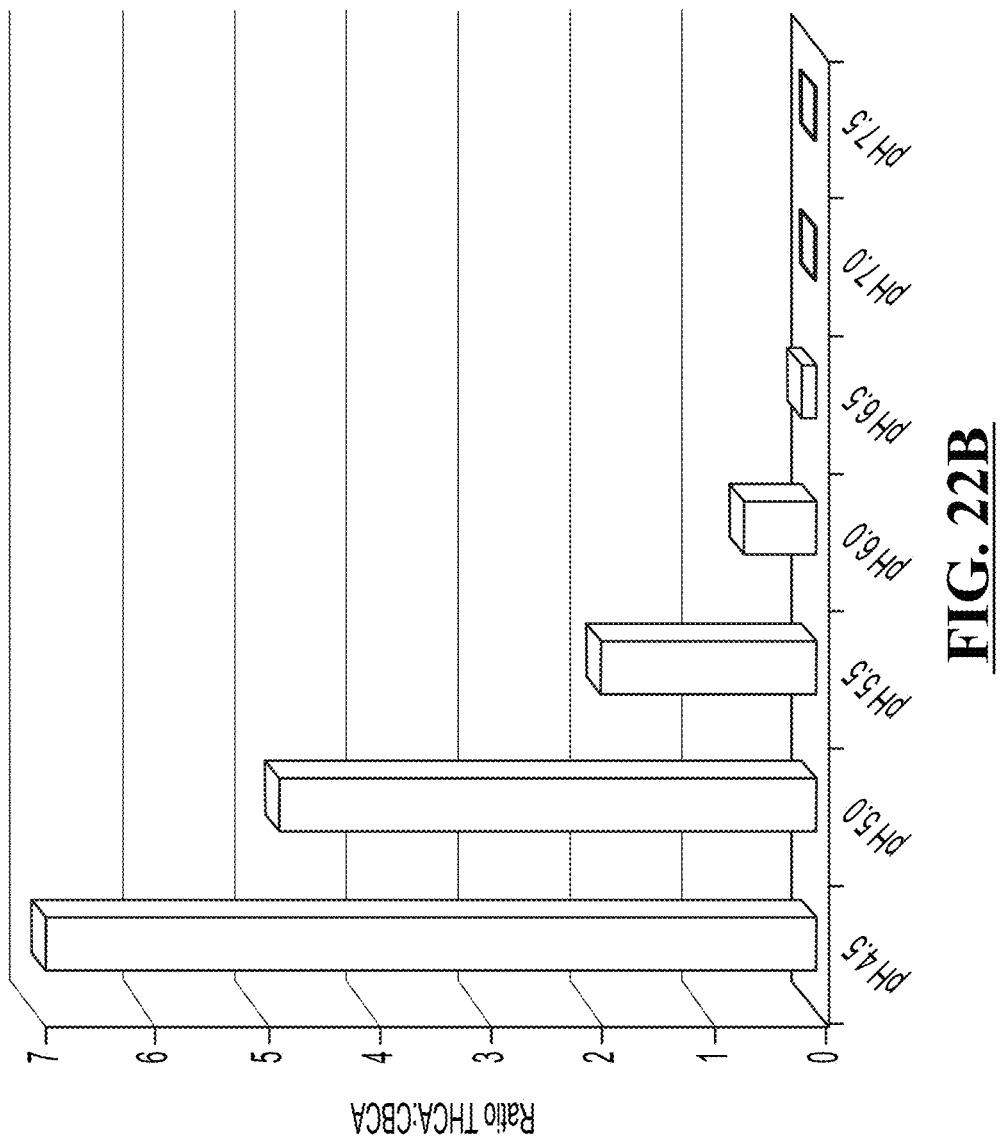
Figure 23A:
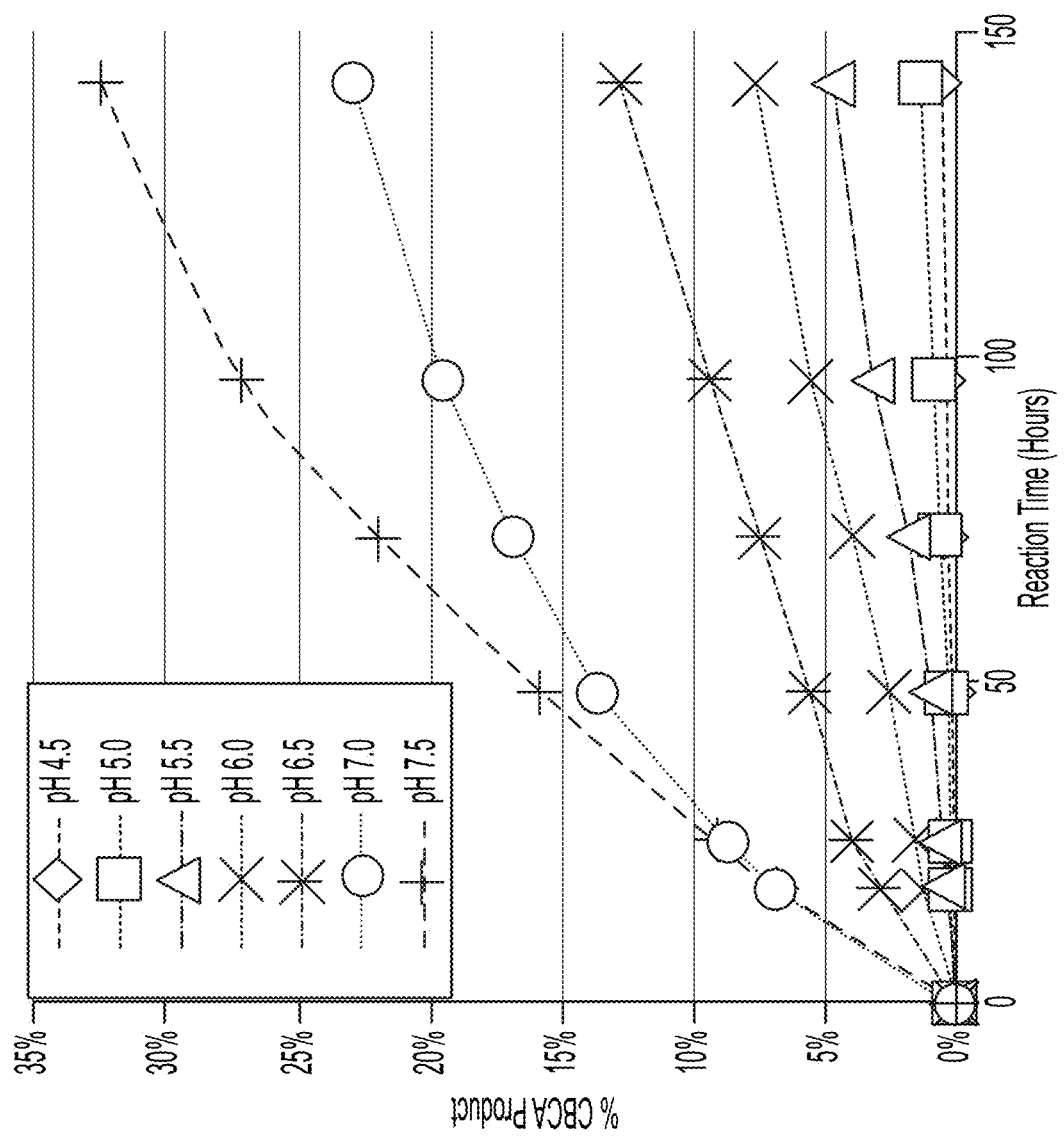
Figure 23B:
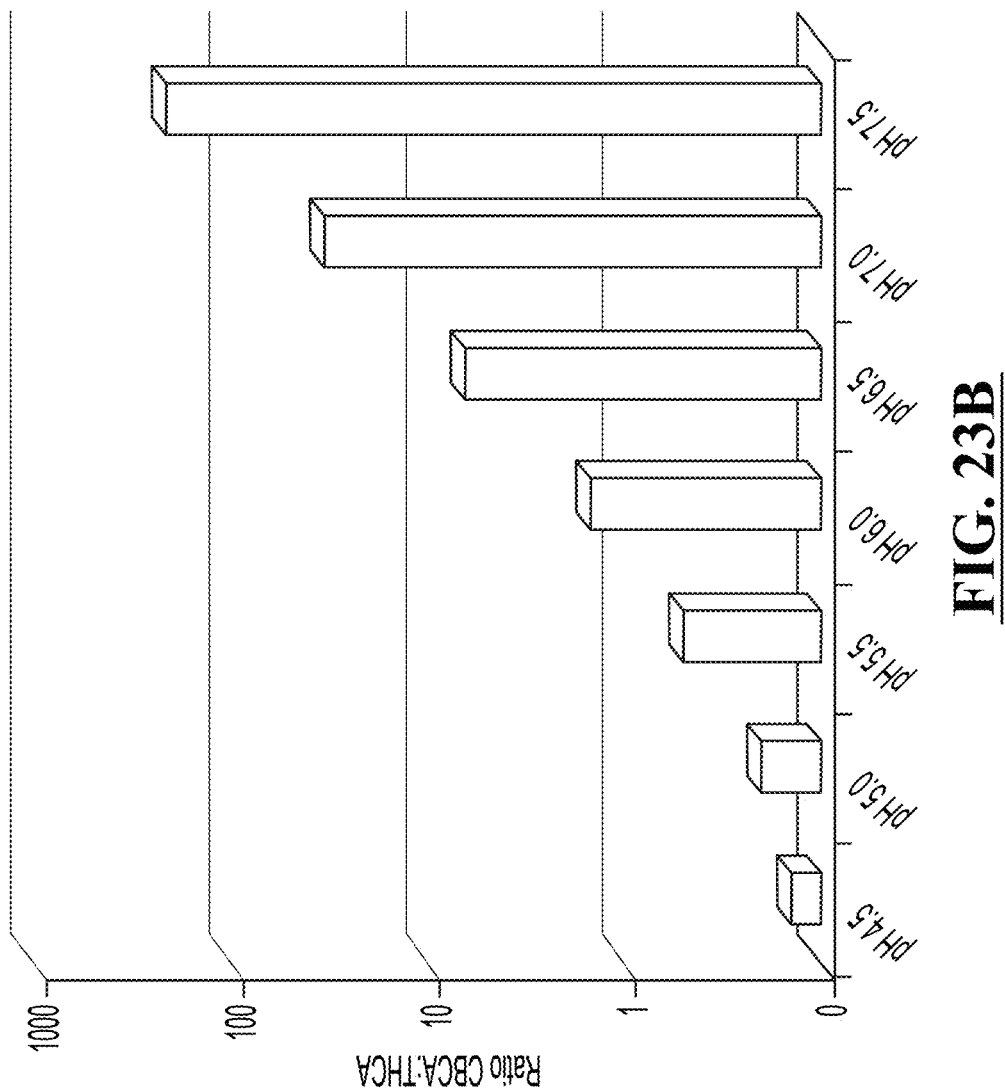

For each time point, samples of the oil phase were collected by removing the vials from the tube rotator. The results showed that among all of the pH values examined, the production of THCA reached its greatest at pH 5.5 (FIG. 22A), while the production of CBCA was the highest at pH 7.5 (FIG. 23A).

Example 11 Effects of Various Oil to Aqueous Phase Ratios on the Production of Cannabinoids in Biphasic Aqueous-Oil Systems This experiment was designed to investigate the effect of varying oil to aqueous ratios while keeping the absolute amount of CBGA and enzyme in the system constant. In this experiment, stock solutions of CBGA and lyophilized THCA synthase were prepared as shown in Table 1. The CBGA and THCA synthase solutions in oil and aqueous buffer were combined in the ratios listed in Table 1 using five separate 1 mL reaction vials. Each entry in Table 1 is carried out in duplicate (vial set A and vial set B).

TABLE 1

Experimental Conditions of oil-aqueous ratio assays

| | CBGA | | | Enzyme | | |
|---|---|---|---|---|---|---|
| Vial # | Concentration (mg/mL) | Volume (mL) | Total (mg) | Concentration (mg/mL) | Volume (mL) | Total (mg) |
| 1 | 60.61 | 0.33 | 20 | 60.61 | 0.66 | 40 |
| 2 | 50.00 | 0.4 | 20 | 66.67 | 0.6 | 40 |
| 3 | 40.00 | 0.5 | 20 | 80.00 | 0.5 | 40 |
| 4 | 33.33 | 0.6 | 20 | 100.00 | 0.4 | 40 |
| 5 | 30.30 | 0.66 | 20 | 121.21 | 0.33 | 40 |

All vials in set A were incubated at ambient temperature on a tube rotator spinning at 40 rpm and removed 30 minutes prior to sampling. A 10 μL sample was taken from the oil phase of each vial at each time point and combined with 190 μL of IPA, vortexed, and injected on the HPLC for analysis.

On the other hand, the vials in set B were allowed to incubate as described above, without sampling in the middle of reaction. At the end point for set B, which was determined by monitoring the reactions in set A, the vials in set B were extracted (total reaction extraction with 9 volumes of IPA). One 10 μL sample of oil phase was extracted prior to the total reaction extraction.

Figure 24:
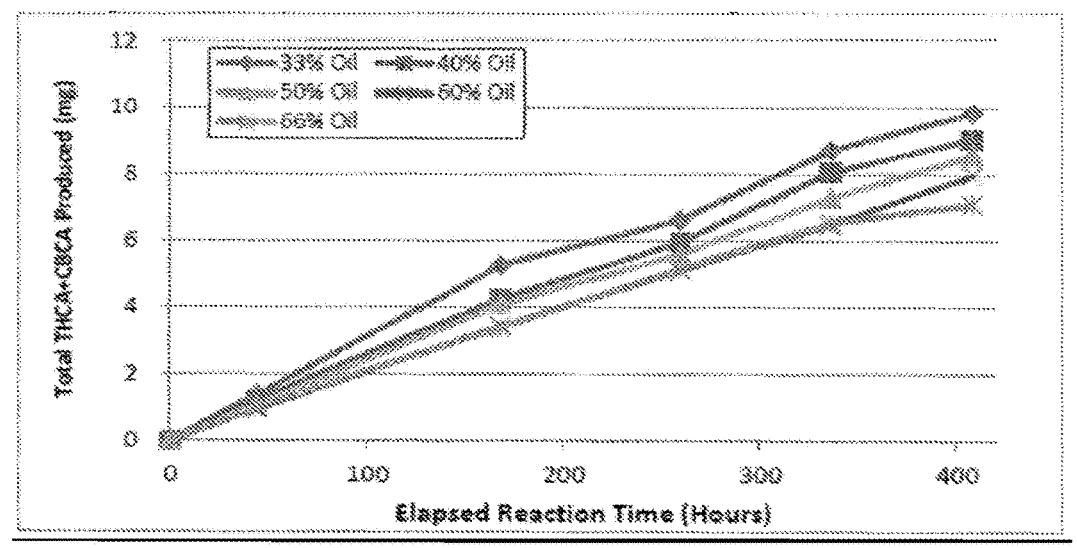
FIG. 24 shows the production of THCA and CBCA in biphasic oil-aqueous systems with different oil to aqueous ratios. All systems contain 20 mg of CBGA in soybean oil phase and 40 mg of Lyophilized Enzyme in 100 mM sodium citrate and 20% DMSO at pH 5.5.
Figure 25A:
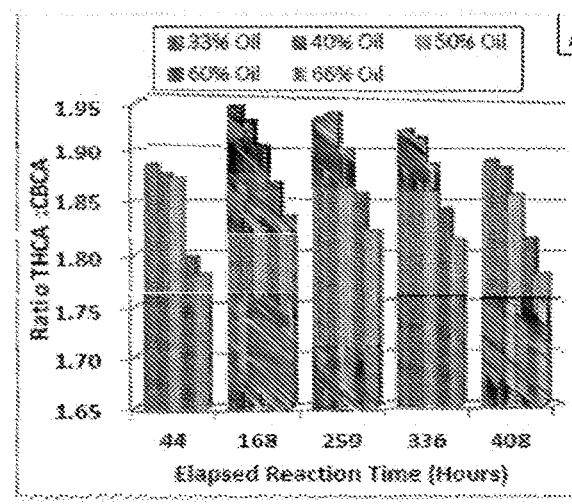
FIGS. 25A-25B shows ratios of reaction products in biphasic oil-aqueous systems with different oil:aqueous ratios. Ratios of products at each time point are shown in FIG. 25A. Ratios of products at 408 hours are shown in FIG. 25B.
Figure 25B:
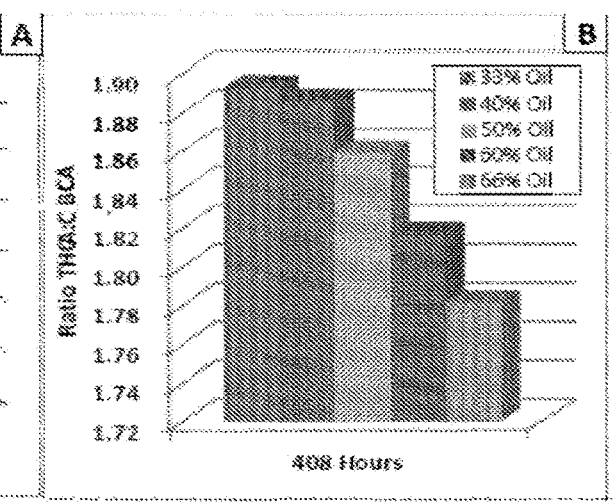

The ratio of oil to aqueous phase influenced the amount of cannabinoid products produced as well as the ratio of cannabinoid products produced using the biphasic system. As shown in FIG. 24, a biphasic reaction mixture comprising 33% oil and 66% aqueous buffer (1:2 oil-aqueous ratio) produced the maximum amount of total cannabinoid product (FIG. 24). Ratios of THCA:CBCA products at each time point are shown in FIG. 25A, while the ratios of THCA:CBCA products at 408 hours are shown in FIG. 25B.

Figure 26:
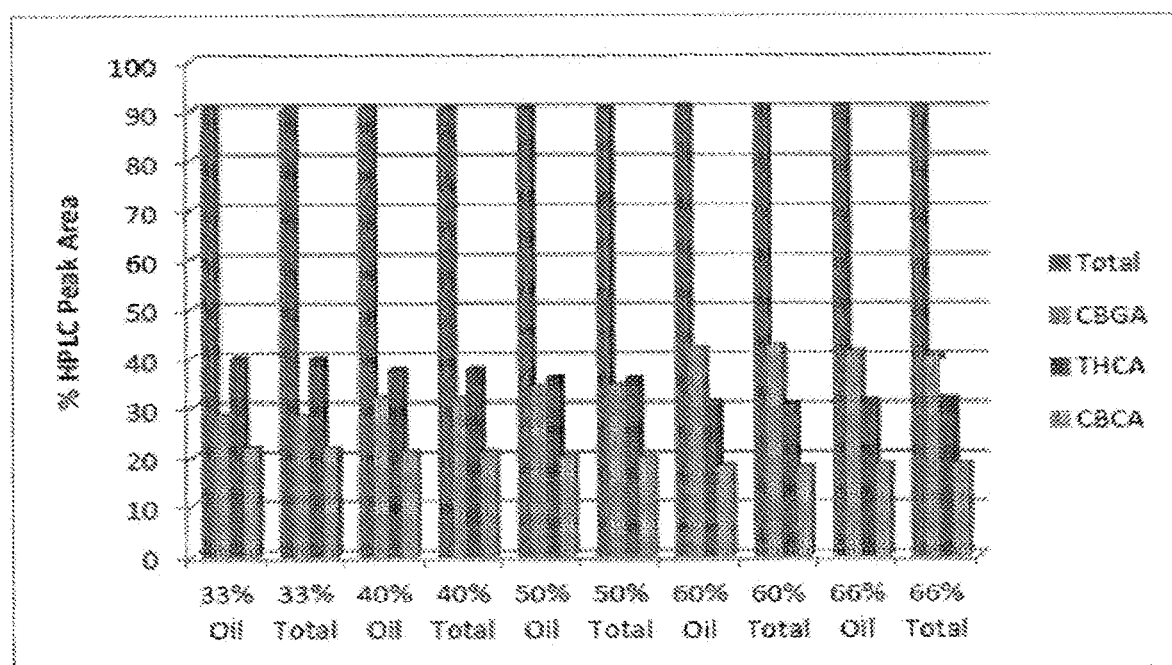
FIG. 26 shows percentage of each cannabinoid by HPLC Area % (AUC) for each oil:aqueous ratio when extracting just the oil layer vs. the total (oil and aqueous) assay with IPA.

For the vials in set B, the oil extract and total reaction extracts produced nearly identical percentage of CBGA and products (FIG. 26).

Figure 27:
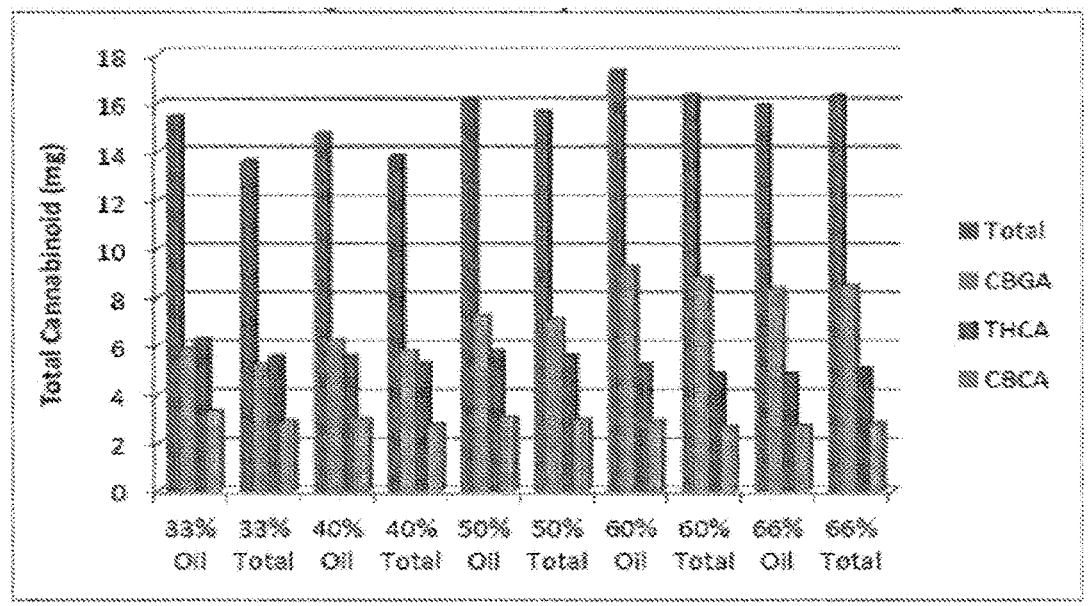
FIG. 27 shows the total amount of each cannabinoid (mg) for each oil:aqueous ratio when extracting just the oil layer compared to the total (oil and aqueous) assay with IPA.

Efficiency of bio-catalysis, at least based on mass balances was good. The slight difference between theoretical yields and actual yields may be due to errors introduced during the removal and transfer of solvents and reaction mixture. FIG. 27 illustrates the amounts of CBGA, THCA, and CBCA as well as total cannabinoid produced for each oil:aqueous buffer ratio. It is evident from this figure that the calculated sum of THCA, CBCA and CBGA for each oil to aqueous buffer ratio are not significantly different from the total cannabinoid content (blue bar) estimated using the total reaction extract (vial B).

Example 12 Activity of Purified THCA Synthase in (1:1) Biphasic Oil-Aqueous Systems with Varying pHs and DMSO Concentrations This experiment is designed to determine the effects of DMSO on the bioconversion of CBGA to THCA and/or CBCA at pH 5.5 and pH 7.5 using a purified enzyme preparation.

Figure 28A:
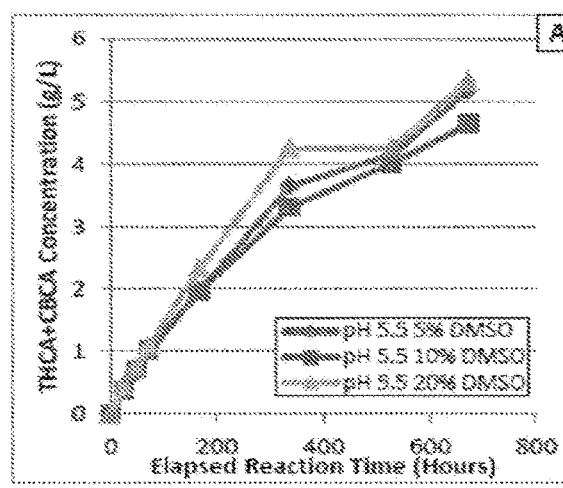
FIGS. 28A-28B and 29 show production of cannabinoids in 1:1 biphasic oil-aqueous reactions with purified THCA Synthase at different pH (pH 5.5 for FIG. 28 and pH 7.5 for FIG. 29) and different concentration of DMSO.
Figure 28B:
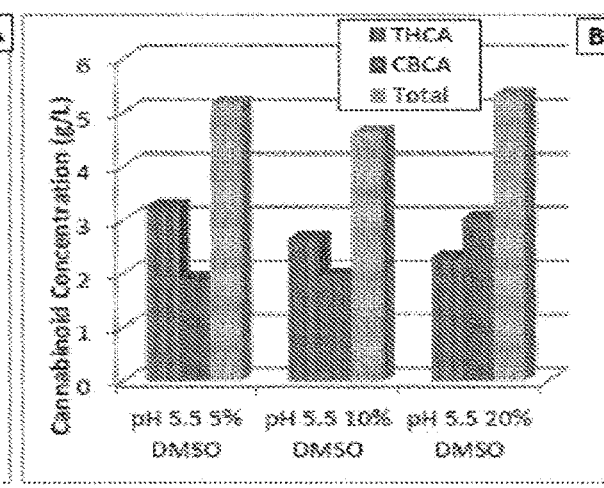

In the first experiment, the aqueous phase contains 0.1 M citrate buffer, 270 μg/mL purified THCA synthase with 5%, 10%, or 20% DMSO at pH 5.5. The soybean oil phase contained 20 g/L CBGA. FIG. 28A shows the total amount of cannabinoid product that accumulates over time. FIG. 28B shows the amounts of THCA, CBCA, and the combination of THCA and CBCA that is produced for each concentration of DMSO after 672 hours.

Figure 29:
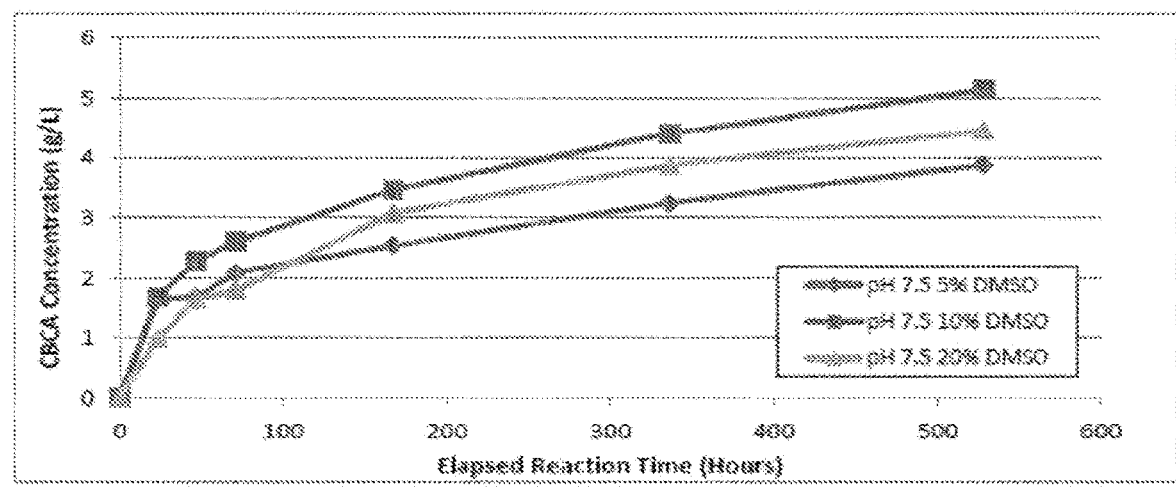

In the second experiment, the aqueous phase contains 0.1 M HEPES buffer and 270 µg/mL purified THCA synthase with 5%, 10%, or 20% DMSO at pH 7.5. The soybean oil phase contains 20 g/L CBGA. At pH 7.5, the conversion continues to progress 500 hours after initiation of biocatalysis. The greatest amount of CBCA was produced in the reaction with 10% DMSO (FIG. 29).

Example 13 Activity Purified THCA Synthase in Biphasic Oil-Aqueous Systems (1:1) with Lower Amounts of DMSO Co-Solvent or in the Presence of Methanol Concentrations as Co-Solvent This experiment was designed to evaluate the effect of low amounts of DMSO or methanol on biocatalysis using CBGA and purified THCA synthase. The 1:1 biphasic oil-aqueous reactions contained 272 µg/mL purified THCA synthase in 100 mM citrate buffer and various amounts of DMSO or methanol at pH 5.5. The oil phase contains 10 g/L CBGA.

Figure 30:
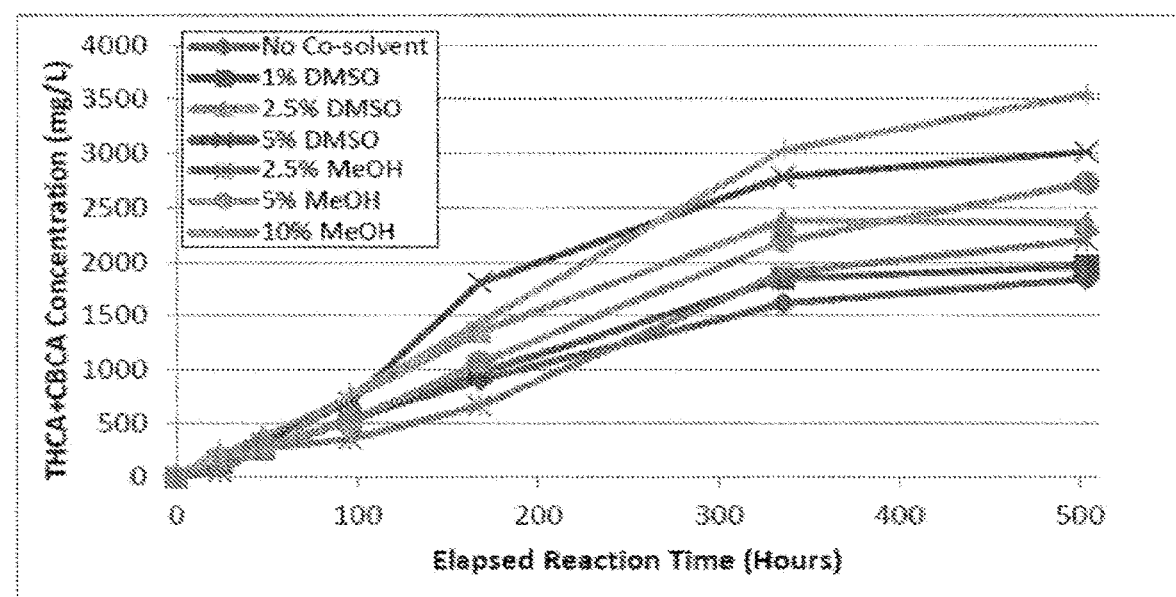
FIGS. 30 and 31A-31B show the activities of purified THCA synthase in biphasic oil-aqueous systems (1:1) with lower DMSO concentrations.
Figure 31A:
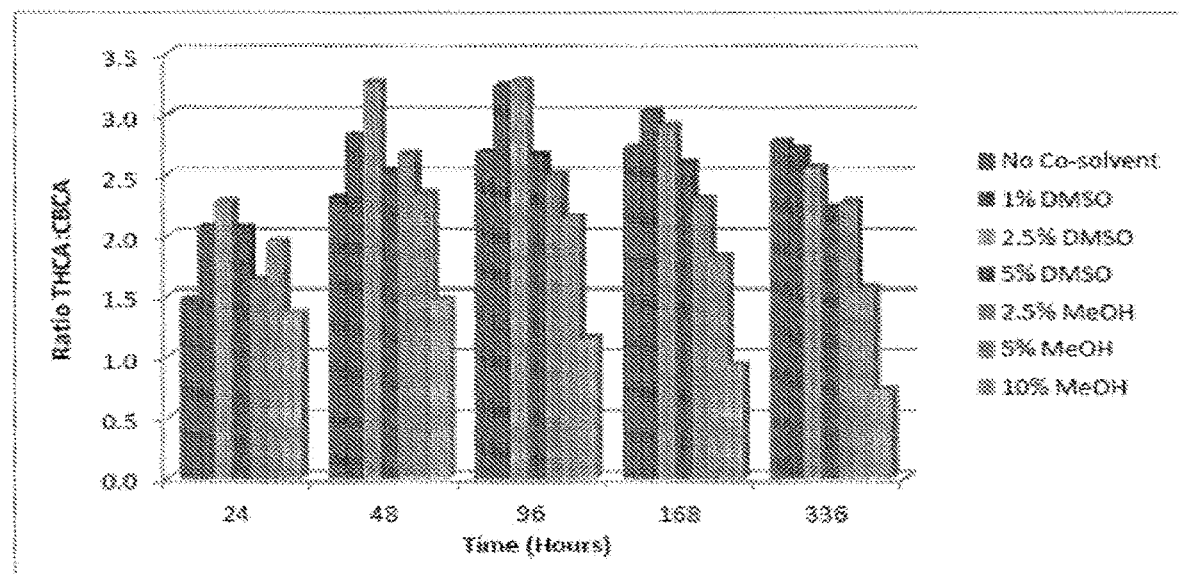
Figure 31B:
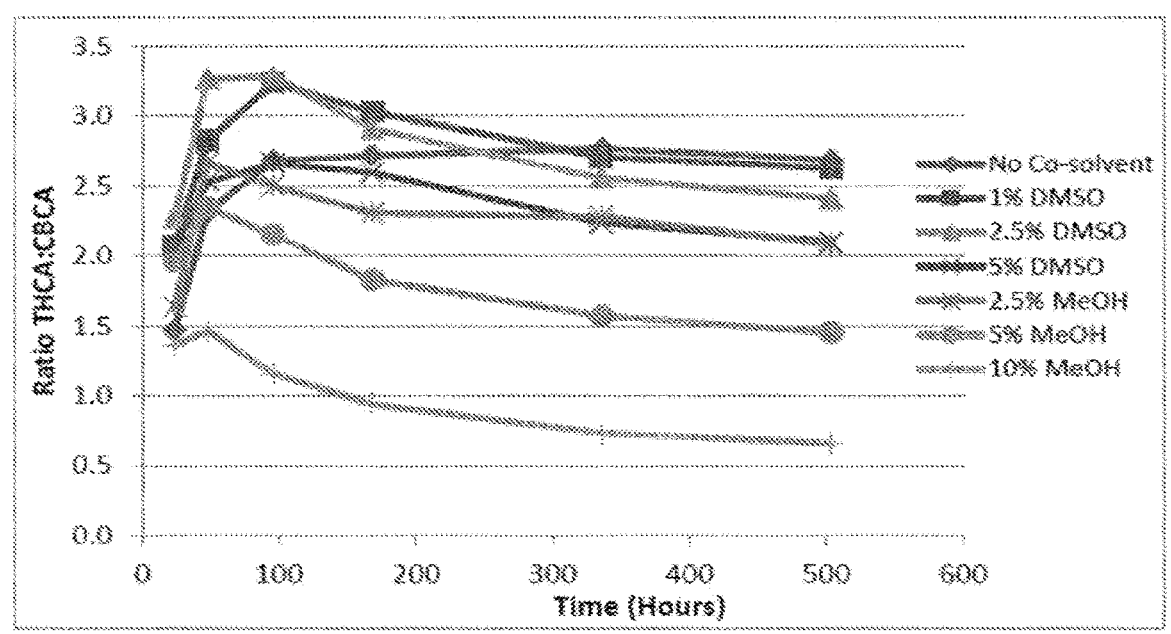

As shown in FIG. 30, the reaction containing 10% methanol produced the highest amount of total cannabinoids, although this condition produced the lowest ratio of THCA to CBCA (FIG. 31A and FIG. 31B).

Figure 13B:
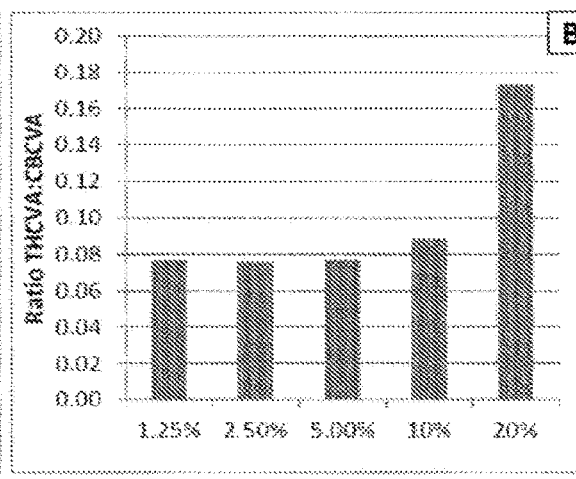

Also, the reaction solutions with 5% and 2.5% DMSO produced amounts of total cannabinoids that are comparable to the 10% methanol reaction solution (FIGS. 13A-13B), but with much higher ratio of THCA to CBCA at about 2.5:1, compared with 0.7:1 for the 10% methanol reaction solution (FIG. 31A and FIG. 31B).

Example 14

Reaction of CBGA cyclization catalyzed by CBDA synthase was studied in aqueous solutions over a broad range of reaction times and concentrations of organic co-solvents, methanol and DMSO (from 1 to 20%, v/v). The reactions were stopped by quenching with equal volume of MeOH after 20 minutes, 40 minutes, 1 hour, 2 hours, 3 hours, 5 hours, and 23 hours and the reaction products were analyzed on LC-MS/MS. A typical UV-HPLC trace showing major reaction products is presented in FIG. 32.

The reaction solution contained 0.1 M citrate buffer, 20 mg/mL CBDA synthase, 0.2 mg/mL CBGA at pH 4.5, and with different volume percentages of DMSO or methanol (MeOH). Here, CBGA was introduced into the reaction from a 100-fold dilution of stock solution in MeOH (20 mg/mL) that introduced 1% (v/v) MeOH into the reaction. The 1 mL reaction solutions in glass vials were shaken at 75 rpm in Precision Scientific thermostat water bath at 25° C.

Figure 32:
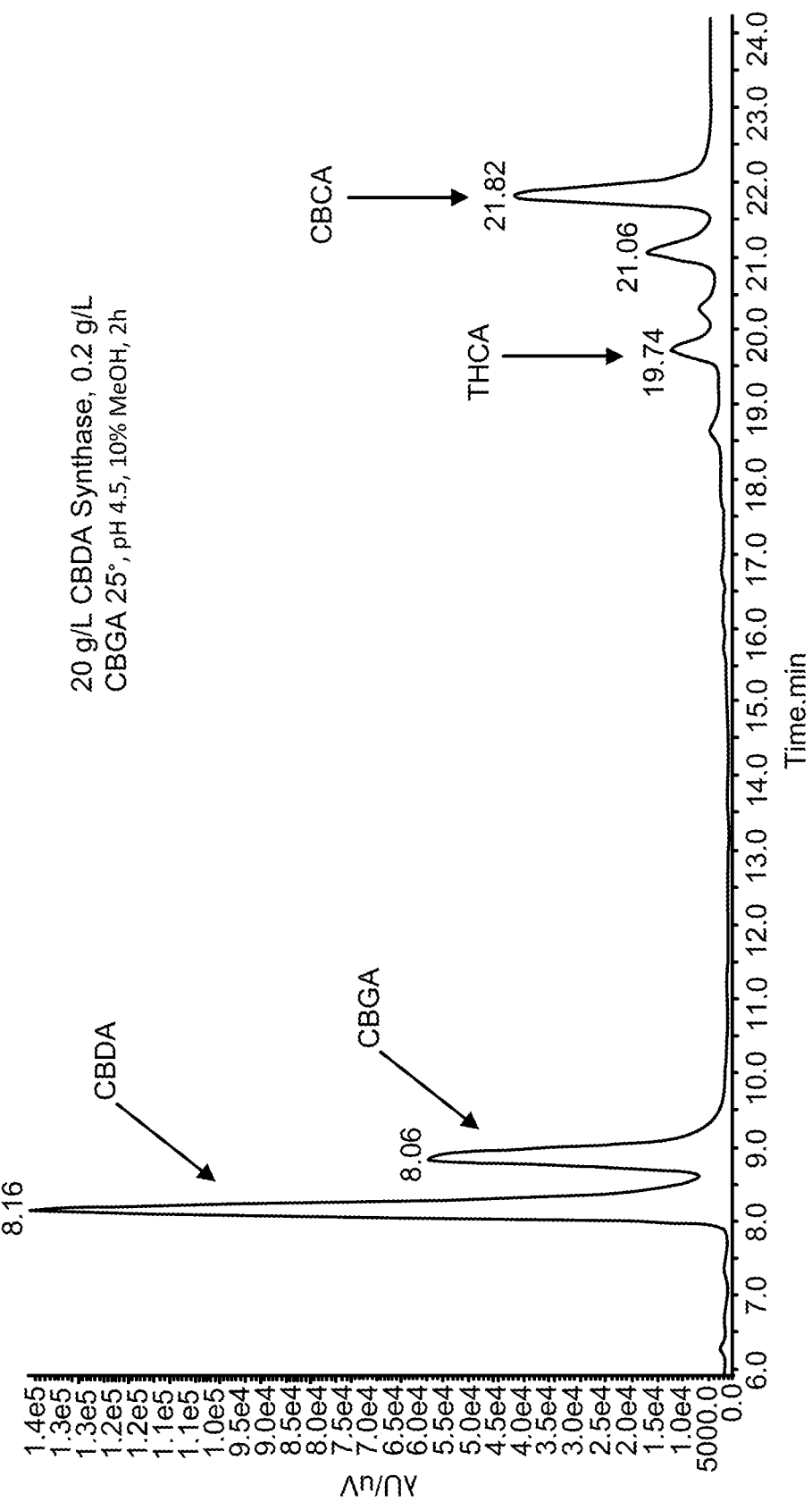
FIG. 32 shows the ratios of THCA to CBCA.

After different incubation time, aliquots of each reaction (0.1 mL) were diluted 2-fold by mixing with 0.1 mL MeOH; centrifuged at 4° C. at 9,990 rpm and supernatant was injected in LCMS for the product determination. FIG. 32 shows the UV-HPLC trace of products in the presence of 10% (v/v) MeOH after two hours.

Figures 33A, 33B:
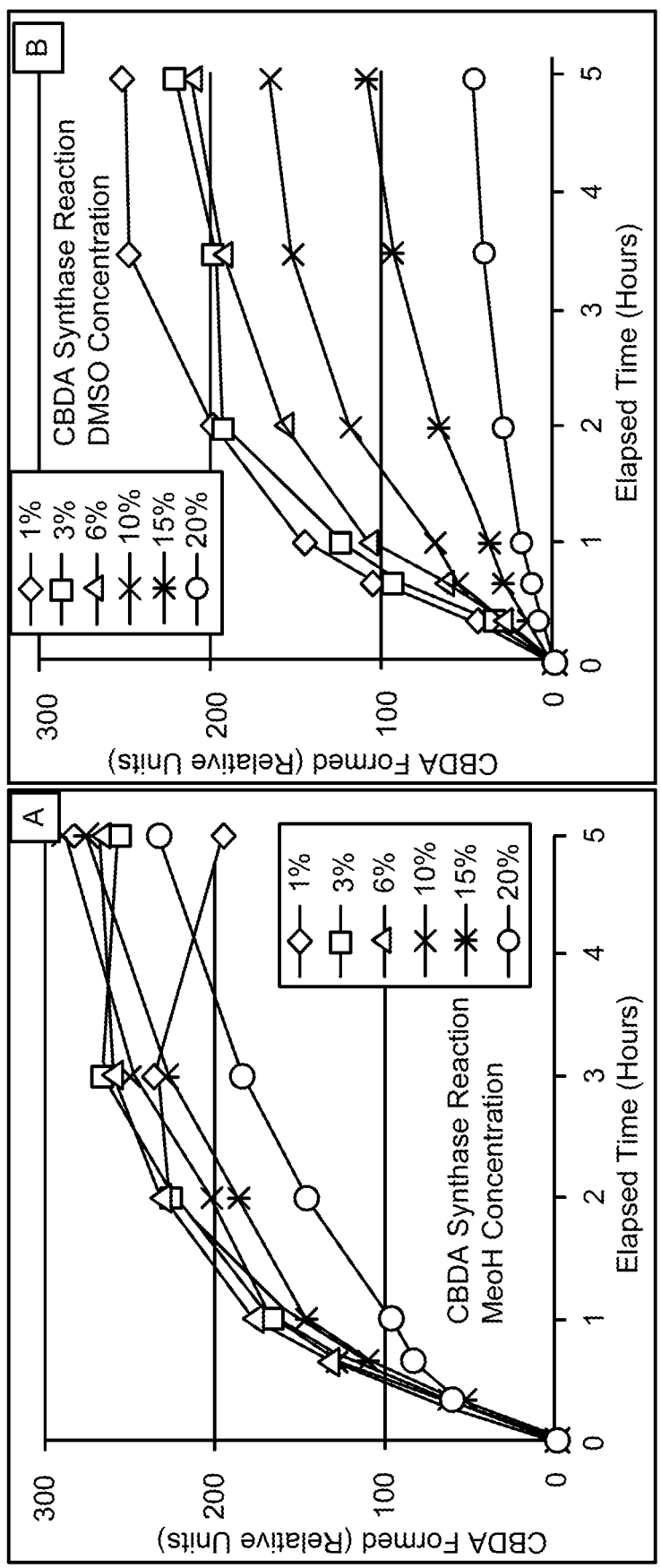

As shown in FIGS. 33A-33B, generation of CBDA follows linear kinetics under all solvent conditions for at least first 30 minutes of the reaction. Kinetics of CBDA formation is not significantly influenced by the presence of methanol up to 15% (v/v). Addition of 20% (v/v) methanol produces some suppression of the reaction as shown in the lower curve of FIG. 33A. Increasing concentrations of DMSO significantly decreases the rate of CBDA accumulation (FIG. 33B).

Also, THCA was produced as a minor product in the reaction catalyzed by CBDA synthase in comparison with CBDA (FIGS. 34A-34B). An increase in the concentration of methanol results in increased production of THCA (FIG. 34A). Conversely, an increase in the concentration of DMSO results in decreased production of THCA (FIG. 34B).

The rapid production of CBCA is shown in FIGS. 35A and 35B. Comparing FIG. 35B to FIG. 35A, DMSO was more efficient in catalyzing the production of CBCA with higher percentages of co-solvents DMSO and methanol.

Example 15 THCA Synthase Activity after Lyophilization

First, THCA synthase from an IEX resin was lyophilized and stored at −20° C. One month later, one vial of the lyophilized enzyme was removed from the freezer, warmed to room temperature, and dissolved and reconstituted in 1 mL of deionized water. 0.9 mL of reconstituted enzyme solution was added to 0.1 mL of 1.0 mg/mL CBGA stock in DMSO, mixed briefly, and placed on a tube rotator at ambient temperature. The activity of enzyme was monitored over 2 hours with samples taken at 15, 30, 60, and 120 minutes. Samples (100 µL) were extracted with an equal volume of methanol, centrifuged, and analyzed by HPLC.

Figure 36:
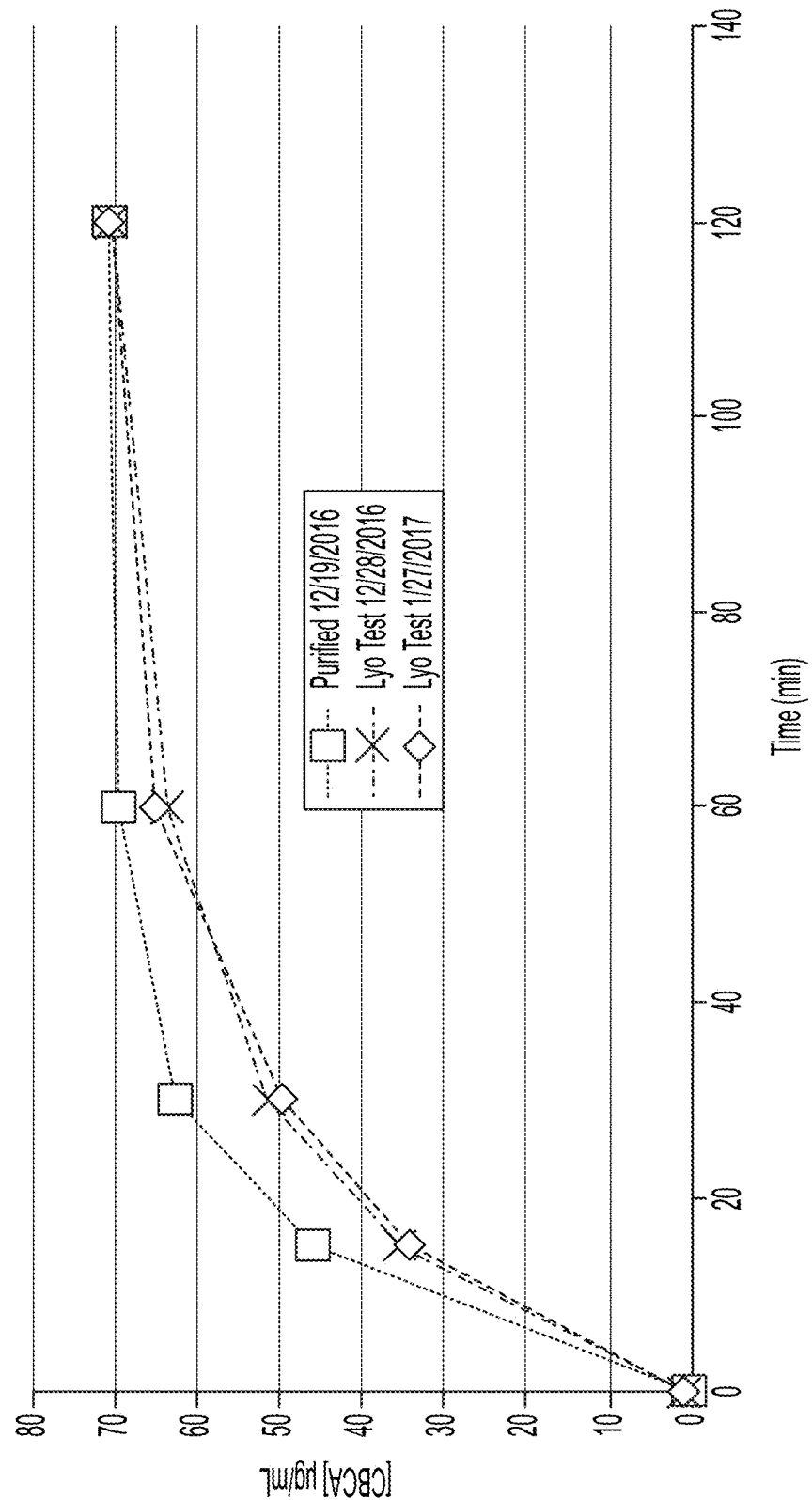
FIG. 36 shows the THCA synthase activity after lyophilization.

As shown in FIG. 36, the lyophilized THCA synthase retains its catalytic activity after one year of storage.

Example 16 Stability of CBDA Synthase in the Presence of Polar Co-Solvents

The effects of varying concentrations of co-solvents (methanol or DMSO) on the stability of CBDA synthase were evaluated. Here, 20 mg/mL CBDA synthase was incubated in 100 mM citrate buffer (pH 4.5) in the presence of different volume percentages of polar co-solvents (MeOH and DMSO). The solutions were shaken at 75 rpm in Precision Scientific thermostated water bath at 25° C. After different time intervals, CBGA was introduced by mixing aliquot of 100-fold concentrated stock solution of CBGA in MeOH (20 mg/mL) with aliquot of incubated enzyme. After incubation for 30 minutes, the reactions were stopped by mixing with an equal volume of MeOH (2-fold dilution), centrifuged at 4° C. at 9990 rpm and supernatant was injected in LCMS for determination.

Figure 37B:
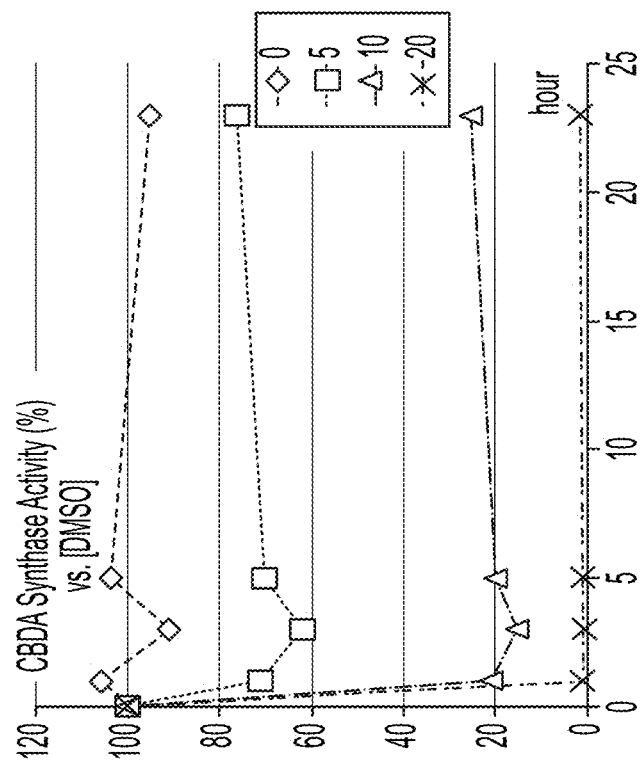
FIGS. 37A-37B shows stability of CBDA synthase (20 mg/mL) after incubation in 0.1 M citrate buffer, pH 4.5, in the presence of different concentrations of polar co-solvents.
Figure 37A:
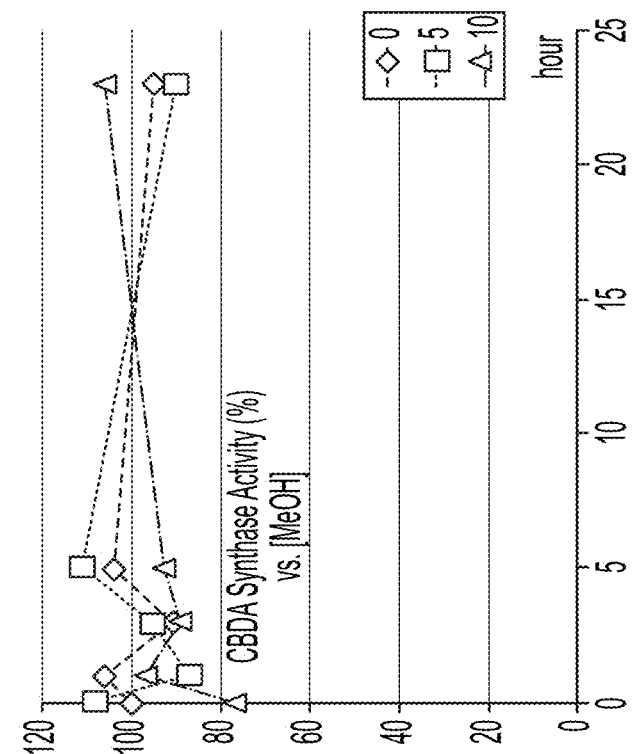

Changes in the activity of CBDA synthase after incubation (for up to 23 hours) at pH 4.5, 25° C., with different concentrations of MeOH (up to 10%, v/v) and DMSO (up to 20%, v/v) are shown in FIGS. 37A and 37B, respectively.

Incubation with methanol, prior to measuring enzyme activity of CBDA synthase, did not produce significant effect on the activity of the enzyme (FIG. 37A). In contrast, the addition of DMSO prior to activity measurements significantly reduced the activity of CBDA synthase, and the effect was more pronounced at higher DMSO concentrations. Incubation with 20% (v/v) DMSO resulted in almost complete loss of the enzyme activity. Inactivation of CBDA synthase by DMSO was rapid, as after the first hour of incubation the enzyme activity loss was significant and did not change much after the following incubation with DMSO up to 23 hours (FIG. 37B). A similar result was observed for THCA synthase (data not shown).

Example 17 Biphasic Oil-Aqueous Systems Using CBGA as Substrate and THCA Synthase In a biphasic oil-aqueous reaction, the oil phase contained 36 g/L CBGA. The aqueous phase contained THCA synthase. The pH in the aqueous phase was optimized for CBCA production. The total volume reaction (including both oil and aqueous phases) was incubated on the tube rotator. At each time point indicated in FIG. 38, the samples of the oil phase were collected by removing the vials from the tube rotator and allowing them to separate. Once a clear separation was visible, the oil aliquot was diluted in IPA, vortexed, and analyzed by HPLC.

The reaction resulted in a rapid, high conversion (above 95%) of CBGA to the cannabinoid products (THCA and CBCA) within about 160 hours since the reaction started. With its high volumetric efficiency, the biphasic system produced about 30 g/L of cannabinoid products (about 29 g/L CBCA and about 2 g/L THCA) with the excellent product ratio of CBCA to THCA (>40:1) in the final products (FIG. 38).

Figure 39:
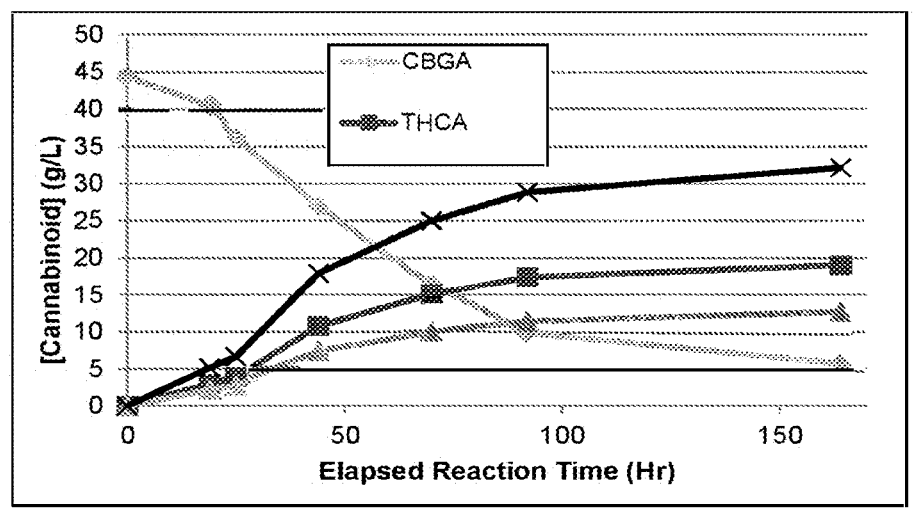

In a separate biphasic oil-aqueous reaction, the oil phase contained 44 g/L CBGA as substrate and the aqueous phase contained THCA synthase. The pH in the aqueous phase was optimized for THCA production. The total volume reaction (including both oil and aqueous phases) were incubated on the tube rotator. At each time point indicated in FIG. 39, the samples of the oil phase were collected by removing the vials from the tube rotator and allowing them to separate. Once a clear separation was visible, the oil aliquot was diluted in IPA, vortexed, and analyzed by HPLC. This reaction also resulted in a rapid, high conversion (above 90%) of CBGA to the cannabinoid products (THCA and CBCA) within about 160 hours, and produced more than 30 g/L of cannabinoid products (about 19 g/L THCA and about 13 g/L CBCA) (FIG. 39). The large amount of cannabinoid products suggested a high volumetric efficiency of this biphasic reaction.

Example 18 Biphasic Oil-Aqueous Systems Using CBGA as Substrate and CBDA Synthase In a biphasic oil-aqueous reaction, the oil phase contained 20 g/L CBGA substrate and the aqueous phase contained CBDA synthase. The pH in the aqueous phase was optimized for CBDA production. The total volume reaction (including both oil and aqueous phases) was incubated on the tube rotator. At each time point indicated in FIG. 40, the samples of the oil phase were collected by removing the vials from the tube rotator and allowing them to separate. Once a clear separation was visible, the oil aliquot was diluted in IPA, vortexed, and analyzed by HPLC.

Figure 38:
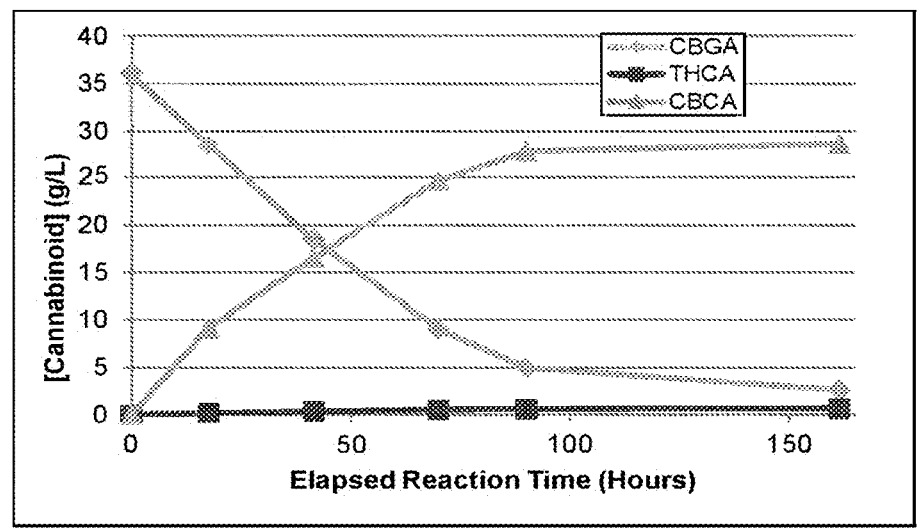
FIGS. 38 and 39 depict the activities of THCA synthase in biphasic oil-aqueous reactions with CBGA as substrate. In those experiments, pH was optimized for formation of CBCA (FIG. 38) and THCA (FIG. 39), separately.
Figure 40:
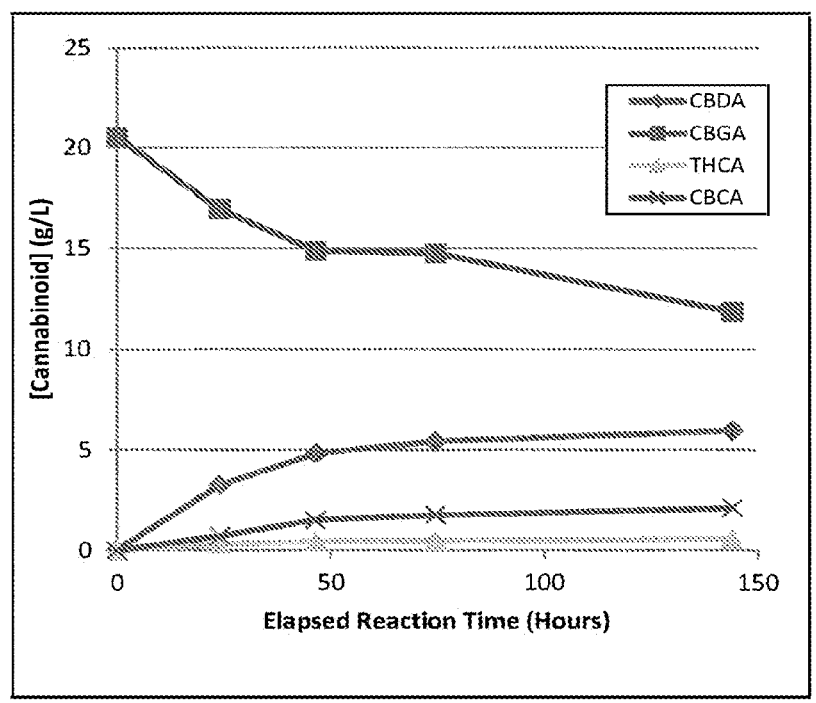
FIG. 40 depicts the activity of CBDA synthase in a biphasic oil-aqueous reaction with CBGA as substrate.
Figure 41:
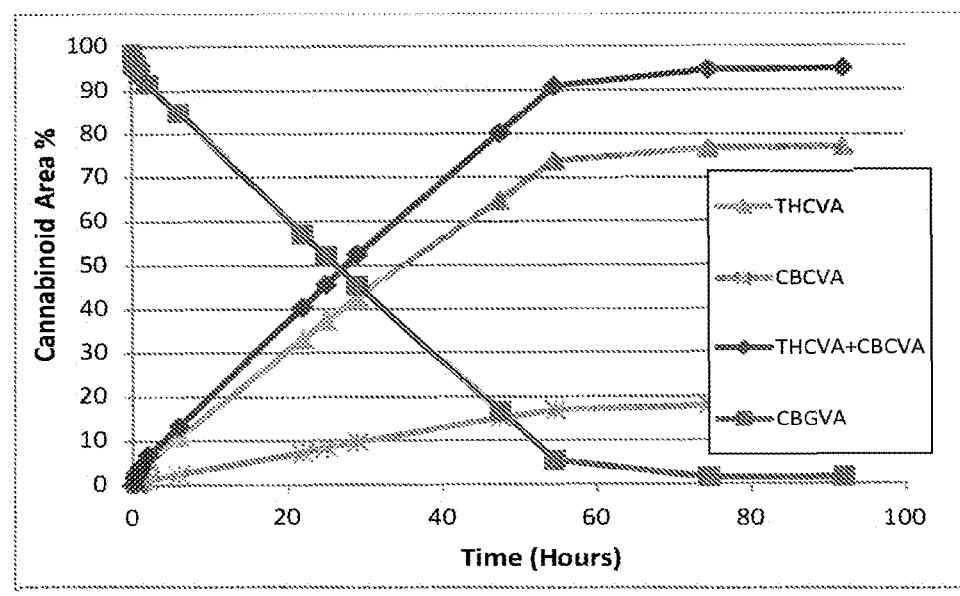
FIG. 41 shows kinetics of conversion of CBGVA to THCVA and CBCVA in the 3 L reaction.

The reaction with CBGA substrate (FIG. 40) was still efficient in producing cannabinoid products, although it is slightly slower and has a lower volumetric efficiency than the above reactions with THCA synthase (FIG. 38). At 140 hours post-reaction, about 50% of CBGA substrate was converted to cannabinoid products (>9 g/L), among which the CBDA product was about 6 g/L and the CBCA product was about 2 g/L (FIG. 40). The cannabinoid compounds were well resolved by RP-HPLC as shown in FIG. 41.

Example 19 Biphasic Oil-Aqueous Systems in a Scale-Up Reaction

The bioconversion reaction of CBGVA to THCVA and CBCVA with THCA synthase was performed in a scale-up reactor (a 3 L stirred-tank reactor). Example 2 showed an efficient conversion of CBGVA to THCVA and CBCVA using tech-grade lyophilized THCA synthase in a small scale reaction (3 mL total volume) (FIG. 5A). This scale-up reaction was conducted to demonstrate the ability to conduct the reaction on 30 g of cannabinoid substrate using THCA synthase enzyme at 100 g/L.

CBGVA Solution in Oil Phase

1 L of soybean oil and 35 g of CBGVA were mixed in substrate in a 2 L bottle on an orbital shaker at 37° C. and 120 rpm over two days, after which the CBGVA solution in soybean oil appeared hazy and exhibited some brown insoluble clumps at the bottom and brown insoluble material adhered to the glass of the bottle. The solution was centrifuged in a Sorvall RC5C floor centrifuge at 9,000 rpm for 10 minutes to clarify the solution.

The CBGVA solution was analyzed by a HPLC machine, which estimated the concentration to be 26 g/L. Additional solution with 7 g of CBGVA was solubilized in 200 mL of soybean oil after overnight shake and centrifuge and was added to the initial CBGVA solution to make the batch concentration. The combined CBGVA solution had an estimated concentration at 28 g/L based on the HPLC analysis.

3 L Reaction System

The 3 L bioreactor components were assembled with agitation, pH control, and temperature control. The reactor vessel was placed on a support ring attached to a scaffold and secured with two large chain clamps. Rushton impellers were secured to the Teflon-coated stir shaft, with the lower impeller 3 cm above the bottom of the shaft, and the top impeller positioned so that it was just above the 2 L mark on the reactor. The top of the stir shaft was passed through the center opening of the head plate and secured in a variable-speed stirring mechanism attached to the support scaffold. The headplate was clamped in position with the quick-release clamp. The reactor jacket inlet and outlet were attached to the temperature control unit.

A glass addition funnel was secured to the support scaffold with two large chain clamps, size 16 Pharmed tubing was attached to the stopcock, and the tubing was run through a Watson-Marlow 120 U/DV benchtop peristaltic pump. This pump was connected to the pH controller and set to a deadband of +/−0.05 pH units. 2 N HCl was added to the funnel and the line was primed. The pH probe was connected to the pH monitor/controller and calibrated using both pH 7 and pH 4 buffers.

THCA Synthase in Aqueous Phase

2 L of 100 mM sodium citrate buffer (pH 5.0) and 10% DMSO (v/v) were prepared as follows:
1. Dissolving 13.45 g of anhydrous citric acid (Fisher A940-1) in 700 mL of deionized water to make a 100 mM solution;
2. Dissolving 38.23 g of sodium citrate dihydrate (Sigma W302600-1KG-K) in 1.3 L of deionized water to make a 100 mM solution;
3. Mixing the citric acid and sodium citrate solutions, removing 200 mL solution, and adding 200 mL of DMSO (Sigma 276855-1L); and
4. Mixing DMSO within the solution and adjusting pH to 5.0 with 2 N HCl.

200 g of tech-grade THCA synthase (BPD1090-F500) was added with 1.6 L of citrate buffer into a 5 L bucket. The solution with THCA synthase was mixed with a spatula.

Bioconversion Reaction

The aqueous solution with the THCA synthase (100 g/L THCA synthase in 100 mM sodium citrate buffer with 10% DMSO and pH 5.0) was introduced to the 3 L bioreactor through the headplate using a funnel with the start stirring speed at 250 rpm. The remaining 400 mL of citrate buffer was used to rinse the bucket and added into the reactor. A pH probe was inserted and clamped into position. The enzyme solution was warmed to 37° C. An activated pH control pump brought the pH to the bottom of the deadband (pH 4.95). 1.1 L of CBGVA substrate in soybean oil was added to the reactor using a long-stemmed glass funnel. All unused ports were capped. Parafilm was applied around pH probe and stir shaft to minimize evaporation.

The bioconversion reaction was monitored with the following sampling procedure:

Pausing the mixing process to allow the reactor to sit for one minute;

Sampling the upper phase via a serological pipette (~1 mL removed) and resuming the mixing process;

Centrifuging the sample at 20,800 rpm in a 1.5 mL tube for 5 minutes to facilitate clear separation of oil and aqueous phases;

Sampling the oil phase, diluting the sample in 1:50 with IPA, and analyzing the sample by HPLC as shown in table 2.

TABLE 2

HPLC analysis
XSELECT CSH Fluoro-Phenyl 3.5 μm 4.6 × 100 mm Column
10 μL injection volume
Solvent A: Water with 0.1% Formic Acid
Solvent B: Acetonitrile with 0.1% Formic Acid

| Time (minutes) | Solvent B % |
|---|---|
| 0 | 57 |
| 12 | 57 |
| 13 | 95 |
| 15 | 95 |
| 16 | 57 |
| 17 | 57 |

Flow rate = 1.0 mL/min,
Temperature = 30° C.

The conversion of CBGVA to THCVA and CBCVA progressed at a steady rate over a period of 55 hours, after which conversion levelled off. FIG. 41 shows the conversion of CBGVA to THCVA and CBCVA, as measured by percentage of HPLC peak area at 267 nm. At 92 hours, once it was verified that the reaction was completed, the reactor was harvested and extracted. Nearly all of the CBGVA substrate was converted, with <2% remaining based on the HPLC peak area. In the products, THCVA accounted for 77% of the HPLC peak area at the end of the reaction; CBCVA accounted for 18% of the HPLC peak area at the end of the reaction. The rate of conversion of CBGVA levelled off significantly after 54.5 hours, with ~5% remaining. The reaction could have been harvested at this point, but it was allowed to progress to completion to minimize interference from CBGVA in downstream purification (and to determine the maximum level of conversion achievable).

Figure 42:
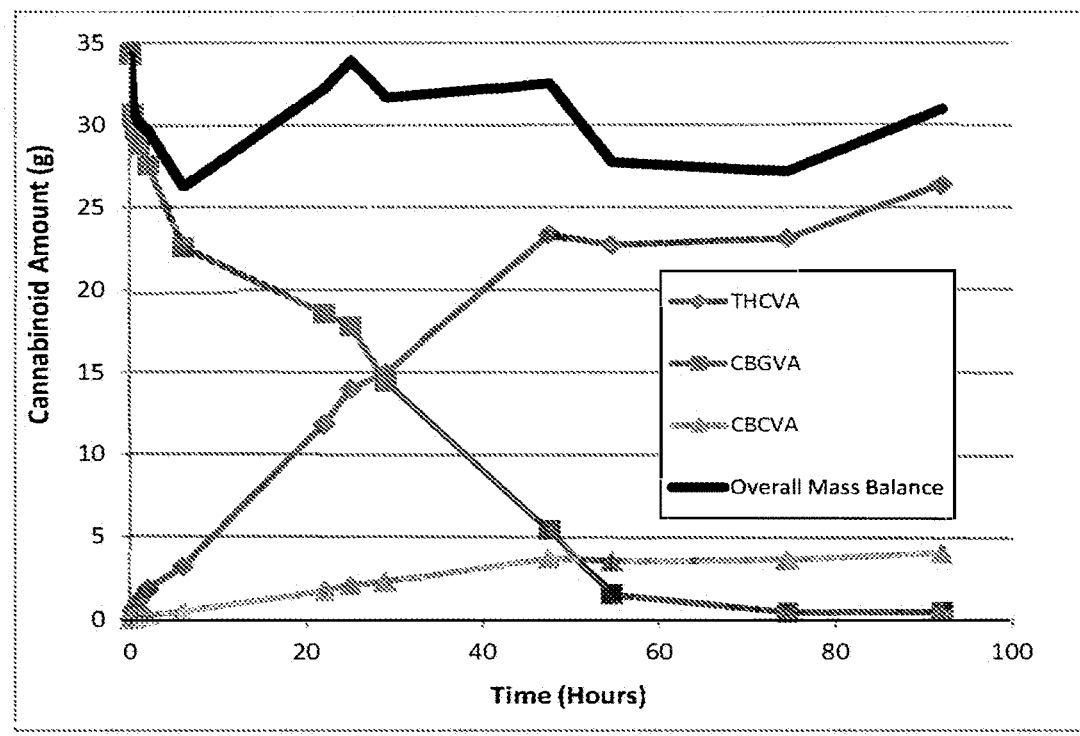
FIG. 42 shows the amount of cannabinoids over the course of the reaction estimated using HPLC standard curves.

In addition to tracking cannabinoids based upon the percentage of HPLC peak area, absolute amounts of cannabinoids were calculated from standard curves to confirm mass balance (FIG. 42). The standard curve provides a more accurate estimate of produced cannabinoids than a method based on the percentage of HPLC peak area because the HPLC percent area chart examines only one wavelength.

Harvest and Extraction

When the reaction agitator stopped, the reaction solution slowly separated to three distinctive phases, which were removed by draining through the bottom outlet valve (BOV).

TABLE 3

Estimated quantities of cannabinoids in each reaction phase as measured by HPLC % peak area, mg/mL concentration, and total grams (the latter two based on standard curves)

| Sample | Vol. mL | CBGVA % Area | mg/mL | g | THCVA % Area | mg/mL | g | CBCVA % Area | mg/mL | g |
|---|---|---|---|---|---|---|---|---|---|---|
| Lower Aqueous | 1050 | 0.78 | 0.002 | 0.002 | 62.20 | 0.15 | 0.16 | 14.47 | 0.02 | 0.25 |
| Middle Aqueous | 800 | 1.40 | 0.04 | 0.031 | 74.33 | 2.25 | 1.80 | 18.07 | 0.37 | 0.29 |
| Upper Emulsion | 1350 | 1.48 | 0.32 | 0.43 | 76.65 | 18.29 | 24.69 | 18.02 | 2.89 | 3.91 |

As shown in Table 3, the lower aqueous phase contained very minor amounts of cannabinoids; the middle phase contained more cannabinoids, but still a minor fraction of the total; the majority of the cannabinoids were found to be present in the upper oil emulsion phase, as expected. The oil emulsion was transferred to a 6 L separatory funnel and extracted with 4 L of methanol by mixing vigorously for 1 minute and allowing the vessel to rest. 3.5 L of methanol phase was recovered and filtered.

About 500 mL of methanol stayed with the oily phase as an emulsion and was not collected until later. The methanol extraction was repeated three more times using 3.5 L of methanol and 1.8 L of upper oily emulsion phase. Each time the extract was filtered by gravity through Whatman 2v folded filter paper, which clarified the solutions. As the sequential extractions were performed, the 1.3 L of oily phase began to separate more from the ~500 mL MeOH emulsion phase. 400 mL of emulsion phase was collected, filtered, and analyzed. Phase contained only trace cannabinoids was discarded. All four methanol extracts were pooled and methanol was removed via evaporation under reduced pressure in a 20 L rotovap at 30-35° C., which yielded about 100 mL of viscous orange oil. The oily material was resuspended using 200 mL of DI water.

Figure 43:
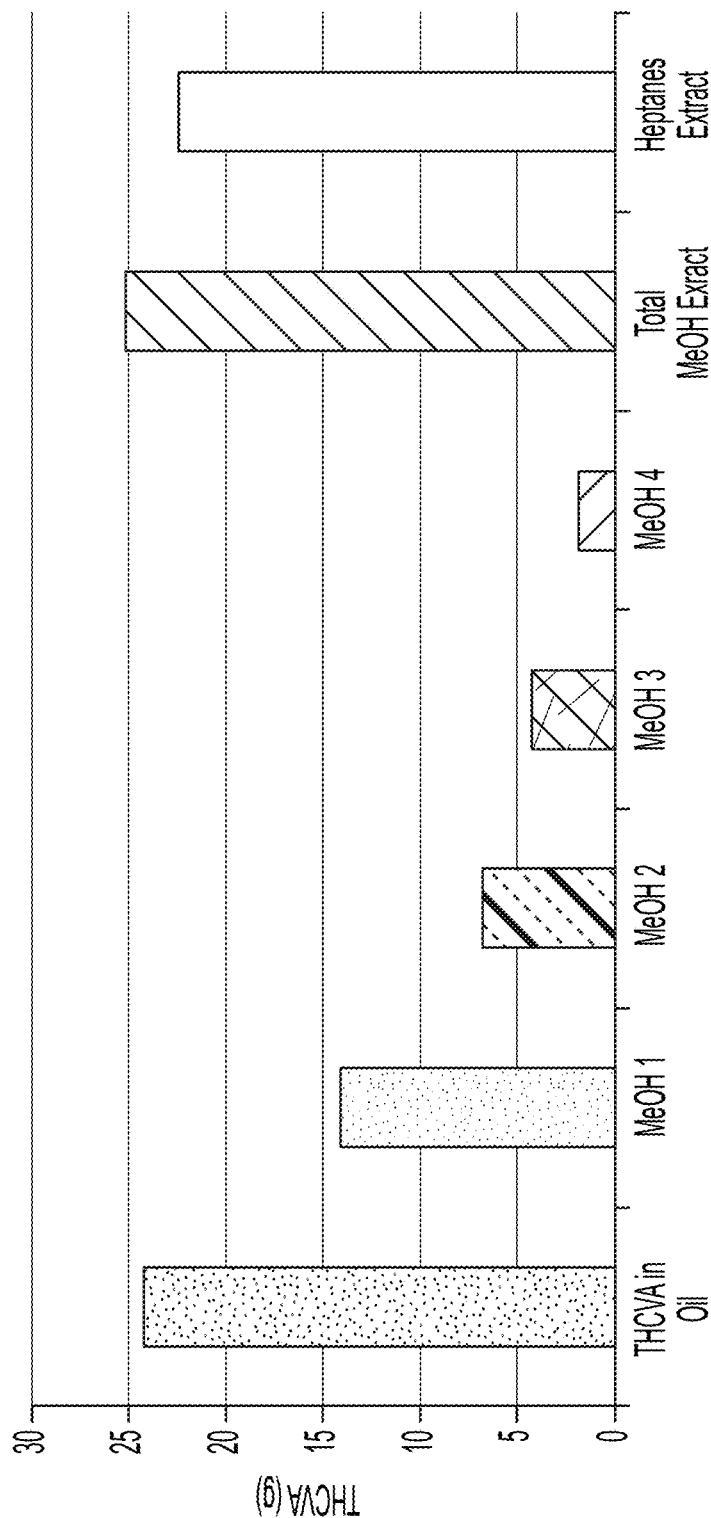
FIG. 43 shows the estimated amount of THCVA present in original oil emulsion and the various extraction stages.

The aqueous/oil solution was also extracted with 3.0 L of heptanes by mixing vigorously in a 4 L separatory funnel and allowing the phases to separate. The phases separated more rapidly than methanol extractions of the oil phase, which resulted in thick emulsions. The heptanes extract was vacuum filtered using a Whatman 3 filter to remove particulates. FIG. 43 showed the amount of THCVA extracted from each stage based on the HPLC analysis.

Since the varin cannabinoids are more polar than the standard cannabinoids, a second extraction was performed using 1 L of 9:1 heptanes-ethyl acetate. HPLC analysis showed that this was unnecessary, as the extract contained only trace amounts of cannabinoids. Minimal $MgSO_4$ was added to the heptanes extract to remove water. The solution was stirred and filtered by gravity using a fluted Whatman filter, resulting in a clarified solution. The heptanes solution was evaporated under reduced pressure. Due to the cannabinoids' ability to entrain heptanes, the material was resuspended in methanol and again subjected to evaporation under reduced pressure followed by vacuum drying overnight at room temperature.

The final crude extract was weighed at 52.76 g, which contained an estimated 22.38 g of THCVA and 3.58 g of CBCVA, with about 50% gravimetric purity. The mass balance of THCVA through the extraction process is summarized in FIG. 43.

Silica Column Chromatography.

A small-scale (15 g/35 mL) silica column purification was conducted on a small side sample of the extract to guide the planned larger (2.5 kg/5 L) columns. 370 mg of dried cannabinoid extract from the 3 L scale up was dissolved in 2 mL of heptanes. 1 mL solution containing 185 mg crude extract with about 90 mg total cannabinoid was loaded on 15 g of silica equilibrated with heptanes with a bed volume of 35 mL. The flow rate was set to 1.0 mL/minute and the column was treated with 3 CV of 95:5 heptanes-ethyl acetate. The first two fractions were collected as a single bed volume (BV) (35 mL volume) while subsequent fractions were collected as 0.5 BV (17.5 mL). Solvent was changed to 9:1 heptanes-EA after 3.0 CV and again changed to 8:2 heptanes-EA after a total of 7.0 BV before finally switching to 1:1 to facilitate rapid CBCVA elution after 11 BV.

Figure 44:
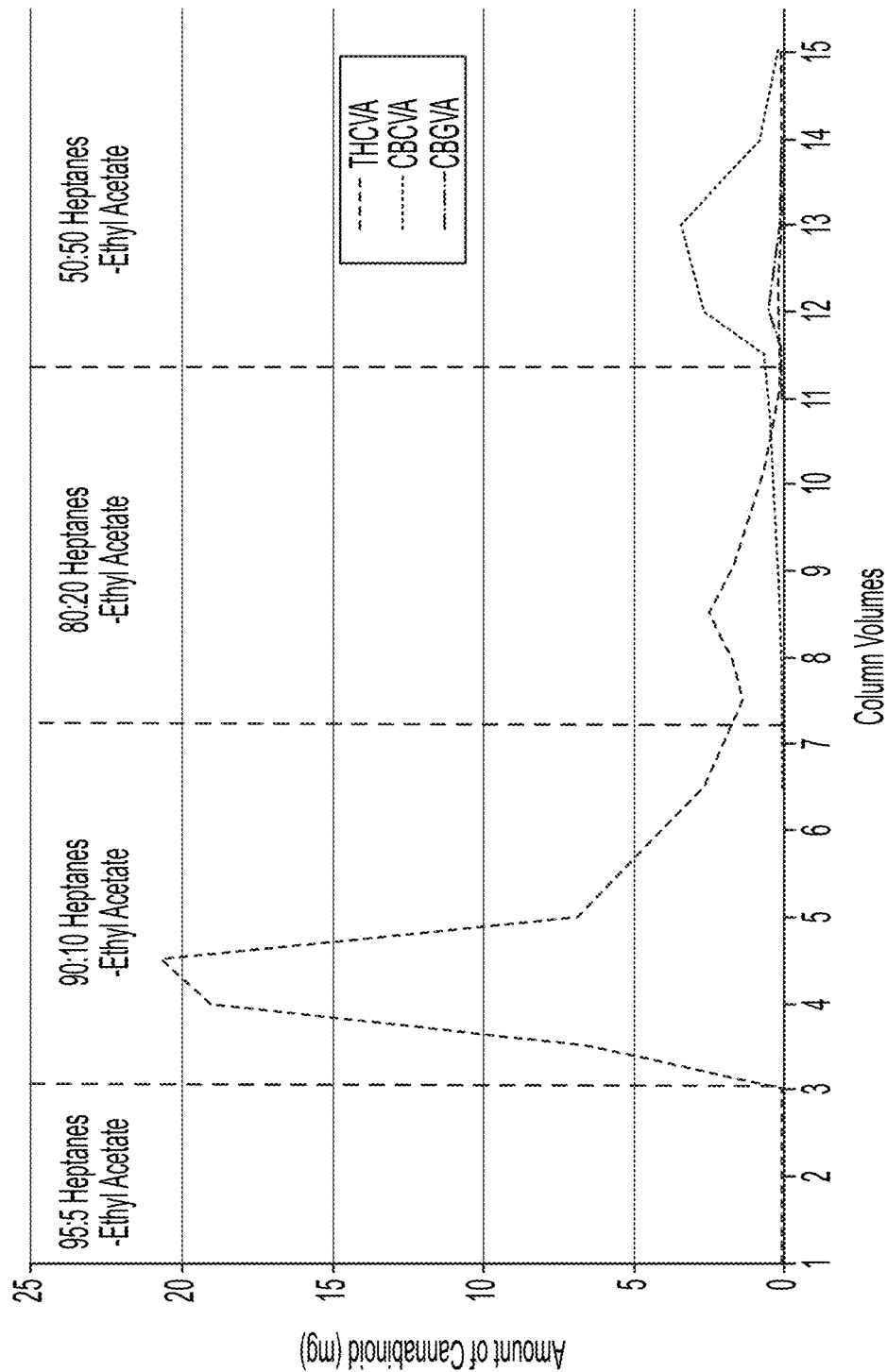
FIG. 44 shows the elution profiles of cannabinoids from small-scale silica column.

The elution profile is consistent with expectations. The THCVA appeared in trace amounts after three bed volume equivalents with the majority of the material eluting between 4.0 and 5.0 CV (FIG. 44). The fraction directly preceding THCVA elution was dried down and found to contain 38 mg of gravimetric impurity. Fractions containing greater than 99% pure THCVA were pooled and found to contain 53.29 mg with a gravimetric mass of 81.90 mg. This pooled material had a gravimetric purity of 65% and an HPLC purity of 99.74%.

A large-scale silica column was used to process half of the crude cannabinoid extract from the 3 L reactions converting 30 g of CBGVA to THCVA and CBCVA. In the large-scale elusion, solvent was changed to 9:1 heptanes-EA after 4.0 CV and again changed to 8:2 heptanes-EA after a total of 8.0 BV before finally switching to 1:1 to facilitate rapid CBCVA elution after 10 BV. Fractions were sampled (100 μL) and dried under nitrogen and dissolved in 200 μL of methanol for HPLC analysis. The elution profile is consistent with the observed elution profile at small-scale (data not shown). In the large-scale elusion profile, fractions 6-32 (CV 3.09-7.82) contained >98% pure THCVA by HPLC at 267 nm and were combined and dried under reduced pressure to yield an estimated 9.76 g of THCVA with an HPLC purity of 99.2%. About 89% of the THCVA was loaded onto the column. The final weight of the dried THCVA pool was 12.49 g with a 78% gravimetric purity. The remaining fractions was divided into various pools and dried for storage and potential isolation at a later time.

THCA Synthase Stability and Potential for Recycle

Figure 45:
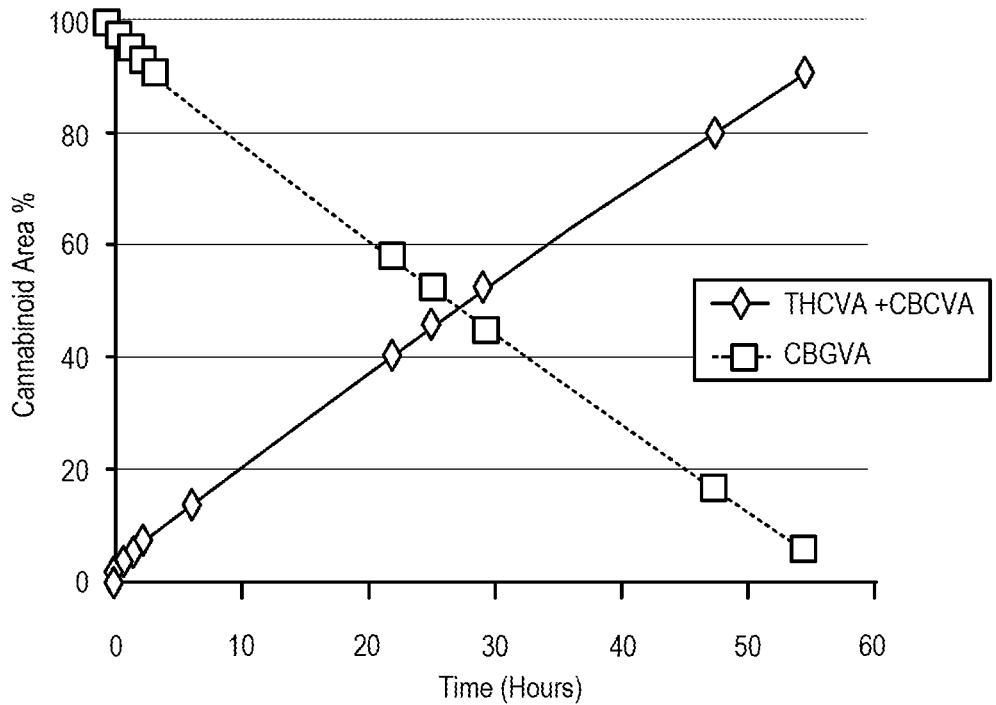
FIG. 45 shows conversion of CBGVA to THCVA and CBCVA over the first 55 hours of reaction.
Figure 46:
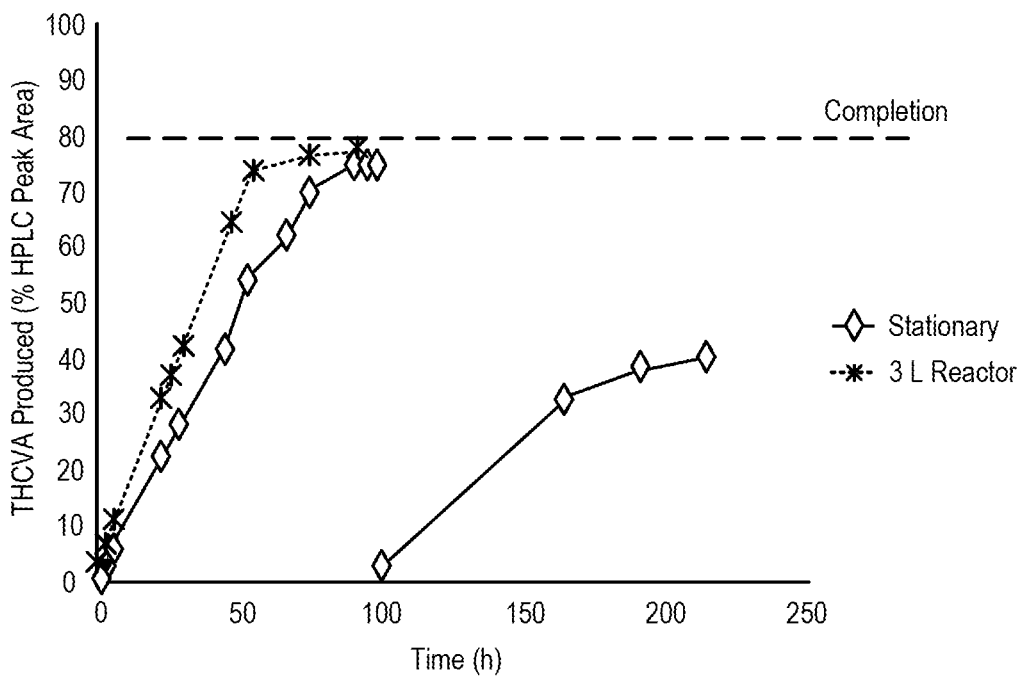
FIG. 46 shows the percentage of THCVA (by HPLC peak area) in reactions with recycled enzyme.
Figure 47A:
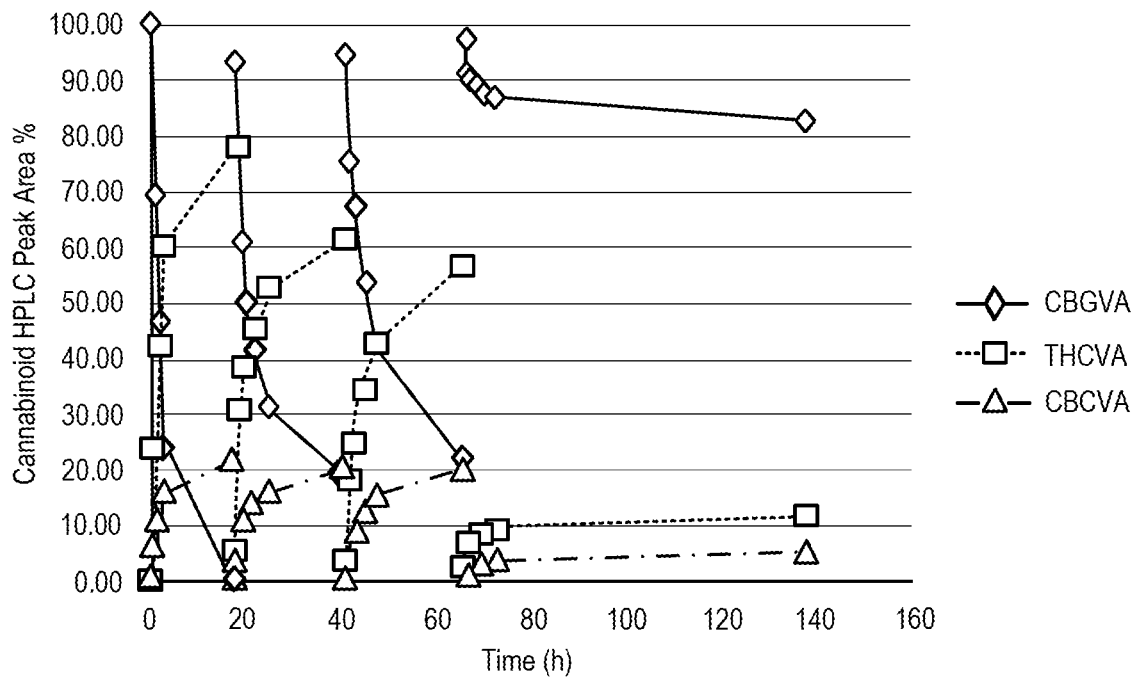
FIGS. 47A-47B show recycle of aqueous phase using dipentene as the organic phase and tech-grade enzyme (A) or enriched enzyme (B).
Figure 47B:
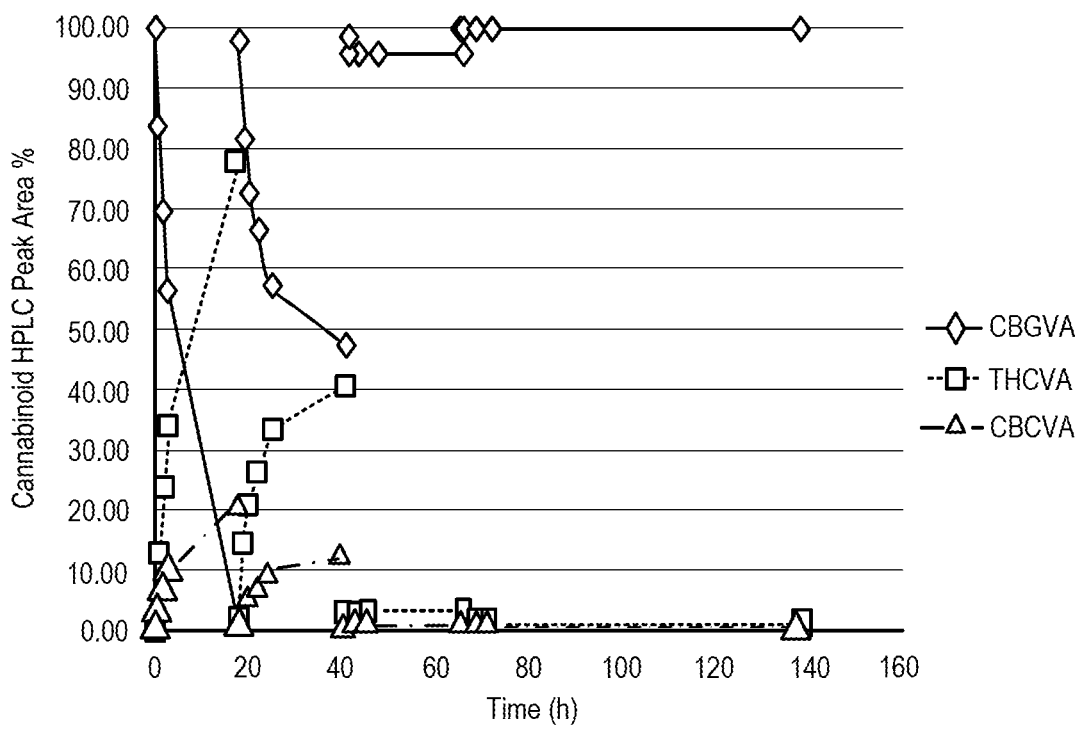
Figure 48A:
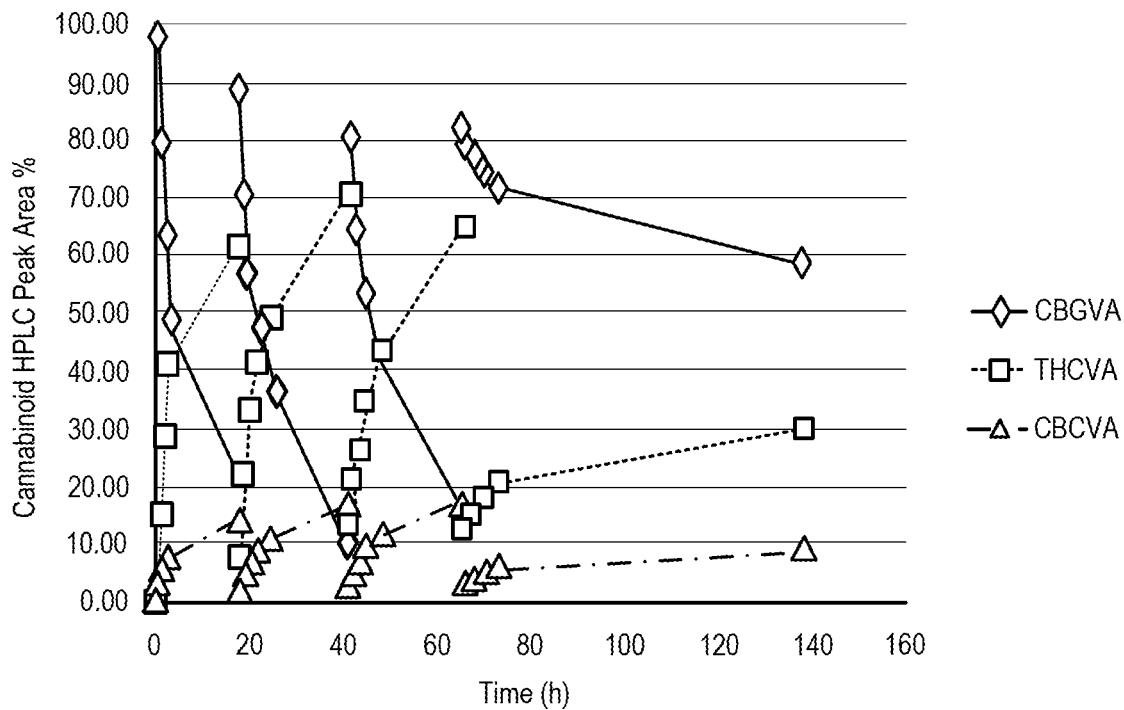
FIG. 48A-48B show recycle of aqueous phase using soybean oil as the organic phase and tech-grade enzyme (A) or enriched enzyme (B).
Figure 48B:
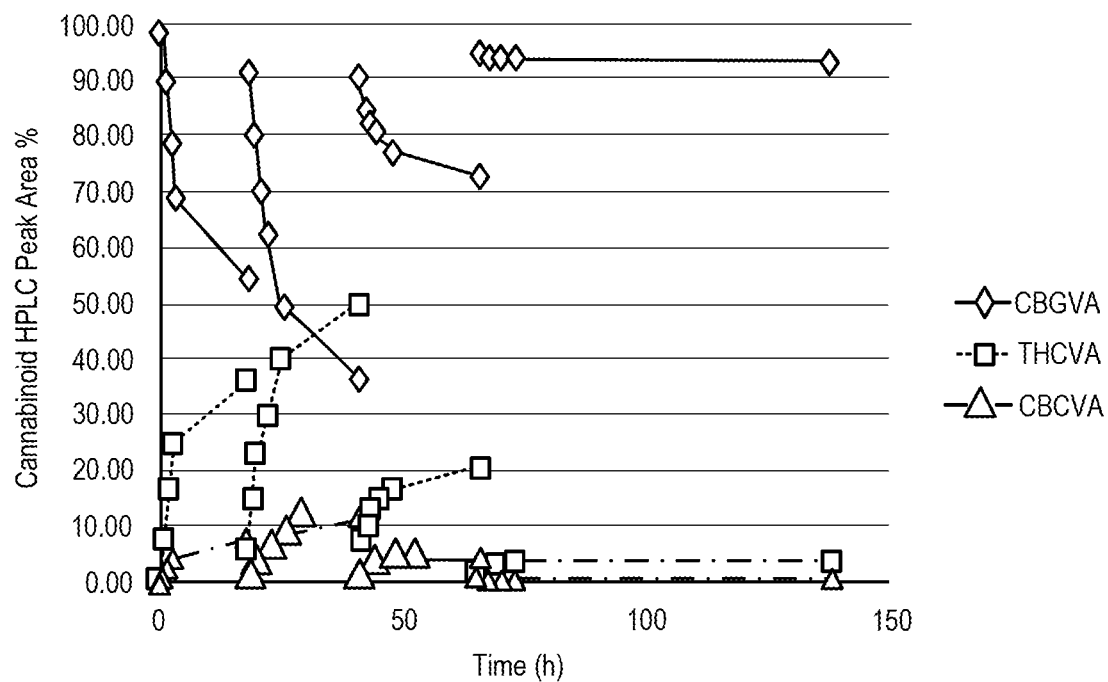

Given the linear conversion of CBGVA to THCVA and CBCVA over the course of the 3 L bioconversion reaction (FIG. 45), the enzymatic activity was evaluated immediately following harvest of the reaction at 92 hours. A recycle experiment was performed with the small-scale stationary reaction. In the experiment, only the oil layer was replaced, leaving the aqueous layer and a thin interface layer intact. Significant activity of THCA synthase was retained in the small scale experiment. The reaction using recycled enzyme proceeded at approximately a third of the rate of the original reaction (FIG. 46).

Figure 49:
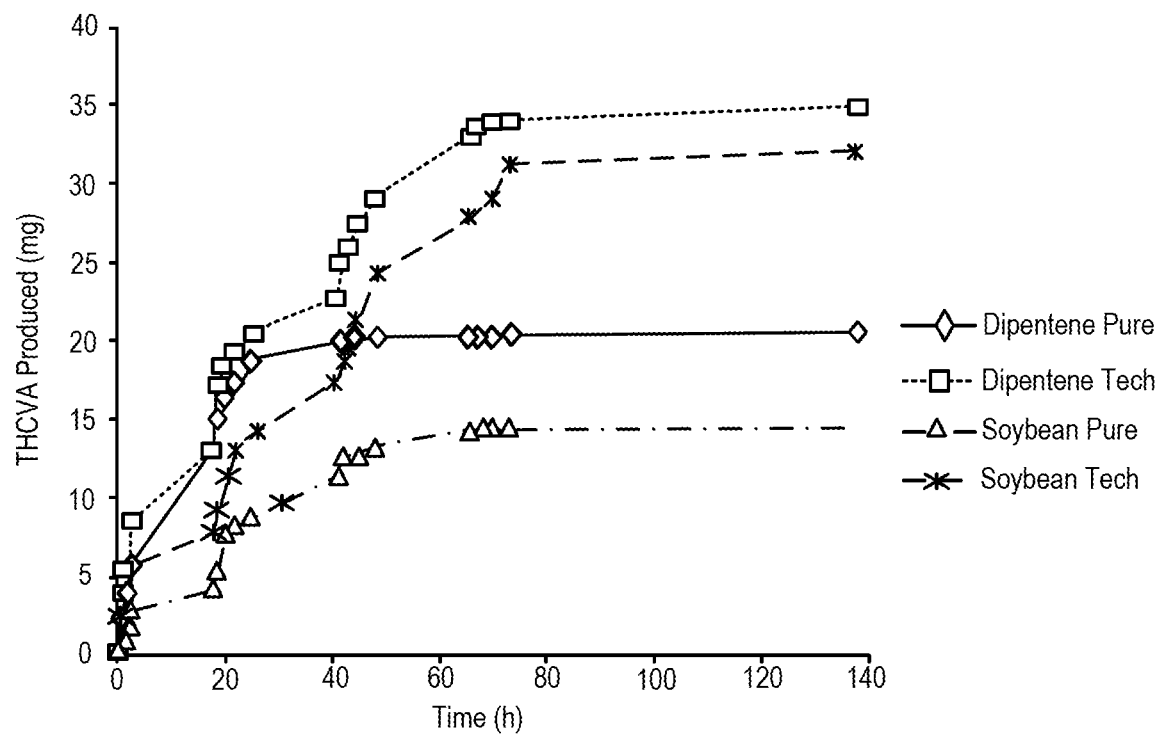
FIG. 49 shows the overall THCVA production of each recycle reaction.

Recycle of the aqueous and interface layer was investigated by using various permutations of soybean oil/dipentene and tech grade/enriched enzyme. Each tech grade enzyme aqueous phase was prepared at 100 mg/mL. Each enriched enzyme aqueous phase was prepared at 1 mg/mL. Organic phases contained 30 g/L CBGVA. For each reaction, 500 uL organic phase was added to 1 mL aqueous phase. After the reaction was initiated, the organic phase was removed and replaced with organic phase containing fresh substrate every 18-24 hours. As shown in FIGS. 47A-47B and 48A-48B, significant enzymatic activities were retained with tech-grade enzyme through 3 reaction cycles. Enriched enzymes exhibited similar initial activity, but lost activity much faster. In the soybean oil with tech-grade enzyme reaction, overall production increased to 32.0 mg THCVA over 4 recycles from 7.6 mg THCVA in a single reaction (FIG. 49).

Example 20 Terpene as the Organic Solvent of the Biphasic System

Reaction with THCA Synthase

Figure 51A:
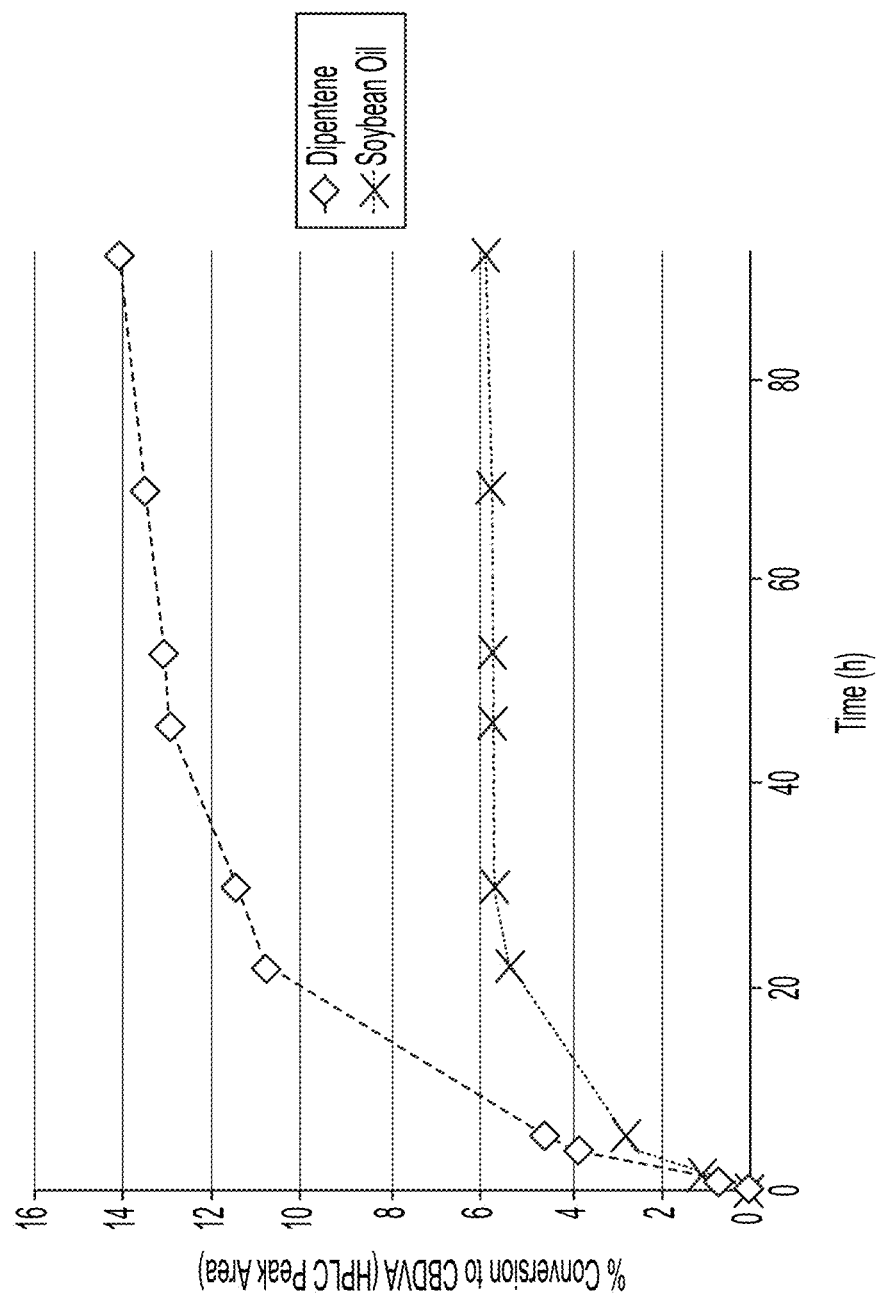
FIGS. 51A-51F shows the bioconversion of CBGVA with CBDA synthase in presence of alternative organic solvent.

Addition of catalase in the aqueous phase or dipentene in the organic phase had a beneficial impact on the efficiency of cannabinoid enzyme (data not shown). Here, Applicant tested if simultaneous addition of catalase and dipentene can further reduce the volume of enzyme in the conversion reaction. Tech-grade THCA synthase was dissolved to 100 g/L in 100 mM sodium citrate at pH 5. The stock solution was without 10% DMSO to avoid potential adverse effects on catalase in the aqueous phase. This stock solution was used to make aqueous phases at 25 g/L, 33 g/L, and 50 g/L THCA synthase. Catalase was added to each diluted THCA synthase solution to a final concentration of 0.1 mg/mL. Aqueous phases at each enzyme concentration were layered with dipentene containing 30 g/L CBGVA to initiate the reaction. The reactions were placed in a 37° C. incubator at 40 rpm and sampled over several days. The extent of reaction (as measured by consumption of substrate) is shown in FIG. 51A.

The 50 g/L enzyme reaction achieved full conversion within 20 hours. Surprisingly, the 33 g/L reaction also achieved almost full conversion in about 48 hours. The reaction with 25 g/L THCA synthase did not achieve completion. 33 g/L THCA was comparably lower than previous experiment to fully convert 30 g/L CBGVA. For example, the concentration was one third of that used in the 3 L scale-up demonstration (100 g/L) in Example 19.

Figure 50A:
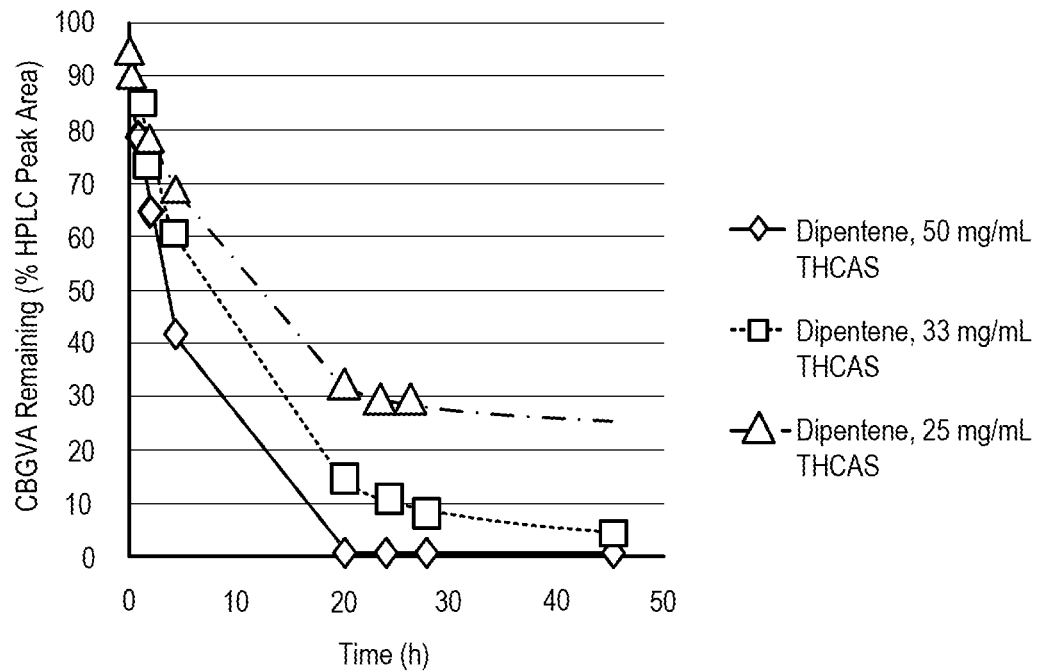
FIGS. 50A-50F shows the bioconversion of CBGVA with THCA synthase in presence of alternative organic solvent.
Figure 50B:
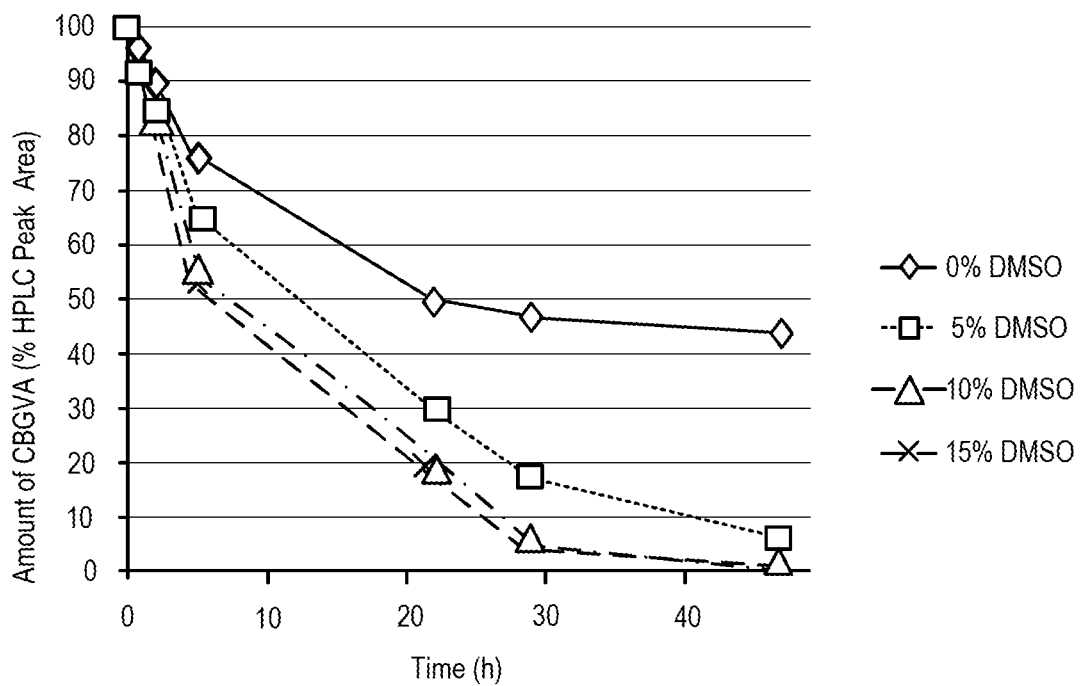
Figure 50C:
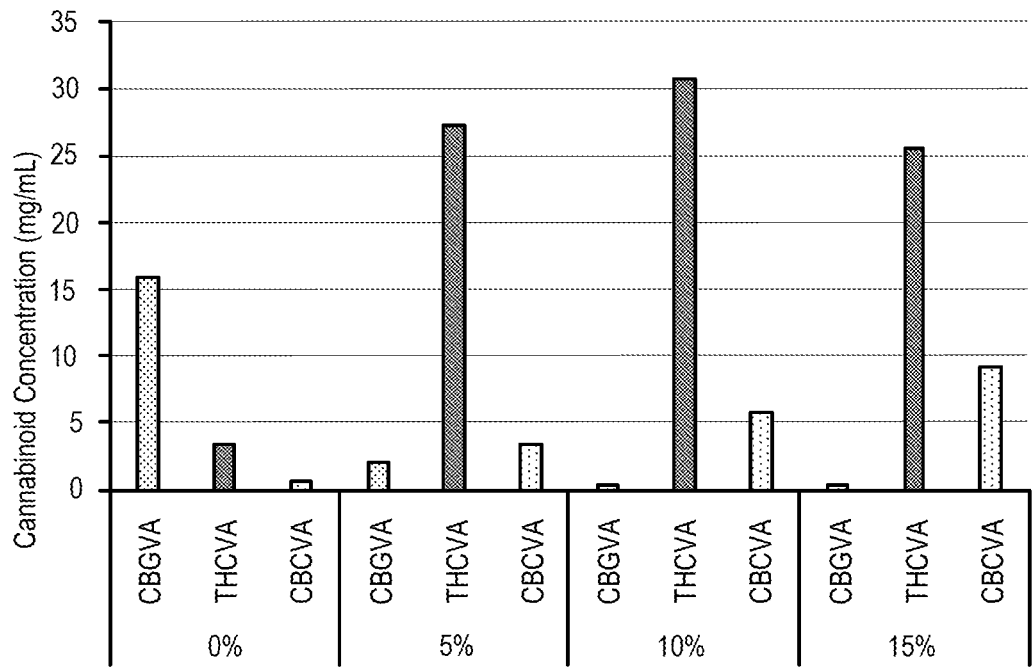

A separate experiment was conducted to test if 25 g/L THCA synthase can fully convert 30 g/L CBGVA through co-solvent optimization. Here, tech-grade THCA synthase was dissolved to 25 g/L in 100 mM sodium citrate (pH 5) with 0.1 mg/mL catalase and 0%, 5%, 10%, or 15% DMSO. Aqueous phases with DMSO were layered with dipentene containing 30 g/L CBGVA to initiate the reaction. The reactions were placed in a 37° C. incubator at 40 rpm and sampled over two days. The extent of reaction (as measured by consumption of substrate) is shown in FIGS. 50A and 50B. As previous experiment, 25 g/L enzyme with no co-solvent did not achieve complete conversion of CBGVA. However, the conversion of CBGVA was completed with 5%, 10%, and 15% DMSO. Increasing the concentration of DMSO in aqueous solution also shifted the product ratio toward CBCVA (FIG. 50C). At a high DMSO concentration (15%), the overall production of THCVA decreased. Without being bound by a theory, a moderate concentration of DMSO (5-10%) favors the production of THCVA without significant amounts of CBCVA.

To further test the effect of dipentene on CBGVA conversion, a similar experiment was carried in a scale-up system (300 mL). 3 g of CBGVA was dissolved in 100 mL of dipentene in a 250 mL bottle (30 g/L), with incubation at 37° C. and intermittent swirling. After several minutes, the CBGVA appeared to have fully dissolved, with a brownish layer of material on the bottom of the bottle. The CBGVA concentration was estimated at 31 g/L with HPLC analysis. After overnight incubation, the CBGVA solution was centrifuged at 6,800×g for 5 minutes to remove the formed crystals and then was measured at 29 g/L.

In setting up the 300 mL jacketed reactor, Applicant took extra measures to minimize losses of organic phase to evaporation, including adding a stir shaft collar, replacing the headplate gasket with a type that provides a better seal, and using plugs and parafilm to block other potential points for evaporative loss. The temperature control unit was set at 37° C. and the reactor jacket was circulated with solution. Two Rushton impellors were aligned with the bottom impellor placed as close as possible to the bottom of reactor. The top impellor was placed at around 200 mL mark on reactor. The pH probe was calibrated with pH 7 and pH 4 standards.

5 g of lyophilized tech-grade THCA synthase was dissolved in 200 mL 100 mM sodium citrate buffer with 10% DMSO (pH 5.0) and 20 mg of catalase. The enzyme solution was added to the reactor and was stirred at 250 rpm. The pH probe was inserted and secured on the reactor with pH maintained at 5.0. The gaps around the probe were sealed with parafilm. Once the temperature of enzyme solution stabilized at about 36° C., 100 mL of clarified dipentene solution containing CBGVA was added to the reactor.

Figure 50D:
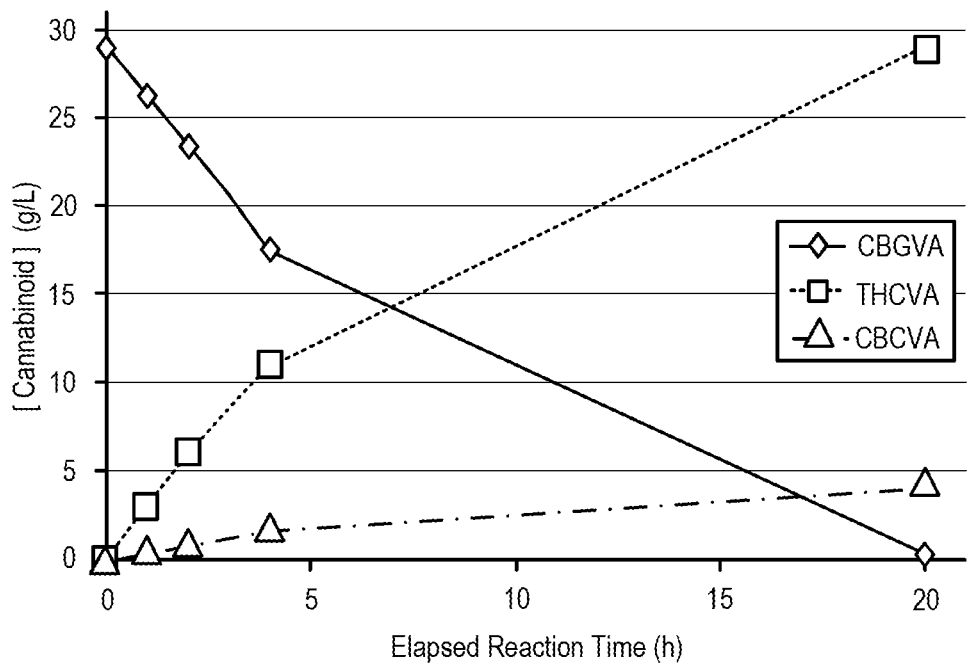

As shown in FIG. 50D, the reaction progressed rapidly to completion within 20 hours. Particularly, over 11 g/L of THCVA were produced after 4 hours, and ratios of THCVA to CBCVA remained at around 7:1 throughout the reaction. After 20 hours the reaction was complete, with only 0.3 mg/mL of CBGVA substrate remaining in the dipentene, and 28.86 g/L of THCVA produced. Over the course of the reaction, the total cannabinoid concentration increased gradually from 29 g/L to 33 g/L, suggesting that there was some minimal loss of dipentene.

Figure 50E:
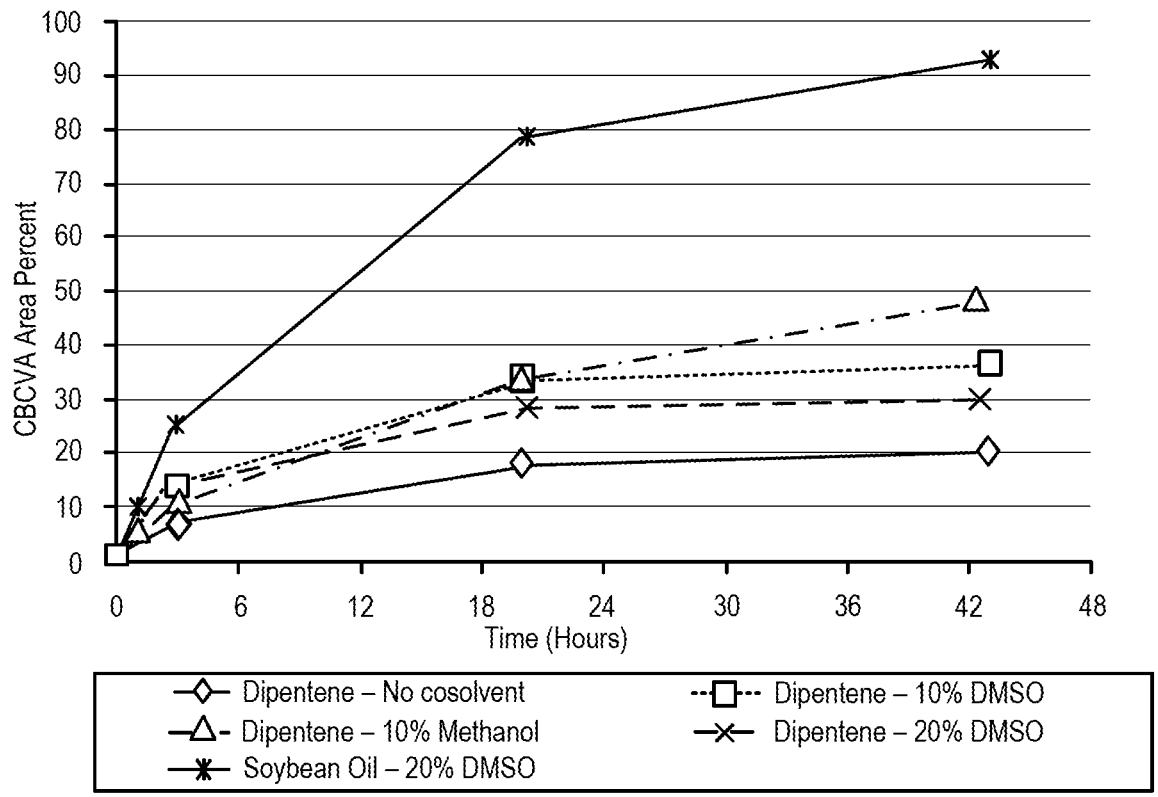

As noted above, replacing soybean oil with dipentene in the organic phase can increase the efficiency of biphasic reactions at a low pH. Here, the production of CBCVA was further evaluated at a higher pH with dipentene and various cosolvents. Four different aqueous buffers were made using different cosolvents with the buffer adjusted to pH 7 after the cosolvent was added:
  i. Condition 1: 100 mM HEPES, pH 7, 30 mg/mL THCA synthase BPD1090-500, and 0.1 mg/mL Catalase (no cosolvent)
  ii. Condition 2: 100 mM HEPES, pH 7, 30 mg/mL THCA synthase BPD1090-500, 0.1 mg/mL Catalase, and 10% DMSO
  iii. Condition 3: 100 mM HEPES, pH 7, 30 mg/mL THCA synthase BPD1090-500, 0.1 mg/mL Catalase, and 10% MeOH
  iv. Condition 4: 100 mM HEPES, pH 7, 30 mg/mL THCA synthase BPD1090-500, 0.1 mg/mL Catalase, and 20% DMSO 400 µL of dipentene solution containing about 30 mg/mL CBGVA was overlaid onto 800 µL of the aqueous buffer. In addition, 400 µL of soybean oil containing comparable CBGVA was overlaid onto another vial containing aqueous condition 4 to act as a control. The reaction solutions were sampled at various time points over two days and are summarized in FIG. 50E. The addition of a co-solvent had a positive effect on the production of CBCVA when compared to the non-co-solvent control.

Figure 50F:
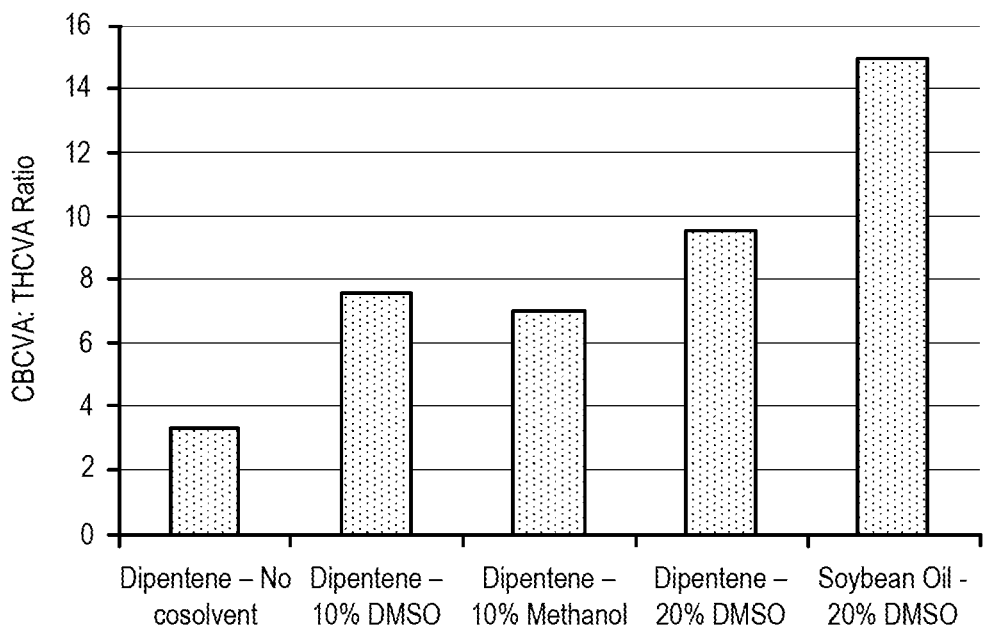

The standard soybean oil with 20% DMSO reaction significantly outperformed all of the reactions with dipentene and had the highest ratio of CBCVA to THCVA of any reaction (FIG. 50F). Very little THCVA (less than 5%) was produced in these reactions. Without being bound by a theory, it appears that dipentene had little effect on the reactions that occur at higher pH.

CBDA Synthase Reaction

CBDA synthase was dissolved to 100 mg/mL in 100 mM sodium citrate, pH 5. 1 mL of this enzyme solution was added to 500 uL of 30 g/L CBGVA in either dipentene or soybean oil. The reaction was then incubated at 37° C. on a 40 rpm rotator and sampled over several days. The dipentene reaction performed significantly better than the soybean oil reaction (FIG. 51A), producing over twice the amount of CBDVA. Interestingly, unlike THCA synthase, the initial rates were similar between dipentene and soybean oil, and the faster rate was sustained longer in dipentene.

To further investigate the effects of co-solvent and catalase on CBDA synthase, 100 mg/mL 900 uL CBDA synthase (100 mg/mL) solution (100 mM sodium citrate, pH 5) was mixed with different co-solvents (100 uL additional buffer, 100 uL MeOH, or 100 uL 1 mg/mL catalase). Then, 500 uL of 30 g/L CBGVA in either dipentene or soybean oil was added to the CBDA synthase solution to initiate the reaction. The reaction was then incubated at 37° C. on a 40 rpm rotator and sampled over several days.

Figure 51B:
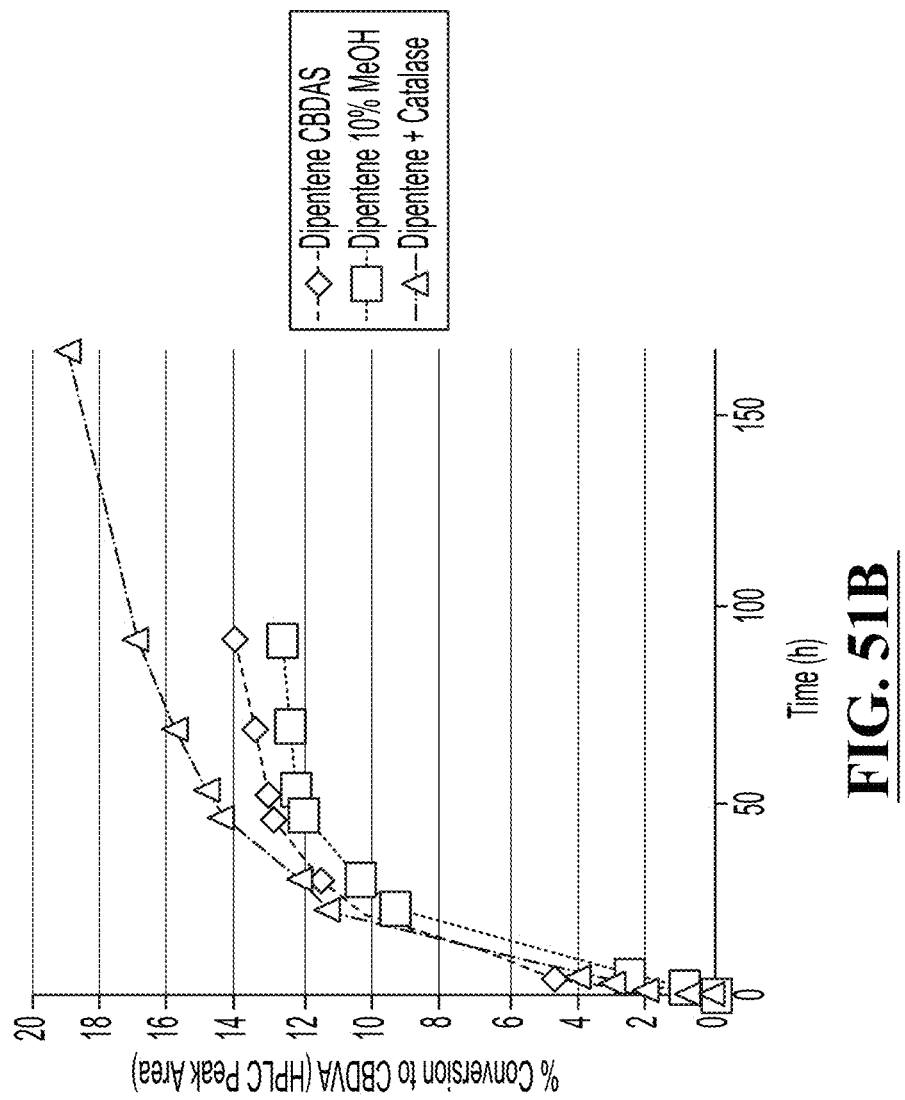
Figure 51C:
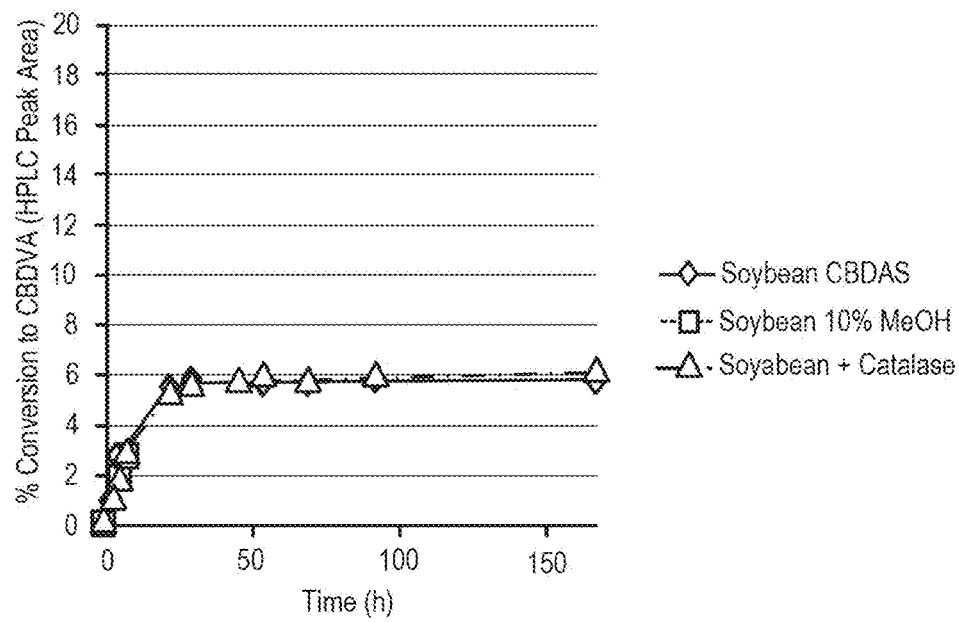

Biosynthesis with CBDA synthase using soybean oil is less efficient than dipentene. Compare FIG. 51B with FIG. 51C. Catalase appeared to allow the dipentene reaction to sustain at a high conversion rate for a longer period of time (FIG. 51B). This beneficial effect seems absent, however, in the soybean oil reaction (FIG. 51C). This is consistent with Applicant's previous observation that catalase can promote the high-productive reactions.

Figure 51D:
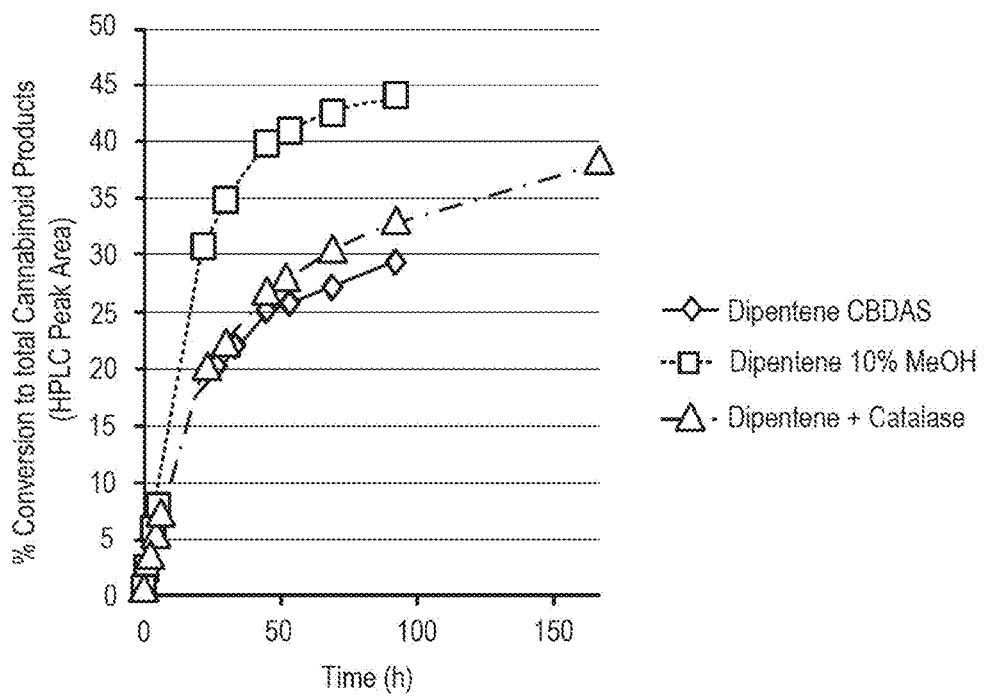

The inclusion of methanol as a co-solvent enhanced production of total cannabinoids (FIG. 51D).

Figure 51E:
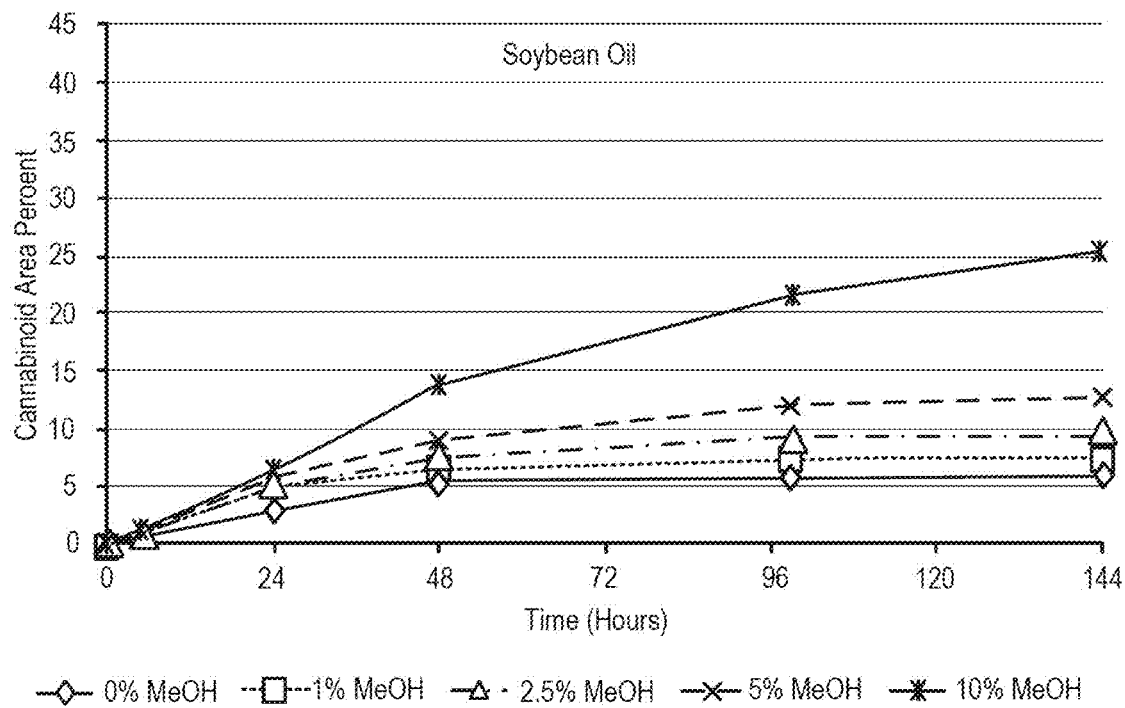
Figure 51F:
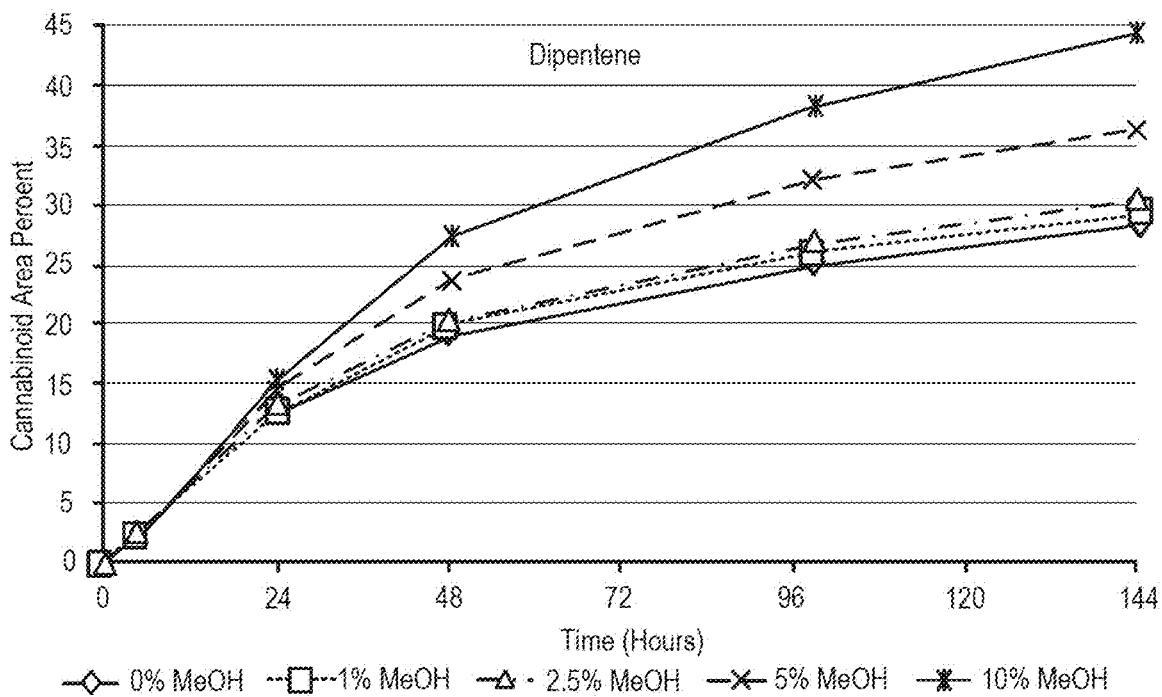

To further determine the optimal concentration of methanol for the CBDA synthase activity, 40 mg/mL CBDA synthase in five buffers (100 mM sodium citrate, pH 5) with different concentrations of methanol (0%, 1%, 2.5%, 5%, or 10%). 400 µL of dipentene or soybean oil each containing about 10 mg/mL CBGVA was overlaid onto 800 µL of aqueous enzyme solution. Reactions took place in 2.0 mL glass vials and were placed on a vertical tube roller (30 rpm) at ambient temperature. Samples were taken over six days to assess the production of CBDVA. The dipentene-MeOH biphasic system produced more total cannabinoids (CBDVA, THCVA, & CBCVA) than the soybean oil-MeOH system (FIGS. 51E and 51F). Further, 10% MeOH improved the total cannabinoid production with either soybean oil or dipentene (FIGS. 51E and 51F).

Comparison of Dipentene and Soybean Oil Reactions

Figure 52:
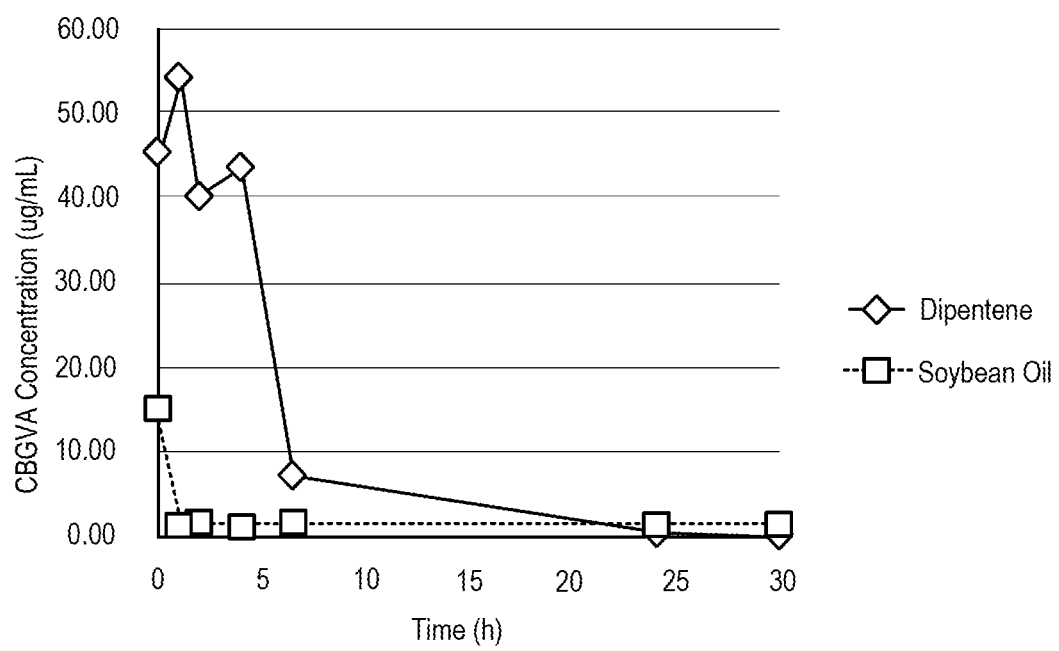
FIG. 52 shows comparison of substrate concentrations in the aqueous phase for the dipentene and soybean oil reactions.

To further compare the biphasic reactions with dipentene and soybean oil, standard 1.5 mL reactions were set up using 100 g/L THCA synthase and 10% DMSO in the aqueous phase and 30 g/L CBGVA in either dipentene or soybean oil as the organic phase. At each time point, both the oil phase and aqueous phase were sampled, using an exhaustive sampling procedure to minimize any organic contamination of the aqueous samples. As illustrated in FIG. 52, cannabinoid substrate concentrations are greater in dipentene than in soybean oil. The mass transfer of cannabinoid substrate from dipentene into the aqueous phase was more rapid than the mass transfer of cannabinoid substrate from soybean oil into the aqueous phase (FIG. 52).

EQUIVALENTS

It is to be understood that while the disclosure has been described in conjunction with the above embodiments, the foregoing description and examples are intended to illustrate and not limit the scope of the disclosure. Other aspects, advantages, and modifications within the scope of the disclosure will be apparent to those skilled in the art to which the disclosure pertains.

Unless otherwise defined, all technical and scientific terms used herein have the same meaning as commonly understood by one of ordinary skill in the art to which this disclosure belongs.

The embodiments illustratively described herein may suitably be practiced in the absence of any element or elements, limitation, or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

Thus, it should be understood that although the present disclosure has been specifically disclosed by specific embodiments and optional features, modification, improvement, and variation of the embodiments therein herein disclosed may be resorted to by those skilled in the art, and that such modifications, improvements, and variations are considered to be within the scope of this disclosure. The materials, methods, and examples provided here are representative of particular embodiments, are exemplary, and are not intended as limitations on the scope of the disclosure.

The scope of the disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

In addition, where features or aspects of the disclosure are described in terms of Markush groups, those skilled in the art will recognize that embodiments of the disclosure may also thereby be described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A biphasic composition comprising:
   (a) a cannabinoid precursor in a first phase, wherein the cannabinoid precursor is compound of Formula II:

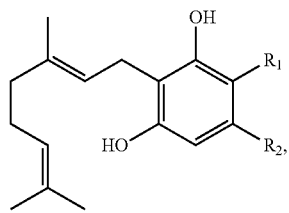

Formula II wherein $R_1$ is H or COOH and $R_2$ is a linear or branched $CH_3$, $C_2H_5$, $C_3H_7$, $C_4H_9$, $C_5H_{10}$, $C_6H_{13}$, $C_7H_{15}$ or $C_8H_{17}$ group; and
   (b) a cannabinoid synthase in a second phase,
   wherein the first phase comprises an organic solvent and the second phase comprises an aqueous solvent, and wherein the organic solvent comprises olive oil, sesame oil, castor oil, cotton-seed oil, soybean oil, pentane, heptane, octane, isooctane, nonane, decane, or terpene.

2. The biphasic composition of claim 1, wherein the organic solvent comprises a terpene.

3. The biphasic composition of claim 1, wherein the terpene comprises dipentene.

4. The biphasic composition of claim 1, wherein the organic solvent comprises olive oil, sesame oil, castor oil, cotton-seed oil, or soybean oil.

5. The biphasic composition of claim 1, wherein the aqueous solvent further comprises dimethyl sulfoxide (DMSO), dimethylformamide (DMF), dimethylacetamide (DMA), isopropyl alcohol, cyclodextrin, peroxide scavenger, or methanol (MeOH).

6. The biphasic composition of claim 1, wherein the volume ratio of the first phase to the second phase is about 2:1.

7. The biphasic composition of claim 1, wherein the aqueous solvent further comprises DMSO in a range between about 5% and about 10% of the aqueous solution, and wherein the pH value of the aqueous solution is between about 5.5 and about 7.5.

8. The biphasic composition of claim 1, wherein the cannabinoid precursor is cannabigerolic acid (CBGA) or cannabigerovarinic acid (CBGVA).

9. The biphasic composition of claim 1, wherein the cannabinoid synthase is CBDA synthase or THCA synthase.

10. A method for producing a cannabinoid product comprising:
   contacting a cannabinoid precursor in a first phase with a cannabinoid synthase in a second phase, wherein the cannabinoid precursor is the compound of Formula II:

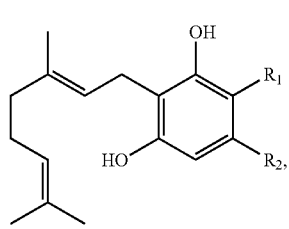

Formula II wherein $R_1$ is H or COOH and $R_2$ is a linear or branched $CH_3$, $C_2H_5$, $C_3H_7$, $C_4H_9$, $C_5H_{10}$, $C_6H_{13}$, $C_7H_{15}$ or $C_8H_{17}$ group, wherein the first phase comprises an organic solvent and the second phase comprises an aqueous solvent, and wherein the organic solvent comprises olive oil, sesame oil, castor oil, cotton-seed oil, soybean oil, pentane, heptane, octane, isooctane, nonane, decane, or terpene.

11. The method of claim 10, wherein the organic solvent comprises a terpene.

12. The method of claim 11, wherein the terpene comprises dipentene.

13. The method of claim 10, wherein the organic solvent comprises olive oil, sesame oil, castor oil, cotton-seed oil, or soybean oil.

14. The method of claim 10, wherein the aqueous solvent further comprises dimethyl sulfoxide (DMSO), dimethylformamide (DMF), dimethylacetamide (DMA), isopropyl alcohol, cyclodextrin, peroxide scavenger, or methanol (MeOH).

15. The method of claim 10, wherein the volume ratio of the first phase to the second phase is about 2:1.

16. The method of claim 10, wherein the aqueous solvent further comprises DMSO in a range between about 5% and about 10% of the aqueous solution, and wherein the pH value of the aqueous solution is between about 5.5 and about 7.5.

17. The method of claim 10, wherein the cannabinoid precursor is cannabigerolic acid (CBGA) or cannabigerovarinic acid (CBGVA).

18. The method of claim 10, wherein the cannabinoid synthase is CBDA synthase or THCA synthase.

19. The method of claim 10 further comprising agitating the first phase to form micro-droplets comprising the cannabinoid precursor.

* * * * *